United States Patent
Darty et al.

(10) Patent No.: US 9,526,427 B2
(45) Date of Patent: Dec. 27, 2016

(54) COMPACT LIGHT SENSORS WITH SYMMETRICAL LIGHTING

(71) Applicant: Hypermed Imaging, Inc., Memphis, TN (US)

(72) Inventors: Mark Anthony Darty, Collierville, TN (US); Michael Tilleman, Brookline, MA (US); Peter Meenen, Cane Ridge, TN (US); Dmitry Yudovsky, Los Angeles, CA (US)

(73) Assignee: Hypermed Imaging, Inc., Memphis, TN (US)

( * ) Notice: Subject to any disclaimer, the term of this patent is extended or adjusted under 35 U.S.C. 154(b) by 0 days.

(21) Appl. No.: 15/151,419

(22) Filed: May 10, 2016

(65) Prior Publication Data

US 2016/0249810 A1 Sep. 1, 2016

Related U.S. Application Data

(63) Continuation-in-part of application No. 14/664,754, filed on Mar. 20, 2015.

(60) Provisional application No. 61/969,039, filed on Mar. 21, 2014, provisional application No. 62/090,302, filed on Dec. 10, 2014.

(51) Int. Cl.
| | |
|---|---|
| *G01N 21/25* | (2006.01) |
| *A61B 5/00* | (2006.01) |
| *A61B 5/145* | (2006.01) |
| *G01J 3/28* | (2006.01) |
| *G01J 3/02* | (2006.01) |

(52) U.S. Cl.
CPC .......... *A61B 5/0075* (2013.01); *A61B 5/0079* (2013.01); *A61B 5/145* (2013.01); *A61B 5/443* (2013.01); *A61B 5/444* (2013.01); *A61B 2090/309* (2016.02); *A61B 2562/0238* (2013.01); *G01J 3/0208* (2013.01); *G01J 3/2803* (2013.01); *G01J 3/2823* (2013.01); *G01J 2003/2826* (2013.01)

(58) Field of Classification Search
CPC .............. A61B 5/00; A61B 5/145; G01J 3/51; G01J 3/02; G01J 3/513; G01J 3/2803; G01J 3/46
See application file for complete search history.

(56) References Cited

U.S. PATENT DOCUMENTS

2015/0051498 A1* 2/2015 Darty .................. G01N 21/255
600/477

* cited by examiner

*Primary Examiner* — Abdullahi Nur
(74) *Attorney, Agent, or Firm* — Brett A. Lovejoy; Andrew J. Antczak; Morgan, Lewis & Bockius, LLP

(57) ABSTRACT

Provided are methods and systems for concurrent imaging at multiple wavelengths. In one aspect, an imaging device includes at least one objective lens configured to receive light backscattered by an object, a plurality of pixel array photo-sensors, a plurality of bandpass filters covering respective photo-sensors, where each bandpass filter is configured to allow a different respective spectral band to pass through the filter, and a beam steering assembly in optical communication with the at least one objective lens and the photo-sensors. The beam steering assembly directs light received by at least one objective lens from the tissue of a subject to at least one pixel array photo-sensor in the plurality of pixel array photo-sensors.

50 Claims, 22 Drawing Sheets

TOP VIEW

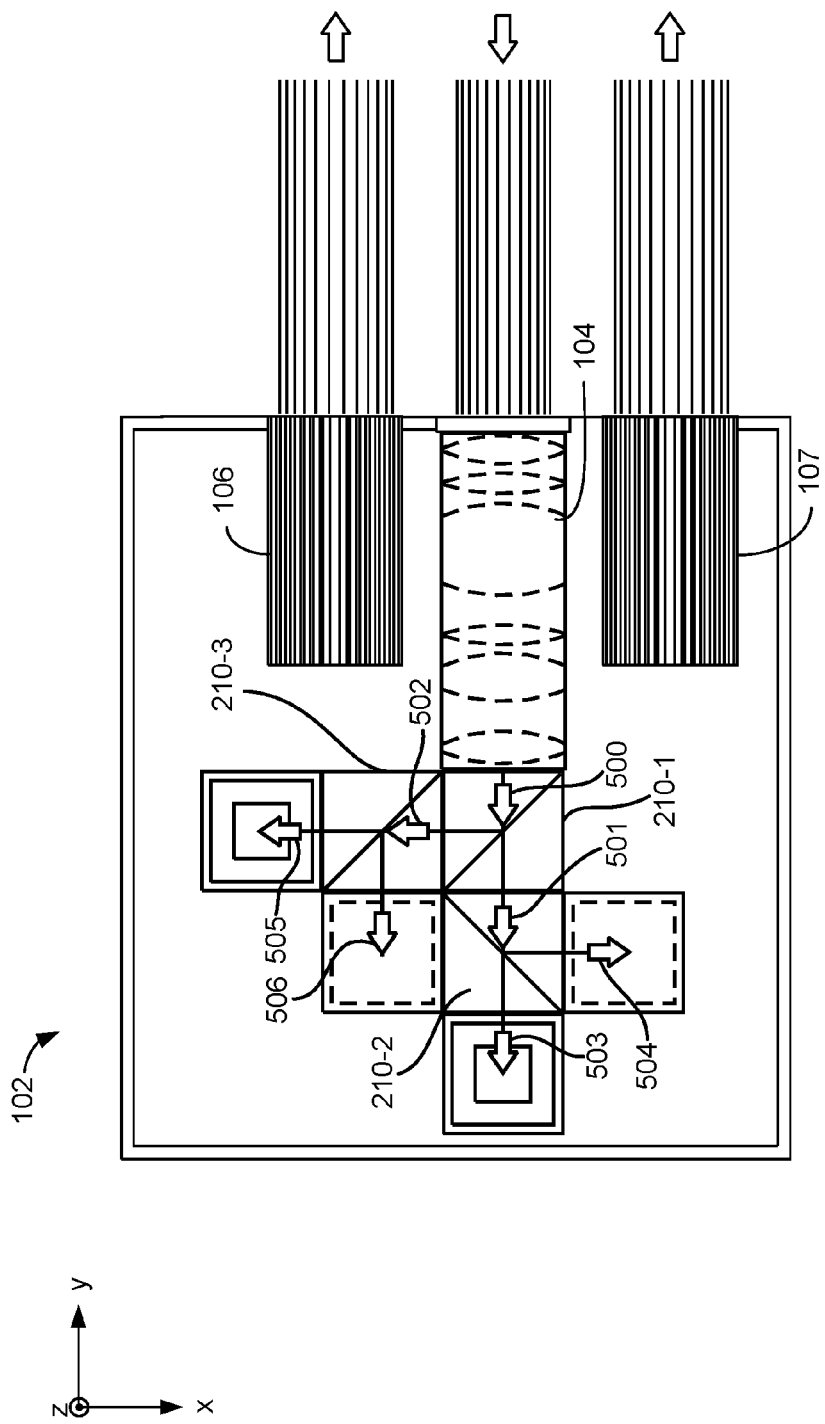

FRONT VIEW

TOP VIEW

TOP VIEW

TOP VIEW

COMPACT LIGHT SENSORS WITH SYMMETRICAL LIGHTING

CROSS REFERENCE TO RELATED APPLICATIONS

This application in is a Continuation-In-Part of U.S. patent application Ser. No. 14/664,754 entitled "Compact Light Sensor", filed Mar. 20, 2015, which in turn claims priority to U.S. Provisional Patent Application No. 61/969,039, filed Mar. 21, 2014, and U.S. Provisional Patent Application No. 62/090,302, filed Dec. 10, 2014, the disclosures of which are hereby incorporated by reference herein in their entireties for all purposes.

TECHNICAL FIELD

The present disclosure generally relates to spectroscopy, such as hyperspectral spectroscopy, and in particular, to systems, methods and devices enabling a compact imaging device.

BACKGROUND

Hyperspectral (also known as "multispectral") spectroscopy is an imaging technique that integrates multiple images of an object resolved at different spectral bands (e.g., ranges of wavelengths) into a single data structure, referred to as a three-dimensional hyperspectral data cube. Data provided by hyperspectral spectroscopy is often used to identify a number of individual components of a complex composition through the recognition of spectral signatures of the individual components of a particular hyperspectral data cube.

Hyperspectral spectroscopy has been used in a variety of applications, ranging from geological and agricultural surveying to surveillance and industrial evaluation. Hyperspectral spectroscopy has also been used in medical applications to facilitate complex diagnosis and predict treatment outcomes. For example, medical hyperspectral imaging has been used to accurately predict viability and survival of tissue deprived of adequate perfusion, and to differentiate diseased (e.g., cancerous or ulcerative) and ischemic tissue from normal tissue.

However, despite the great potential clinical value of hyperspectral imaging, several drawbacks have limited the use of hyperspectral imaging in the clinic setting. In particular, medical hyperspectral instruments are costly because of the complex optics and computational requirements conventionally used to resolve images at a plurality of spectral bands to generate a suitable hyperspectral data cube. Hyperspectral imaging instruments can also suffer from poor temporal and spatial resolution, as well as low optical throughput, due to the complex optics and taxing computational requirements needed for assembling, processing, and analyzing data into a hyperspectral data cube suitable for medical use.

Thus, there is an unmet need in the field for less expensive and more rapid means of hyperspectral/multispectral imaging and data analysis. The present disclosure meets these and other needs by providing methods and systems for concurrently capturing images at multiple wavelengths.

SUMMARY

Various implementations of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various implementations are used to enable a hyperspectral imaging device capable of producing a three-dimensional hyperspectral data cube using a plurality of photosensor chips (e.g., CDD, CMOS, etc.) suitable for use in a number for applications, and in particular, for medical use.

One aspect of the present disclosure is directed to an imaging device comprising a housing having an exterior and an interior including at least one objective lens attached to or within the housing. A plurality of light source sets are radially disposed on the exterior of the housing about the at least one objective lens. Each light source set in the plurality of light source sets comprises a first light source that emits light that is substantially limited to a first spectral range and a second light source that emits light that is substantially limited to a second spectral range. Each light source in each light source set in the plurality of light source sets is offset from the at least one objective lens and positioned so that light from each respective light source is backscattered by a tissue of a subject and then passed through the at least one objective lens. Each light in each light source set has a different radial position with respect to the at least one objective lens. The imaging device further comprises a plurality of pixel array photo-sensors within the housing. The imaging device further comprises an optical assembly within the interior of the housing. The optical assembly is in optical communication with the at least one objective lens. The optical assembly is characterized by further directing light received by at least one objective lens from the tissue of a subject to at least one pixel array photo-sensor in the plurality of pixel array photo-sensors. The imaging device further comprises a plurality of multi-bandpass filters (e.g., dual bandpass filters, triple bandpass filters, quad-bandpass filters). Each respective multi-bandpass filter in the plurality of multi-bandpass filters covers a corresponding pixel array photo-sensor in the plurality of pixel array photo-sensors thereby selectively allowing a different corresponding spectral band of light, from the light received by the at least one objective lens and redirected by the optical assembly, to pass through to the corresponding pixel array photo-sensor. The imaging device further comprises a controller. At least one program is non-transiently stored in the controller and executable by the controller. The at least one program causes the controller to perform the method of i) firing a first light in each light source set in the plurality of light source sets for a first period of time while not firing the second light source in each light source set, ii) collecting a first set of images during the first period of time using at least a first subset of the plurality of pixel array photo-sensors, iii) firing a second light in each light source set in the plurality of light source sets for a second period of time while not firing the first light source in each light source set, and iv) collecting a second set of images during the second period of time using at least a second subset of the plurality of pixel array photo-sensors.

In a specific embodiment, the multi-bandpass filters are dual bandpass filters. In some implementations, each respective pixel array photo-sensor in the plurality of pixel array photo-sensors (e.g., optical detectors 112) is covered by a dual-band pass filter (e.g., filters 114).

In some implementations, each respective pixel array photo-sensor is covered by a triple band pass filter, enabling use of a third light source and collection of three sets of images at unique spectral bands. For example, four pixel array photo-sensors can collect images at up to twelve unique spectral bands, when each pixel array photo-sensor is covered by a triple band-pass filter.

In some implementations, each respective pixel array photo-sensor is covered by a quad-band pass filter, enabling use of a fourth light source and collection of four sets of images at unique spectral bands. For example, four pixel array photo-sensors can collect images at up to sixteen unique spectral bands, when each pixel array photo-sensor is covered by a quad band-pass filter. In yet other implementations, band pass filters allowing passage of five, six, seven, or more bands each can be used to collect larger sets of unique spectral bands.

In some embodiments, each respective dual bandpass filter in the plurality of dual bandpass filters is configured to selectively allow light corresponding to either of two discrete spectral bands to pass through to the corresponding photo-sensor. In some embodiments, a first of the two discrete spectral bands corresponds to a first spectral band that is represented in the first spectral range and not in the second spectral range, and a second of the two discrete spectral bands corresponds to a second spectral band that is represented in the second spectral range and not in the first spectral range.

In some embodiments, the optical assembly comprises a plurality of beam splitters in optical communication with the at least one objective lens and the plurality of pixel array photo-sensors. Each respective beam splitter in the plurality of beam splitters is configured to split the light received by the at least one objective lens into at least two optical paths. A first beam splitter in the plurality of beam splitters is in direct optical communication with the at least one objective lens and a second beam splitter in the plurality of beam splitters is in indirect optical communication with the at least one objective lens through the first beam splitter, and the plurality of beam splitters collectively split light received by the at least one objective lens into a plurality of optical paths. Each respective optical path in the plurality of optical paths is configured to direct light to a corresponding pixel array photo-sensor in the plurality of pixel array photo-sensors through the respective multi-bandpass filter covering the corresponding pixel array photo-sensor. In some embodiments, each beam splitter in the plurality of beam splitters exhibits a ratio of light transmission to light reflection of about 50:50. In some embodiments, the beam splitters are wavelength-independent beam splitters. In some embodiments, a first circuit board positioned on a first side of the optical assembly. A first pixel array photo-sensor and a third pixel array photo-sensor in the plurality of pixel array photo-sensors are coupled to the first circuit board, and a second circuit board positioned on a second side of the optical assembly opposite to the first side. The second circuit board is substantially parallel with the first circuit board. A second pixel array photo-sensor and a fourth pixel array photo-sensor in the plurality of pixel array photo-sensors are coupled to the second circuit board. The first beam splitter is configured to split light received from the at least one objective lens into a first optical path and a second optical path. The first optical path is substantially collinear with an optical axis defined by the light incoming from at least one objectives lens to the beam steering element. The second optical path is substantially perpendicular to the optical axis. The second beam splitter is configured split light from the first optical path into a third optical path and a fourth optical path. The third optical path is substantially collinear with the first optical path, and the fourth optical path is substantially perpendicular to the optical axis. A third beam splitter in the plurality of beam splitters is configured to split light from the second optical path into a fifth optical path and a sixth optical path. The fifth optical path is substantially collinear with the second optical path. The sixth optical path is substantially perpendicular to the second optical path, and the optical path assembly further comprises: a first beam steering element configured to deflect light from the third optical path perpendicular to the third optical path and onto the first pixel array photo-sensor coupled to the first circuit board, a second beam steering element configured to deflect light from the fourth optical path perpendicular to the fourth optical path and onto the second pixel array photo-sensor coupled to the second circuit board, a third beam steering element configured to deflect light from the fifth optical path perpendicular to the fifth optical path and onto the third pixel array photo-sensor coupled to the first circuit board, and a fourth beam steering element configured to deflect light from the sixth optical path perpendicular to the sixth optical path and onto the fourth pixel array photo-sensor coupled to the second circuit board. In some embodiments, a first multi-bandpass filter in the plurality of multi-bandpass filters is positioned in the third optical path between the first beam splitter and the first pixel array photo-sensor, a second multi-bandpass filter in the plurality of multi-bandpass filters is positioned in the fourth optical path between the second beam splitter and the second pixel array photo-sensor, a third multi-bandpass filter in the plurality of multi-bandpass filters is positioned in the fifth optical path between the third beam splitter and the third pixel array photo-sensor, and a fourth multi-bandpass filter in the plurality of multi-bandpass filters is positioned in the sixth optical path between the fourth beam splitter and the fourth pixel array photo-sensor. In some embodiments, the imaging device further comprises a polarizing filter disposed along the optical axis. In some embodiments, the polarizing filter is adjacent to the at least one objective lens and before the first beam splitter along the optical axis. In some embodiments, the first beam steering element is a folding prism. In some embodiments, each respective beam splitter and each respective beam steering element is oriented along substantially the same plane. In some embodiments, the first beam splitter, the second beam splitter, and the third beam splitter each exhibits a ratio of light transmission to light reflection of about 50:50.

In some embodiments, the optical assembly comprises a beam steering element that is characterized by a plurality of operating modes, each respective operating mode in the plurality of operating modes causing the beam steering element to be in optical communication with a different pixel array photo-sensor in the plurality of pixel array photo-sensors. A first subset of the plurality of operating modes are associated with firing a first light in each light source set in the plurality of light source set in the first period of time. A second subset of the plurality of operating modes are associated with firing a second light in each light source set in the plurality of light source set in the second period of time. In some embodiments, the imaging device comprises a plurality of beam steering elements, each respective beam steering element configured to direct light in a respective optical path to a respective pixel array photo-sensor, of the plurality of pixel array photo-sensors, corresponding to the respective optical path. In some embodiments, each one of a first subset of the plurality of beam steering elements is configured to direct light in a first direction that is perpendicular to the direction of the light received by the plurality of beam steering elements from the at least one objective lens, and each one of a second subset of the plurality of beam steering elements is configured to direct light in a second direction that is perpendicular to the light received by the plurality of beam steering elements and opposite to the first direction. In some embodiments, the beam steering element comprises a mirror mounted on an actuator, the actuator having the plurality of operating modes. In some embodiments, the mirror is a single-surface mirror. In some embodiments, the mirror is a two-axis micro electro-mechanical (MEMS) mirror. In some embodiments, the beam steering element comprises an array of micromirrors. In some embodiments, the array of micromirrors comprises a digital micromirror device. In some embodiments, the plurality of pixel array photo-sensors comprises at least four pixel array photo-sensors. In some embodiments, each respective pixel array photo-sensor in the plurality of pixel array photo-sensors is used for detecting a different frequency of radiation. In some embodiments, the collecting ii) comprises placing the beam steering element in an operating mode in the plurality of operating modes that causes the beam steering element to be in optical communication with a corresponding pixel array photo-sensor in the plurality of pixel array photo-sensors.

In some embodiments, a housing display is disposed on the exterior of the housing, the housing display in electronic communication with the controller, and the method further comprises displaying an image captured by a respective pixel array photo-sensor in the plurality of pixel array photo-sensors on the housing display.

In some embodiments, the plurality of multi-bandpass filters are dual bandpass filters.

In some embodiments, the plurality of light source sets consist of two light source sets, and a first light source set in the two light source sets is arranged with respect to the at least one objective lens so that the first light source of the first light source set opposes the first light source of the second light source set in the two light source sets. The second light source of the first light source set opposes the second light source of the second light source set.

In some embodiments, the plurality of light source sets consist of four light source sets, and a first light source set in the four light source sets is arranged with respect to the at least one objective lens so that the first light source of the first light source set opposes the first light source of a second light source set in the four light source sets. The second light source of the first light source set opposes the second light source of the second light source set.

In some embodiments, the plurality of light source sets consists of 2N light source sets, where N is a positive integer. A first light source set in the 2N light source sets is arranged with respect to the at least one objective lens so that the first light source of the first light source set opposes the first light source of the second light source set in the 2N light source sets. The second light source of the first light source set opposes the second light source of the second light source set.

In some embodiments, the plurality of light source sets collectively comprises a plurality of first light sources and a plurality of second light sources. The first plurality of first light sources are uniformly radially distributed about the at least one objective lens. The plurality of second light sources are uniformly radially distributed about the at least one objective lens. In some embodiments, light sources in the plurality of first light sources are radially offset from light sources in the plurality of second light sources. In some embodiments the plurality of light source sets consists of three light source sets. In some embodiments, the plurality of light source sets comprises four or more light source sets.

In some embodiments, the first light source of each light source set in the plurality of light source sets is a first multi-spectral light source covered by a first bandpass filter. The first bandpass filter substantially blocks all light emitted by the first light source other than the first spectral range. The second light source of each light source set in the plurality of light source sets is a second multi-spectral light source covered by a second bandpass filter. The second bandpass filter substantially blocks all light emitted by the second light source other than the second spectral range. In some embodiments, the first multi-spectral light source is a first white light emitting diode and the second multi-spectral light source is a second white light emitting diode.

In some embodiments, each respective multi-bandpass filter in the plurality of multi-bandpass filters is configured to selectively allow light corresponding to either of two discrete spectral bands to pass through to the corresponding pixel array photo-sensor. In some embodiments, a first of the two discrete spectral bands corresponds to a first spectral band that is represented in the first spectral range and not in the second spectral range and a second of the two discrete spectral bands corresponds to a second spectral band that is represented in the second spectral range and not in the first spectral range.

In some embodiments, the first spectral range is substantially non-overlapping with the second spectral range. In some embodiments, the first spectral range is substantially contiguous with the second spectral range.

In some embodiments, the first spectral range comprises 520 nm, 540 nm, 560 nm and 640 nm wavelength light and does not include 580 nm, 590 nm, 610 nm and 620 nm wavelength light, and the second spectral range comprises 580 nm, 590 nm, 610 nm and 620 nm wavelength light and does not include 520 nm, 540 nm, 560 nm and 640 nm wavelength light.

In some embodiments, the first set of images includes, for each respective pixel array photo-sensor in the plurality of pixel array photo-sensors, an image corresponding to a first spectral band transmitted by the corresponding multi-bandpass filter, wherein the light falling within the first spectral range includes light falling within the first spectral band of each multi-bandpass filter in the plurality of multi-bandpass filters, and the second set of images includes, for each respective pixel array photo-sensor in the plurality of pixel array photo-sensors, an image corresponding to a second spectral band transmitted by the corresponding multi-bandpass filter. The light falling within the second spectral range includes light falling within the second spectral band of each multi-bandpass filter in the plurality of multi-bandpass filters. In some embodiments, each respective pixel array photo-sensor in the plurality of pixel array photo-sensors is a pixel array that is controlled by a corresponding shutter mechanism that determines an image integration time for the respective pixel array photo-sensor, and a first pixel array photo-sensor in the plurality of pixel array photo-sensors is independently associated with a first integration time for use during the collecting ii) and a second integration time for use during the collecting iv), where the first integration time is independent of the second integration time.

In some embodiments, each image in the plurality of images is a multi-pixel image of the tissue of the subject, and the method further combining each image in the plurality of images, on a pixel by pixel basis, to form a composite image.

In some embodiments, the imaging device is portable and powered independent of a power grid during first period of time and the second period of time, the plurality of light source sets collectively comprises a plurality of first light sources and a plurality of second light sources, the plurality of first light sources collectively provide at least 80 watts of illuminating power during the firing i), the plurality of second light sources collectively provide at least 80 watts of illuminating power during the firing iii), and the imaging device further comprises a capacitor bank in electrical communication with each first light source and each second light source, wherein a capacitor in the capacitor bank has a voltage rating of at least 2 volts and a capacitance rating of at least 80 farads.

In some embodiments, two discrete bands of a multi-bandpass filter in the plurality of multi-bandpass filters are separated by at least 60 nm.

In some embodiments, the imaging device is portable and electrically independent of a power grid during the firing i) and the firing iii), and wherein the firing i) occurs for less than 300 milliseconds and the firing iii) occurs for less than 300 milliseconds.

In some embodiments, the plurality of light source sets collectively comprises a plurality of first light sources and a plurality of second light sources, and each light source in the plurality of first light sources is a white light-emitting diode covered by a respective first light source filter that blocks light emitted by the white light-emitting diode other than the first spectral range. Further, each light source in the plurality of second light sources is a white light-emitting diode covered by a respective second light source filter that blocks light emitted by the white light-emitting diode other than the second spectral range.

In some embodiments, each light source in each light source set is covered by a first polarizer, and the at least one objective lens is covered by a second polarizer.

BRIEF DESCRIPTION OF THE DRAWINGS

So that the present disclosure can be understood in greater detail, a more particular description may be had by reference to the features of various implementations, some of which are illustrated in the appended drawings. The appended drawings, however, merely illustrate the more pertinent features of the present disclosure and are therefore not to be considered limiting, for the description may admit to other effective features and arrangements.

FIG. 5A, FIG. 5B, and FIG. 5C are two-dimensional schematic illustrations of the optical paths 500-506 and 600-606 of implementations of an optical assembly 102 of a hyperspectral imaging device 100.

Figure 1A:
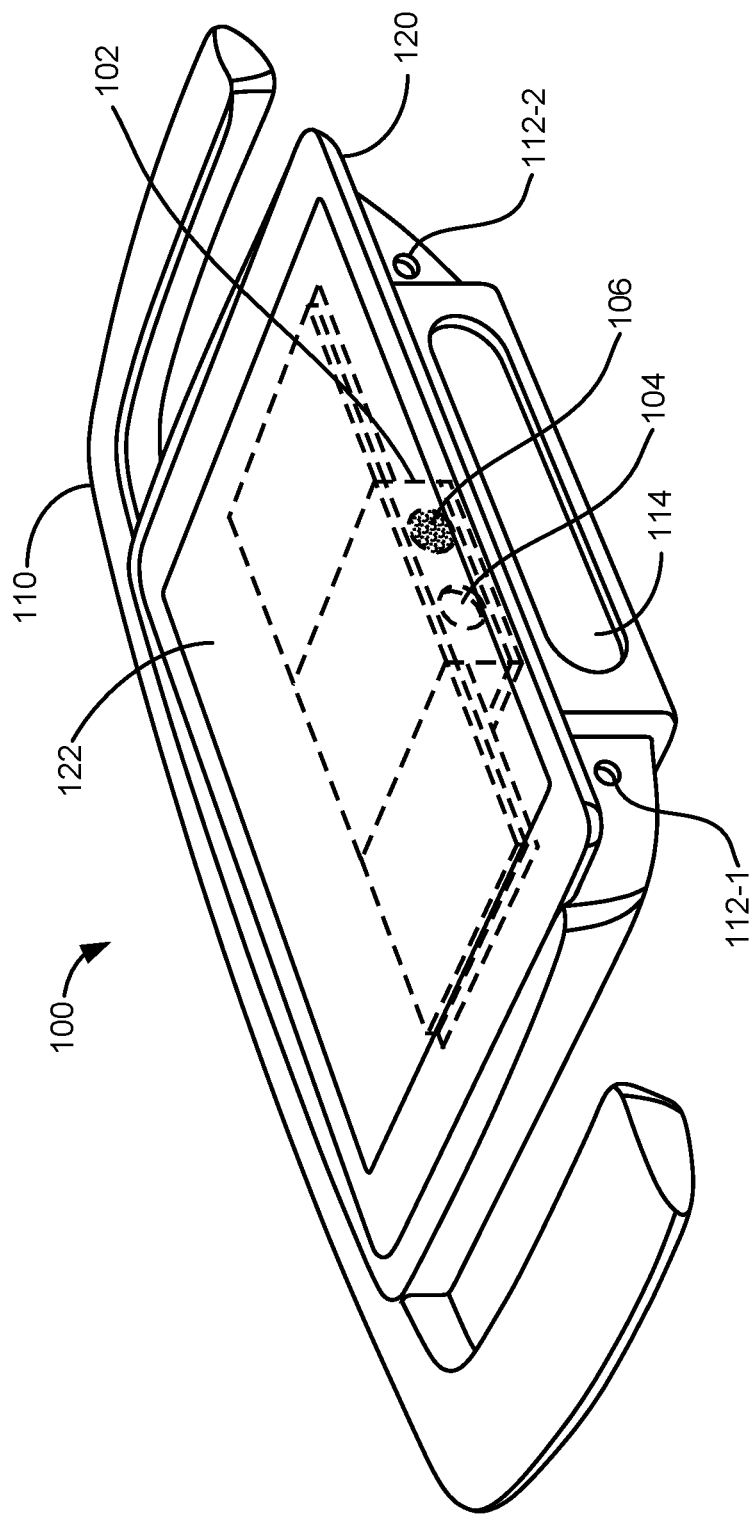
FIG. 1A is an illustration of a hyperspectral imaging device 100, in accordance with an implementation.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example implementations illustrated in the accompanying drawings. However, the invention may be practiced without many of the specific details. And, well-known methods, components, and circuits have not been described in exhaustive detail so as not to unnecessarily obscure more pertinent aspects of the implementations described herein.

Hyperspectral imaging typically relates to the acquisition of a plurality of images, where each image represents a narrow spectral band collected over a continuous spectral range. For example, a hyperspectral imaging system may acquire 15 images, where each image represents light within a different spectral band. Acquiring these images typically entails taking a sequence of photographs of the desired object, and subsequently processing the multiple images to generate the desired hyperspectral image. In order for the images to be useful, however, they must be substantially similar in composition and orientation. For example, the subject of the images must be positioned substantially identically in each frame in order for the images to be combinable into a useful hyperspectral image. Because images are captured sequentially (e.g., one after another), it can be very difficult to ensure that all of the images are properly aligned. This can be especially difficult in the medical context, where a clinician is capturing images of a patient who may move, or who may be positioned in a way that makes imaging the subject area difficult or cumbersome.

As described herein, a hyperspectral imaging device is described that concurrently captures multiple images, where each image is captured in a desired spectral band. Specifically, the disclosed imaging device and associated methods use multiple photo-sensors to capture a plurality of images concurrently. Thus, a user does not need to maintain perfect alignment between the imaging device and a subject while attempting to capture multiple discrete images, and can instead simply position the imaging device once and capture all of the required images in a single operation (e.g., with, one, two, or three exposures) of the imaging device. Accordingly, hyperspectral images can be acquired faster and more simply, and with more accurate results.

Conventional imaging systems also suffer from high power budget demands, requiring the system to be plugged into a power source (e.g., an alternating current outlet) for operation. This arises from the use of tunable filter elements, high powered light sources, etc. Advantageously, the optical architecture of the hyperspectral imaging devices described herein reduces the power burden and overall size of the system, allowing production of a truly portable device.

In one implementation, the design of the hyperspectral imaging devices described herein solve these problems by employing a plurality of photo-sensors configured to concurrently acquire images of an object (e.g., a tissue of a patient) at different spectral bands. Each photo-sensor is configured to detect a limited number of spectral bands (e.g., 1 or 2 spectral bands), but collectively, the plurality of photo-sensors capture images at all of the spectral bands required to construct a particular hyperspectral data cube (e.g., a hyperspectral data cube useful for generating a particular medical diagnosis, performing surveillance, agricultural surveying, industrial evaluation, etc.).

Figure 11:
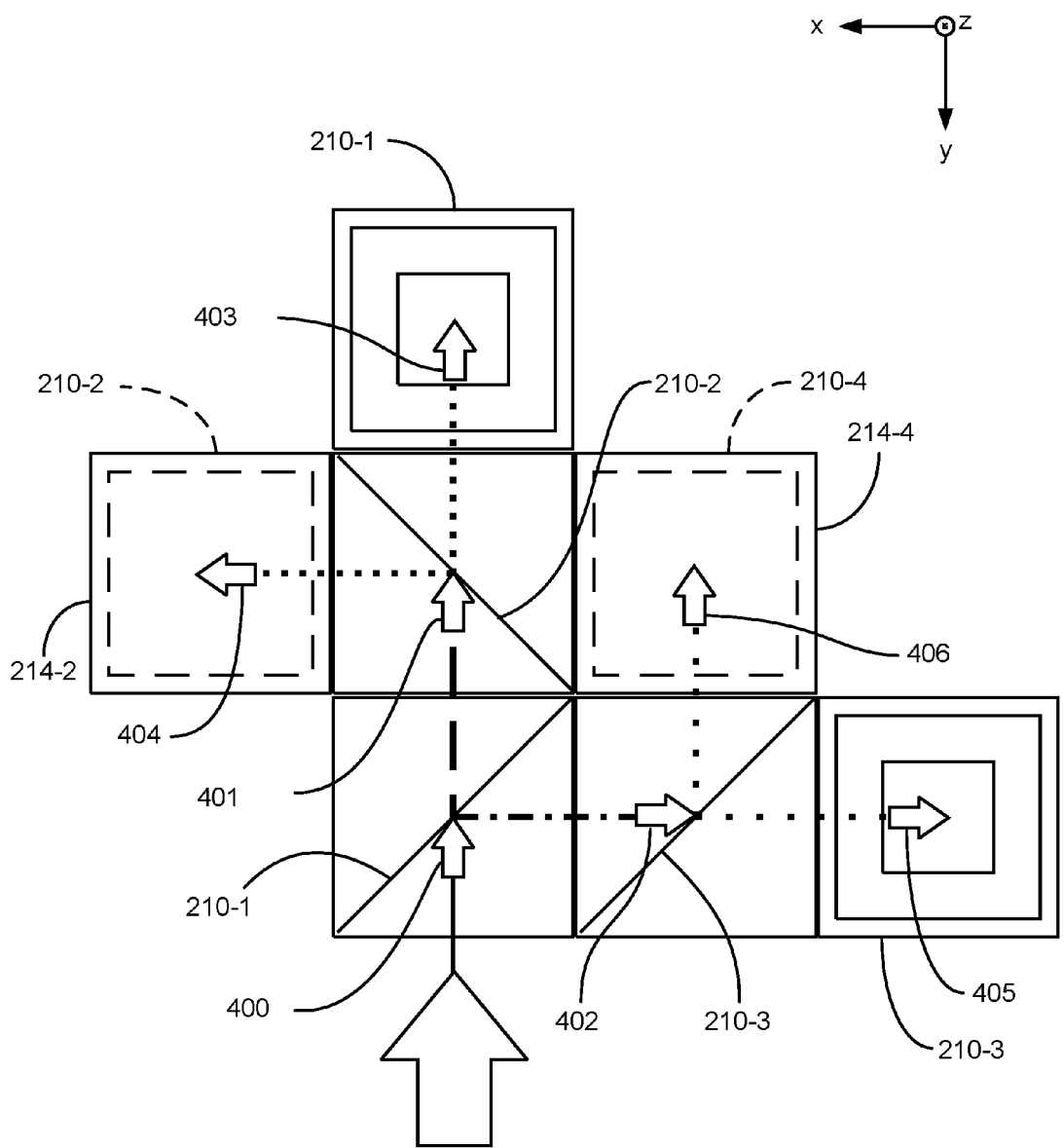
FIG. 11 is a two-dimensional schematic illustration of the optical paths of another implementation of an optical assembly 102 of a hyperspectral imaging device 100.

In some implementations, these advantages are realized by separating and directing light within an optical assembly in the imaging device such that each photo-sensor is irradiated with light of only limited spectral bands. An example of the optical paths created within the optical assembly of such an implementation is illustrated in FIG. 11, which splits light into component spectral bands (e.g., using dichroic beam splitters and/or beam splitting plates) and direct appropriate spectral bands of light to corresponding photo-sensors. In some alternative embodiments, these advantageous are realized by separating and directing light within an optical assembly that is a beam steering device, such as disclosed in U.S. Pat. No. 9,107,624, which is hereby incorporated by reference.

Figure 10:
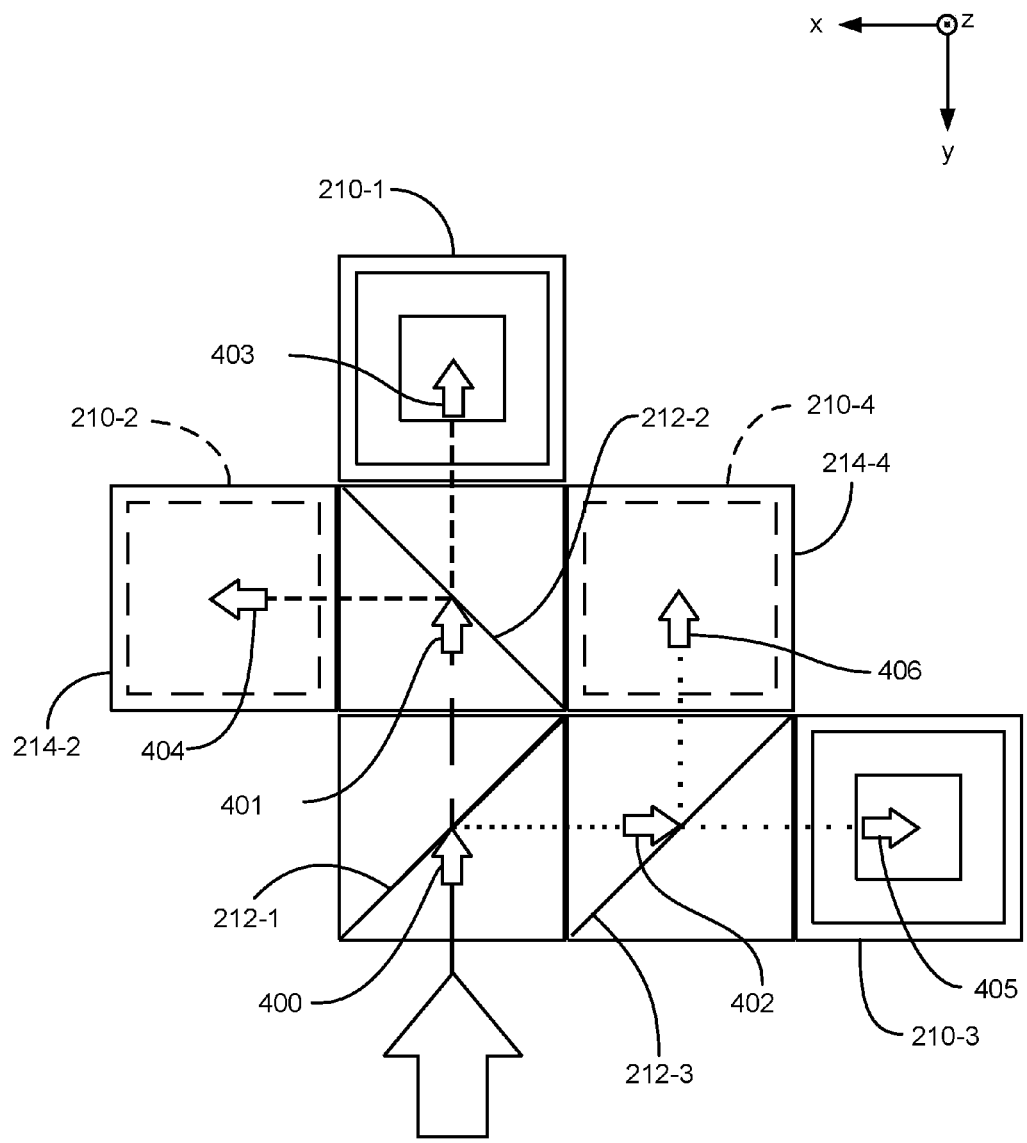
FIG. 10 is a two-dimensional schematic illustration of the optical paths of an implementation of an optical assembly 102 of a hyperspectral imaging device 100.

In some implementations, these advantages are realized by evenly distributing light towards each photo-sensor within an optical assembly, and then filtering out unwanted wavelengths prior to detection by each photo-sensor. An example of the optical paths created within the optical assembly of such an implementation is illustrated in FIG. 10, which uses optical elements (e.g., 50:50 beam splitters) to evenly distribute light towards filter elements covering each respective photo-sensor.

In yet other implementations, these advantages are realized by employing a hybrid of these two strategies. For example, with an optical assembly that first separates light (e.g., with a dichroic beam splitter or beam splitting plate) and then evenly distributes component spectral bands to respective photo-sensors covered by filters having desired passband spectrums.

In some implementations, one or more of these advantages are realized by employing a plurality of light source sets radially disposed on the exterior of a housing about at least one objective lens. Each light source set in the plurality of light source sets comprises a first light source that emits light that is substantially limited to a first spectral range and a second light source that emits light that is substantially limited to a second spectral range. Each light source in each light source set in the plurality of light source sets is offset from the at least one objective lens and positioned so that light from each respective light source is backscattered two illumination sources in the hyperspectral imaging device. Thus, each first illumination source in each light source set is configured to illuminate an object with a first sub-set of spectral bands, and each second illumination source in each light source set is configured to illuminate the object with a second sub-set of spectral bands. The first and second subsets of spectral bands do not overlap, but together include all the spectral bands required to construct a particular hyperspectral data cube. The optical assembly is configured such that two sets of images are collected, the first while the object is illuminated with each first light source in the plurality of light source sets and the second while the object is illuminated with each second light source in the plurality of light source sets. For example, each photo-sensor captures a first image at a first spectral band included in the first sub-set of spectral bands and a second image at a second spectral band included in the second sub-set of spectral bands.

In some implementations, image capture and processing includes the imaging device collecting a plurality of images of a region of interest on a subject (e.g., a first image captured at a first spectral bandwidth and a second image captured at a second spectral bandwidth). The imaging device stores each respective image at a respective memory location (e.g., the first image is stored at a first location in memory and the second image is stored at a second location in memory). And the imaging device compares, on a pixel-by-pixel basis, e.g., with a processor 210, each pixel of the respective images to produce a hyperspectral image of the region of interest of the subject. In some implementations, individual pixel values are binned, averaged, or otherwise arithmetically manipulated prior to pixel-by-pixel analysis, e.g., pixel-by-pixel comparison includes comparison of binned, averaged, or otherwise arithmetically manipulated pixel values.

Exemplary Implementations

FIG. 1A illustrates a hyperspectral imaging device 100, in accordance with various implementations. The hyperspectral imaging device 100 includes an optical assembly 102 having at least one light source 106 for illuminating the surface of an object (e.g., the skin of a subject) and a lens assembly 104 for collecting light reflected and/or back scattered from the object. The optical assembly 102 is mounted onto a docking station 110.

In various implementations, optical assembly 102 is permanently fixed onto the docking station 110 (e.g., optical assembly 102 is held in place by a substructure of docking station 110 partially encasing optical assembly 102 and fastened through welding, screws, or other means). In other implementations, optical assembly 102 is not permanently fixed onto the docking station 110 (e.g., optical assembly 102 snaps into a substructure of docking station 110).

In various optional implementations, and with reference to FIG. 1A, docking station 110 includes first and second projectors 112-1 and 112-2 configured to project light onto the object indicating when the hyperspectral imaging device 100 is positioned at an appropriate distance from the object to acquire a focused image. This may be particularly useful where the lens assembly (at least one objective lens) 104 has a fixed focal distance, such that the image cannot be brought into focus by manipulation of the lens assembly.

Figure 8A:
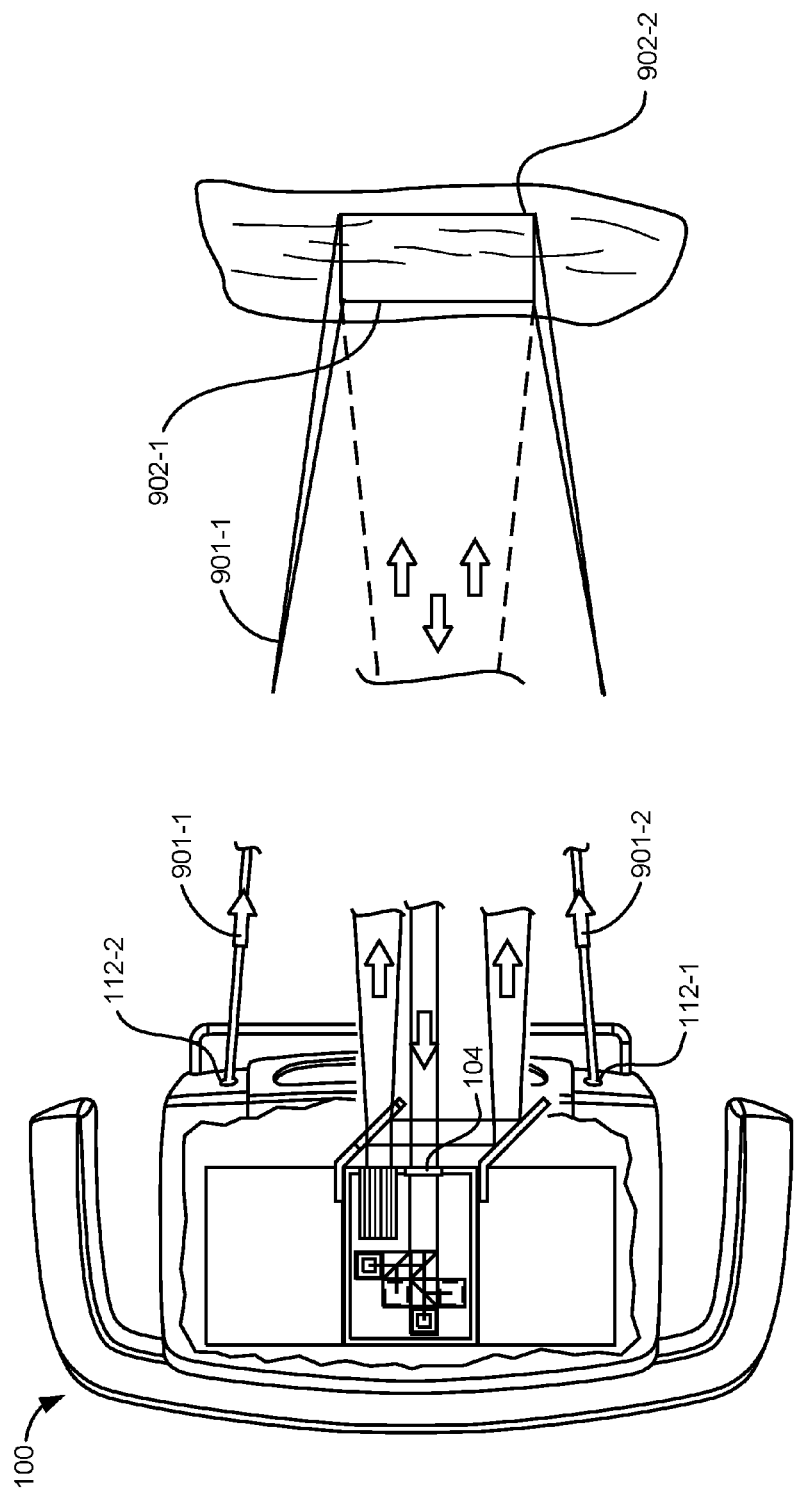
FIG. 8A is a partially cut-out illustration of a bottom view of a hyperspectral imaging device 100 and optical paths, in accordance with an implementation.
Figure 9A:
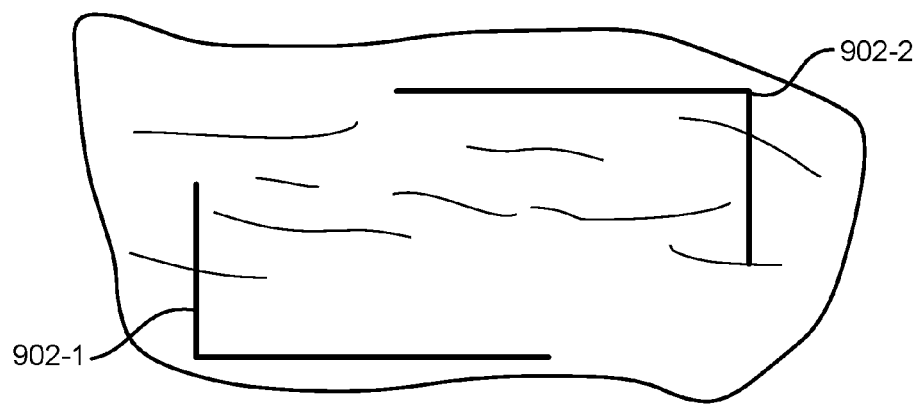
FIG. 9A, FIG. 9B and FIG. 9C are illustrations of framing guides 902 projected onto the surface of an object for focusing an image collected by implementations of a hyperspectral imaging device 100.
Figure 9B:
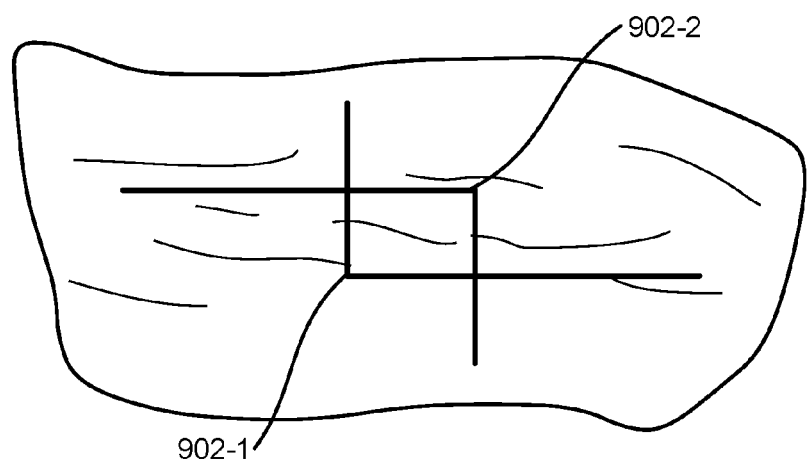
Figure 9C:
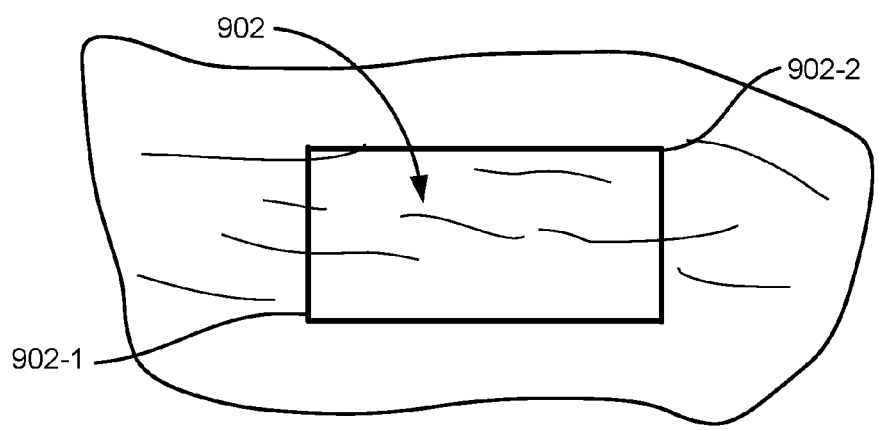

Referring additionally to FIGS. 8A and 9C, in various implementations, first projector 112-1 and second projector 112-2 of FIG. 1A are configured to project patterns of light onto the to-be-imaged object including a first portion 902-1 and a second portion 902-2 that together form a shape 902 on the object when properly positioned (see, e.g., FIGS. 8A and 9C). For example, the first portion of the shape 902-1 and the second portion of the shape 902-1 are configured to converge to form the shape 902 when the lens 104 is positioned at a predetermined distance from the object, the predetermined distance corresponding to a focal distance of the lens assembly 104.

Figure 8B:
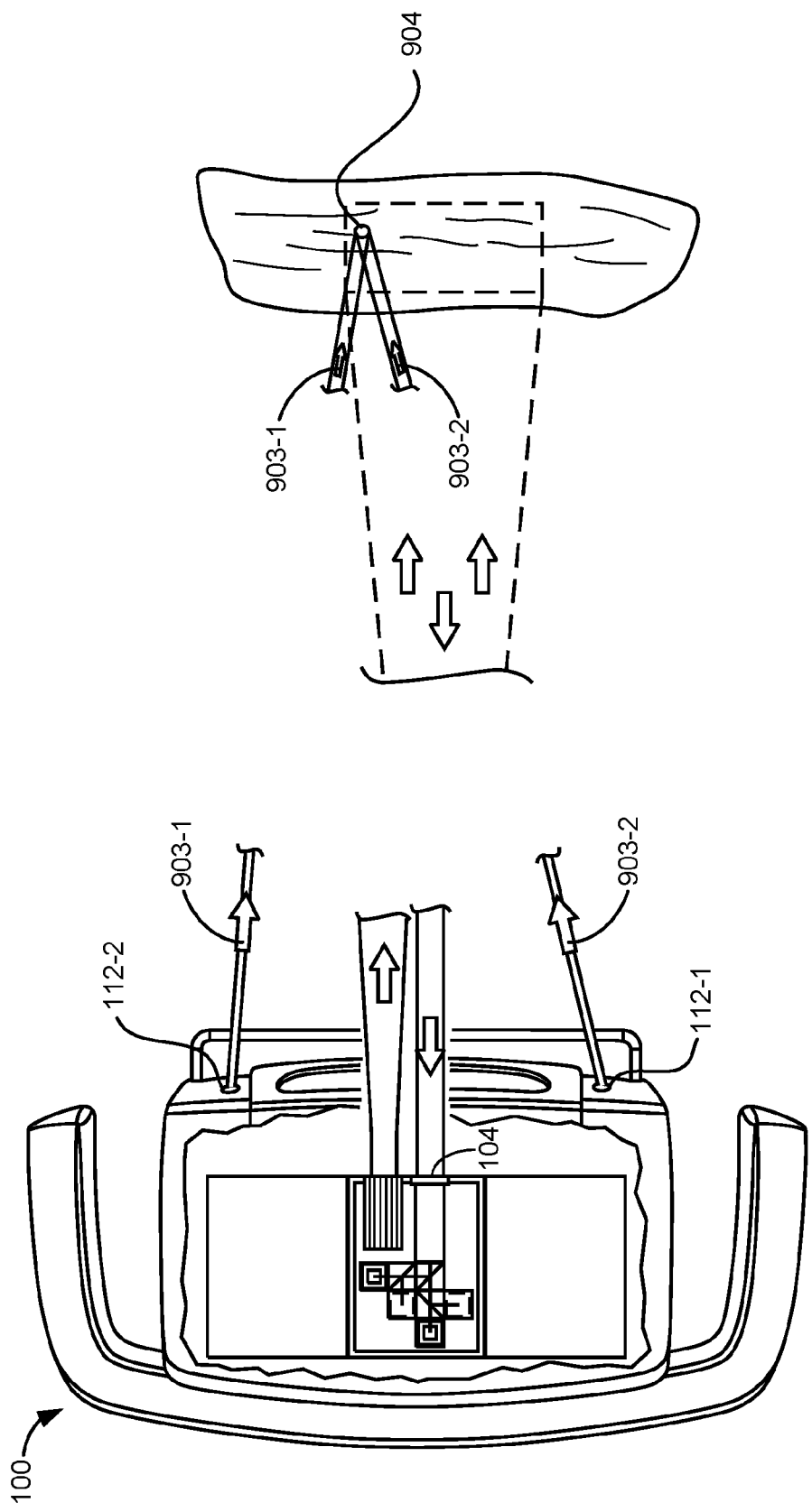
FIG. 8B is a partially cut-out illustration of a bottom view of a hyperspectral imaging device 100 and optical paths, in accordance with another implementation.
Figure 9D:
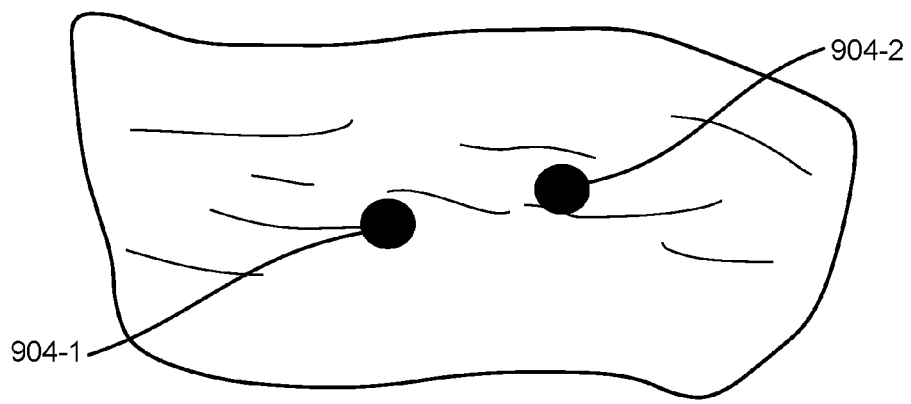
FIGS. 9D and 9E are illustrations of point guides 903 projected onto the surface of an object for focusing an image collected by implementations of a hyperspectral imaging device 100.
Figure 9E:
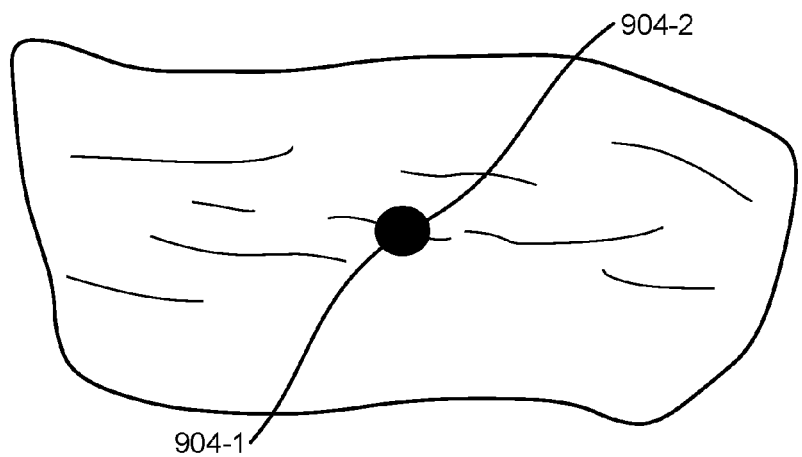

In various implementations, first projector 112-1 and second projector 112-2 are each configured to project a spot onto the object, such that the spots converge when the lens 104 is positioned at a predetermined distance from the object corresponding to a focus distance of the lens (see, e.g., FIGS. 8B and 9E). Other projections are also contemplated, including other shapes, reticles, images, crosshairs, etc.

Returning to FIG. 1A, in various implementations, docking station 110 includes an optical window 114 configured to be positioned between light source 106 and an object to be imaged. Window 114 is also configured to be positioned between lens assembly 104 and the object to be imaged. Optical window 114 protects light source 106 and lens assembly 104, as well as limits ambient light from reaching lens assembly 104. In various implementations, optical window 114 consists of a material that is optically transparent (or essentially optically transparent) to the wavelengths of light emitted by light source 106. In various implementations, optical window 114 consists of a material that is partially or completely opaque to one or more wavelengths of light not emitted by light source 106. In various implementations, optical window 114 serves as a polarizing lens. In various implementations, optical window 114 is open to the external environment (e.g., does not include an installed lens or other optically transparent material).

In various implementations, docking station 110 is configured to receive a mobile device 120, such as a smart phone, a personal digital assistant (PDA), an enterprise digital assistant, a tablet computer, an IPOD, a digital camera, a portable music player, and/or other portable electronic devices, effectively mounting the mobile device onto hyperspectral imaging device 100. In various implementations, docking station 110 is configured to facilitate electronic communication between optical assembly 102 and mobile device 120. In various implementations, mobile device 120 includes display 122 configured to act as a display for optical assembly 102 (e.g., as a touch screen display for operating optical assembly 102 and/or as a display for hyperspectral images collected by optical assembly 102). In various implementations, mobile device 120 is configured as a processor for processing one or more images collected by optical assembly 102. In various implementations, mobile device 120 is configured to transmit one or more images collected by optical assembly 102 to an external computing device (e.g., by wired or wireless communication).

Figure 1B:
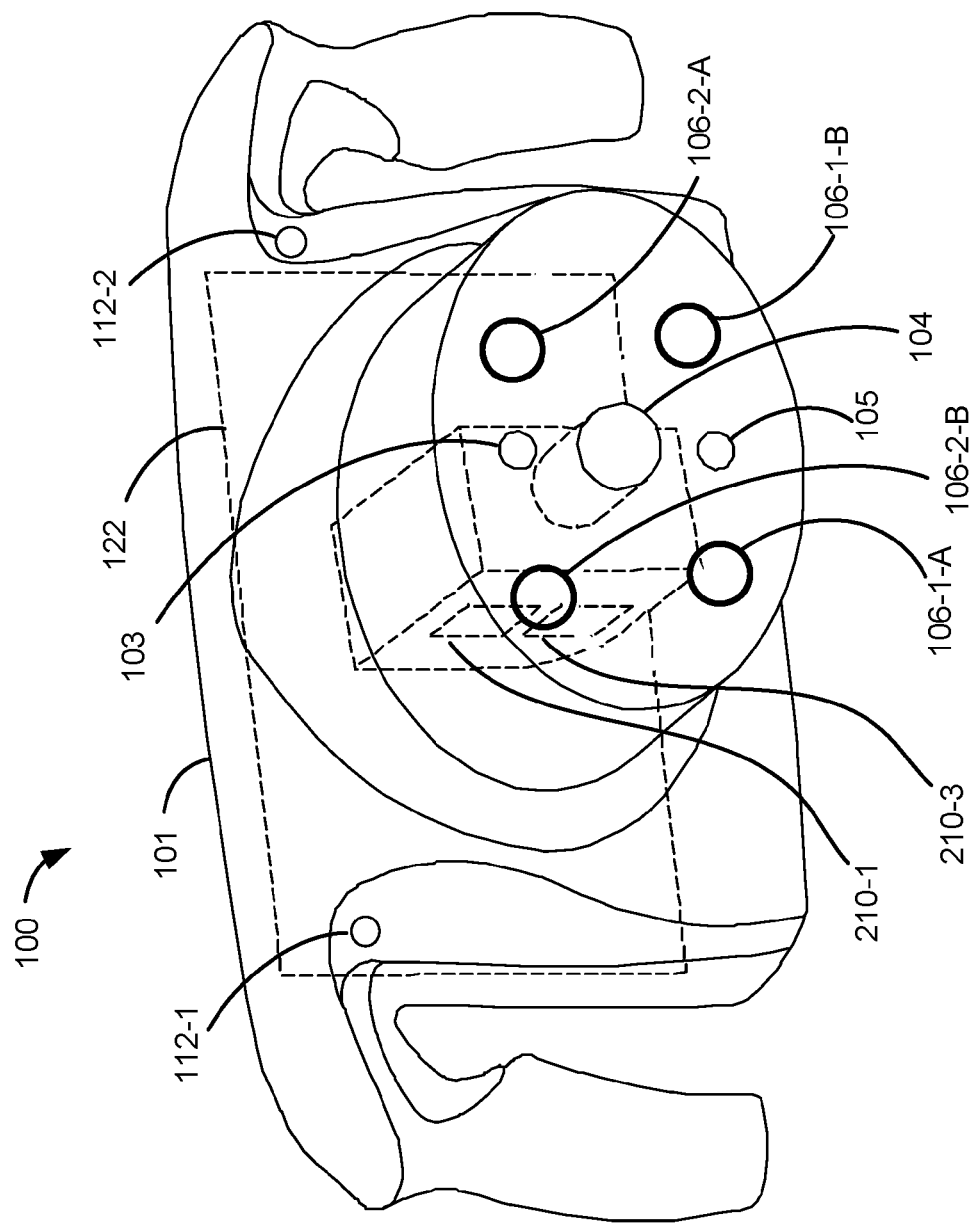
FIG. 1B is an illustration of a hyperspectral imaging device 100, in accordance with an implementation.

FIG. 1B illustrates another hyperspectral imaging device 100, in accordance with various implementations, similar to that shown in FIG. 1A but including an integrated body 101 (housing) that resembles a digital single-lens reflex (DSLR) camera in that the body has a forward-facing objective lens assembly 104, and a rearward facing display 122. The DSLR-type housing allows a user to easily hold hyperspectral imaging device 100, aim it toward a patient and the region of interest (e.g., the skin of the patient), and position the device at an appropriate distance from the patient. One will appreciate that the implementation of FIG. 1B, may incorporate the various features described above and below in connection with the device of FIG. 1A.

In various implementations, and similar to the device described above, the hyperspectral imaging device 100 illustrated in FIG. 1B includes a plurality of light source sets 106 radially disposed on the exterior of the housing about the objective lens 104. In FIG. 1B, the plurality of light sets consists of two light sets for a total of four light sources. Each light source set 106 in the plurality of light source sets comprises a first light source (106-1-A, 106-2-A of FIG. 1B) that emits light that is substantially limited to a first spectral range and a second light source (106-1-B, 106-2-B of FIG. 1B) that emits light that is substantially limited to a second spectral range. As illustrated in FIG. 1B, each light source in each light source set in the plurality of light source sets is offset from the at least one objective lens 104 and positioned so that light from each respective light source is backscattered by a tissue of a subject (not shown) and then passed through the at least one objective lens 104. As illustrated in FIG. 1B, each light (106-1-A, 106-1-B, 106-2-A, 106-2-A) in each light source set has a different radial position with respect to the at least one objective lens 104. As such, light source sets 106 are for illuminating the surface of an object (e.g., the skin of a subject) and the at least one objective lens 104 is for collecting light reflected and/or back scattered from the object.

In various implementations, and also similar to the device described above, the hyperspectral imaging device of FIG. 1B includes first and second projectors 112-1 and 112-2 configured to project light onto the object indicating when the hyperspectral imaging device 100 is positioned at an appropriate distance from the object to acquire a focused image. As noted above, this may be particularly useful where the at least one objective lens 104 has a fixed focus distance, such that the image cannot be brought into focus by manipulation of the lens assembly. As shown in FIG. 1B, the projectors are mounted on a forward side of body 101.

In various implementations, the body 101 substantially encases and supports the plurality of light sources 106 and the lens assembly 104 of the optical assembly, along with the first and second projectors 112-1 and 112-2 and the display 122.

In contrast to the above-described device, various implementations of the hyperspectral imaging device of FIG. 1B include photo-sensors mounted on substantially vertically-oriented circuit boards (see, e.g., photo sensors 210-1, 210-3). In various implementations, the hyperspectral imaging device includes a live-view camera 103 and a remote thermometer 105. The live-view camera 103 enables the display 122 to be used as a viewfinder, in a manner similar to the live preview function of DSLRs. The thermometer 105 is configured to measure the temperature of the patient's tissue surface within the region of interest.

Figure 2A:
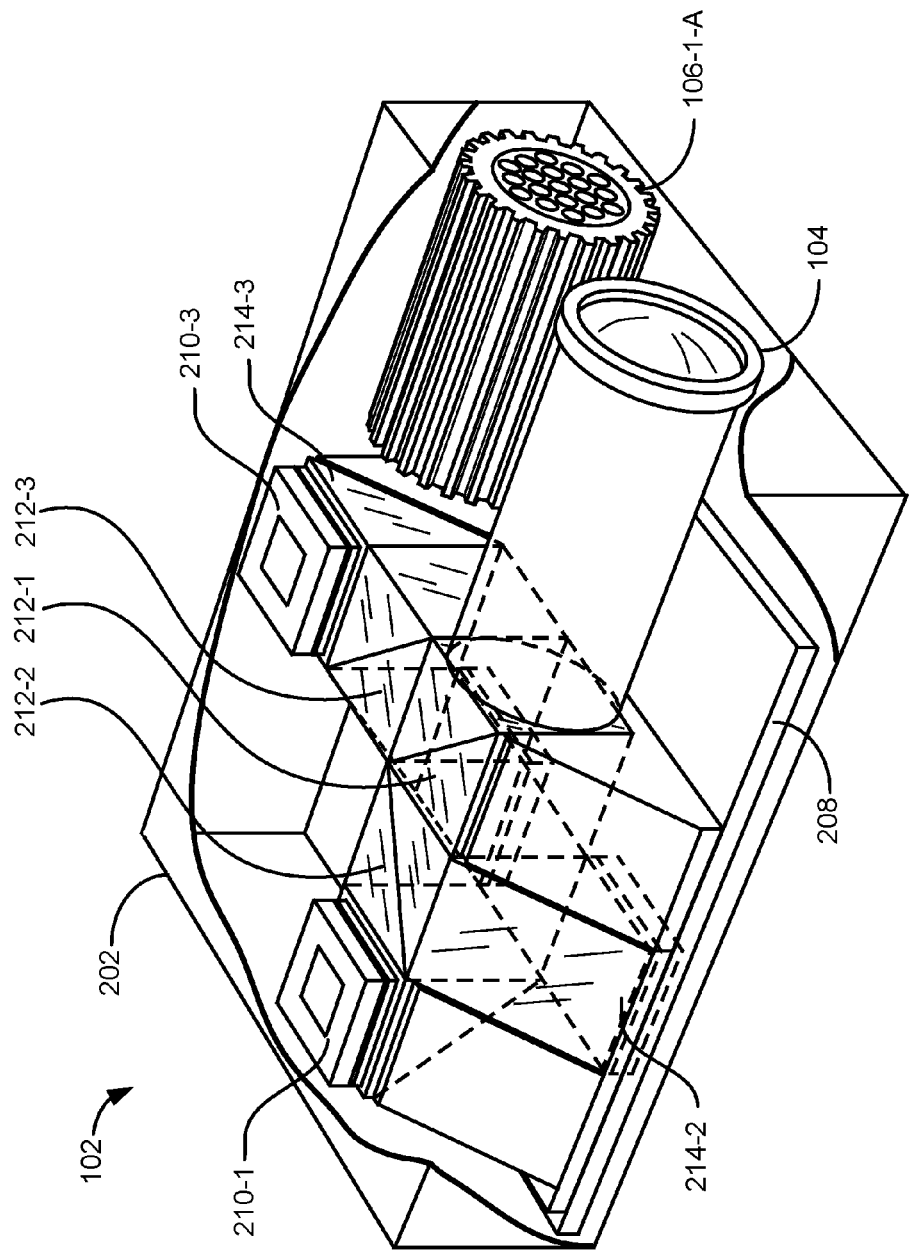
FIG. 2A and FIG. 2B are illustrations of an optical assembly 102 of a hyperspectral imaging device 100, in accordance with implementations of the disclosure.

FIG. 2A is a cutaway view of the optical assembly 102 for a hyperspectral imaging device 100, in accordance with various implementations. The optical assembly 102 may be incorporated into a larger assembly (as discussed herein), or used independently of any other device or assembly.

As shown in FIG. 2A, the optical assembly 102 includes a casing 202. As also shown in an exploded view in FIG. 3, the optical assembly 102 also includes at least one objective lens 104 and provides spacing for individual light sources (e.g., 106-1-A) in the plurality of sets of light sources 106, an optical path assembly 204, one or more circuit boards (e.g., circuit board 206 and circuit board 208), and a plurality of photo-sensors 210 (e.g., photo-sensors 210-1 . . . 210-4). One will appreciate that the imaging device 100 is provided with one or more processors and a memory, referred to herein as a controller. For example, such controllers may be integrated or operably coupled with the one or more circuit boards. For instance, in some embodiments, an AT32UC3A364 (ATMEL corporation, San Jose Calif.) microcontroller, or equivalent, coupled to one or more floating point gate arrays, is used as a controller to collect images from the pixel array photo-sensors. Although illustrated with two circuit boards 206 and 208, in some implementations, the hyperspectral imaging device has a single circuit board (e.g., either 206 or 208) and each pixel array photo-sensor 210 is either mounted on the single circuit board or connected to the circuit board (e.g., by a flex circuit or wire).

Components of the optical assembly 102 are housed in and/or mounted to the casing 202. In various implementations, the casing 202 is itself configured to be housed in and/or mounted to another assembly, as shown in FIG. 1A.

The lens assembly 104 (also referred to interchangeably herein as a "lens" or "at least one objective lens") is an imaging lens that is configured to capture light reflected from objects, focus the light, and direct the light into the optical path assembly 204. In various implementations, the lens assembly 104 is a multi-element lens having a fixed focal length, a fixed focus distance, and/or is a fixed-focus lens.

The plurality of light source sets 106 are configured to direct light onto an object to be imaged by the optical assembly 102. Specifically, the plurality of light source sets is configured to illuminate an object with light having desired spectral content. Light from the plurality of light source sets is reflected or backscattered from the object and is then received by the lens assembly 104 and captured by the plurality of pixel array photo-sensors in the optical assembly 102.

In various implementations, as discussed herein, the plurality of light source sets is configured to operate according to two or more modes of operation, where each mode of operation results in the illumination of the object with light having different spectral content. For example, referring to FIG. 1A, in a first mode of operation, a first light in each light source set 106 in the plurality of light source sets is fired for a first period of time while not firing the second light source in each light source set. So, in the example of FIG. 1A, light 106-1-A and light 106-2-A are fired for a first period of time while not firing light 106-1-B and light 106-2-B. In some embodiments, the first light in each light source set emits light within a spectral range of 500 nm to 600 nm (or any other appropriate spectral range). A first set of images is collected during the first period of time using at least a first subset of the plurality of pixel array photo-sensors. Next, in a second mode of operation, the second light in each light set is fired thereby emitting light within a spectral range of 600 nm to 700 nm (or any other appropriate spectral range) for a second period of time while not firing the first light source in each light source set. So, in the example of FIG. 1A, light 106-1-B and light 106-2-B are fired for a second period of time while not firing light 106-1-A and light 106-2-A. A second set of images is collected during the second period of time using at least a second subset of the plurality of pixel array photo-sensors.

In various implementations, the each light source in each light source set includes a single broadband light source, a plurality of broadband light sources, a single narrowband light source, a plurality of narrowband light sources, or a combination of one or more broadband light source and one or more narrowband light source. Likewise, in various embodiments, each light source in each light source set includes a plurality of coherent light sources, a single incoherent light source, a plurality of incoherent light sources, or a combination of one or more coherent and one or more incoherent light sources.

In one implementation, where a light source set is configured to emit light within two or more spectral ranges, the light source set includes two or more light sources (e.g., each respective light source include one or more light emitting devices configured to emit light of the same spectral band), where each respective light source is configured to only emit light within one of the two or more spectral ranges. In some embodiments, referring to FIG. 1B, where a light source set is configured to emit light within two or more spectral ranges, the light source set includes two or more light sources (e.g., light emitting diodes), where each respective light source is filtered by a respective filter (e.g., a bandpass filter). As a specific example, referring to FIG. 1B, light source set 106 comprises light source 106-1-A that is configured to emit light within a first spectral range and light source 106-1-B that is configured to emit light within a second spectral range. In some embodiments, light source 106-1-A comprises a first set of light emitting devices that are filtered with a first bandpass filter corresponding to the first spectral range, and light source 106-1-B comprises a second set of light emitting devices filtered with a second bandpass filters corresponding to the second spectral range. In typical embodiments the first spectral range is different from, and non-overlapping, the first second spectral range. In some embodiments the first spectral range is different from, but overlapping, the second spectral range. In some embodiments the first spectral range is the same as the second spectral range.

In some embodiments, the first light source (e.g., 106-1-A) of a light source set 106 consists of a first single light emitting diode (LED) and the second light source (e.g., 106-1-B) of the light source set consists of a consists of a second single light emitting diode. An example of a suitable light emitting diode for use as the first single light emitting diode and the second single light emitting diode in such embodiments is a LUMINUS CBT-140 Whtie LED (Luminus Devices, Inc., Billerica, Mass.).

In some embodiments, the first light source (e.g., 106-1-A) of a light source set 106 consists of a first set of light emitting diodes and the second light source (e.g., 106-1-B) of the light source set consists of a second set of light emitting diodes. In some embodiments, the first set of light emitting devices consists of a first plurality of light emitting diode and the second set of light emitting devices consists of a second plurality of light emitting diodes.

In some embodiments each first light source in each light source set 106 is not covered by a bandpass filter and natively emits only the first spectral range. In some embodiments each second light source in each light source set 106 is not covered by a bandpass filter and natively emits only the second spectral range. In some embodiments, each first light source in each light source set 106 emits at least 80 watts of illuminating power and each second light source in each second light source set emits at least 80 watts of illuminating power. In some embodiments, the plurality of light source sets 106 collectively comprises a plurality of first light sources and a plurality of second light sources, the plurality of first light sources collectively provide at least 80 watts of illuminating power when fired and the plurality of second light sources collectively provide at least 80 watts of illuminating power when fired. In some embodiments, the plurality of first light sources collectively provide at least 80 watts, at least 85 watts, at least 90 watts, at least 95 watts, at least 100 watts, at least 105 watts, or at least 110 watts of illuminating power when fired. In some embodiments, the plurality of second light sources collectively provide at least 80 watts, at least 85 watts, at least 90 watts, at least 95 watts, at least 100 watts, at least 105 watts, or at least 110 watts of illuminating power when fired. In some embodiments, the spectral imager 100 is not connected to a main power supply (e.g., an electrical power grid) during illumination. In other words, in some embodiments, the spectral imager is independently powered, e.g. by a battery, during at least the illumination stages. In some embodiments, in order to achieve the amount of illuminating power needed by the plurality of light source sets 106 (e.g., more than 100 watts of illuminating power in some embodiments), the light sources are in electrical communication to the battery through a high performance capacity bank (not shown). In one such example, the capacitor bank comprises a board mountable capacitor. In one such example, the capacitor bank comprises a capacitor having a rating of at least 80 farads (F), a peak current of at least 80 amperes (A), and is capable of delivering at least 0.7 watt-hours (Whr) of energy during illumination. In one such example, the capacitor bank comprises a capacitor having a rating of at least 90 F, a peak current of at least 85 A, and is capable of delivering at least 0.8 Whr of energy during illumination. In one such example, the capacitor bank comprises a capacitor having a rating of at least 95 F, a peak current of at least 90 A, and is capable of delivering at least 0.9 Whr of energy during illumination. In one such example, the capacitor bank comprises an RSC2R7107SR capacitor (IOXUS, Oneonta, N.Y.), which has a rating of 100 F, a peak current of 95 A, and is capable of delivering 0.1 Whr of energy during illumination.

In one example, the battery used to power the spectral imager, including the capacitor bank, has a voltage of at least 6 volts and a capacity of at least 5000 mAH. In one such example, the battery is manufactured by TENERGY (Fremont, Calif.), is rated for 7.4 V, has a capacitance of 6600 mAH, and weighs 10.72 ounces.

In some embodiments, the capacitor bank comprises a single capacitor in electrical communication with both the light source 106 and the light source 107, where the single capacitor has a rating of at least 80 F, a peak current of at least 80 A, and is capable of delivering at least 0.7 Whr of energy during illumination. In some embodiments, the capacitor bank comprises a first capacitor in electrical communication with the light source 106 and a second capacitor in electrical communication with light source 107, where the first capacitor and the second capacitor each have a rating of at least 80 F, a peak current of at least 80 A, and are each capable of delivering at least 0.7 Whr of energy during illumination.

In one implementation, where the plurality of light sources are configured to emit light within two or more spectral ranges, in a first mode of operation, only the first light source in each respective light source set is fired (e.g., 106-1-A, 106-2-A, . . . , 106-N-A, where N is a positive integer), and in a second mode of operation, only the second light source in each respective light source set is fired (e.g., 106-1-B, 106-2-B, . . . , 106-N-B, wherein N is a positive integer). Here, it will be understood that each first light source in the plurality of light sets is a single first LED and each second light source in the plurality of light sources is a single second LED in some embodiments. The same or a similar arrangement of light emitting devices and bandpass filters may be used in other light sources of the imaging device 100. Of course, additional modes of operations (e.g., a third mode of operation, a fourth mode of operation, etc.) are also possible by including additional lights and/or additional bandpass filters corresponding to additional spectral ranges.

Figure 2B:
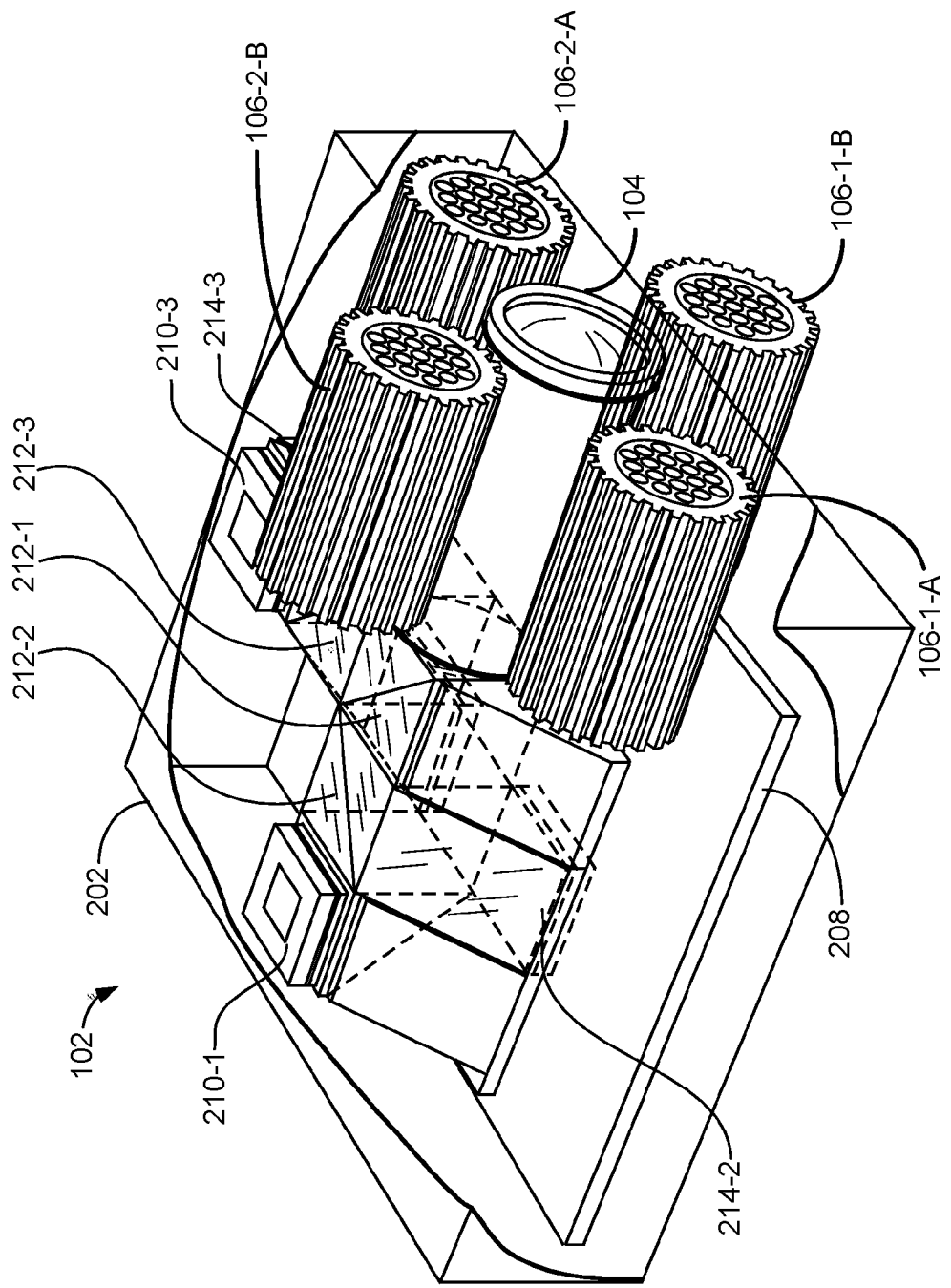

In various implementations, as shown in FIG. 2B, the imaging device has two light source sets 106 each consisting of a light source 106-N-A and a light source 106-N-B. As illustrated in FIG. 2B, N=2. In various embodiments not illustrated in FIG. 2B, the imaging device has one light source set, three light source sets, or more than three light source sets. In various implementations, each light source set is configured to emit light falling within two substantially non-overlapping spectral ranges. For example, in a first mode of operation, a light source 106-1-A and a light source 106-2-A emit light within a spectral range of 500 nm to 600 nm (or any other appropriate spectral range), and in a second mode of operation light sources 106-1-B and 106-2-B emit light within a spectral range of 600 nm to 700 nm (or any other appropriate spectral range). In some embodiments as illustrated in FIG. 2B, light sources 106-1-A and 106-2-A are on opposite sides of the objective lens 104 in order to reduce shadowing artifacts on the target object. Further, light sources 106-1-B and 106-2-B are also on opposite sides of the objective lens 104 in order to also reduce shadowing artifacts on the target object.

In some implementations where the hyperspectral imaging device includes a plurality of light source sets where each such light source set has two different types of light sources (e.g., light sources 106-N-A and 106-N-B, where N is a positive integer), each light source type is configured to emit light falling within only one of the two substantially non-overlapping spectral ranges. For example, in a first mode of operation, light sources 106-N-A emit light within a first spectral range (e.g., 500 nm to 600 nm, or any other appropriate spectral range), and in a second mode of operation, light sources 106-N-B emit light within a second spectral range (e.g., 600 nm to 700 nm, or any other appropriate spectral range), where N is a positive integer.

In some implementations where the hyperspectral imaging device includes a plurality of light source sets and each such light source set has two types of light sources (e.g., light sources 106-N-A and 106-N-B, where N is a positive integer), each light source type is configured to emit light falling within a corresponding predetermined spectral range. For example, in a first mode of operation, light sources 106-N-A emit light within a first spectral range (e.g., one that encompasses 520 nm, 540 nm, 560 nm and 640 nm light), and in a second mode of operation, light sources 106-N-B emit light within a second spectral range (e.g. one that encompasses 580 nm, 590 nm, 610 nm and 620 nm light), where N is a positive integer.

In some embodiments the first and second modes of light operation apply to light source sets. In other words, while each respective light source only emits light falling within one respective spectral range, each light source set collectively operates according to the first and the second modes of operation described above.

In various implementations, one or both of the two substantially non-overlapping spectral ranges are non-contiguous spectral ranges. For example, each first light source of the plurality of light source sets may emit light having wavelengths between 490 nm and 580 nm in a discontinuous fashion (e.g., in spectral bands of 490-510 nm and 520-580 nm), and each second light source of the plurality of light source sets may emit light having wavelengths between 575 nm and 640 in a continuous fashion (e.g., in a single spectral band of 575-640 nm). In another example, each first light source of the plurality of light source sets may emit light having wavelengths between 510 nm and 650 nm in a discontinuous fashion (e.g., in spectral bands of 510-570 nm and 630-650 nm), and each second light source in the plurality of light source sets may emit light having wavelengths between 570 nm and 630 in a continuous fashion (e.g., in a single spectral band of 570-630 nm). In still another example, each first light source in the plurality of light source sets may emit light having wavelengths between 515 nm and 645 nm in a discontinuous fashion (e.g., in spectral bands of 515-565 nm and 635-645 nm), and each second light source in the plurality of light source sets may emit light having wavelengths between 575 nm and 625 in a continuous fashion (e.g., in a single spectral band of 575-625 nm).

In some implementations, each light source in the plurality of light source sets is a broadband light source (e.g., white LEDs) with each first light source in the plurality of light sources being covered by a different first wavelength filter whereas and each second light source in the plurality of light source sets being covered by a second wavelength filter, where the first and second wavelength filters have substantially overlapping pass bands.

In some implementations, each light source in the plurality of light source sets is a broadband light source (e.g., white LEDs) and each first light source in the plurality of light source sets is covered by a corresponding first wavelength filter whereas each second light source in the plurality of light source sets is covered by a second wavelength filter, where the first and second wavelength filters have substantially non-overlapping pass bands. The pass bands of filters used in such implementations are based on the identity of the spectral bands to be imaged for creation of the hyperspectral data cube.

In one implementation, the spectral bands to be collected are separated into two groups. The first group consists of spectral bands with wavelengths below a predetermined wavelength and the second group consists of spectral bands with wavelengths above a predetermined wavelength. For example, if images at eight spectral bands are needed to create a particular hyperspectral data cube, the four spectral bands having the shortest wavelengths make up the first group and the other four spectral bands make up the second group. The first pass band is then selected such that the first filter allows light having wavelengths corresponding to the first group, but blocks substantially all light having wavelengths corresponding to the second group. Likewise the second pass band is selected such that the second filter allows light having wavelengths corresponding to the second group, but blocks substantially all light having wavelengths corresponding to the first group.

In another implementation, the spectral bands to be collected are separated into two groups. The first group consists of a first subset of spectral bands and the second group consists of a second subset of spectral bands. In this implementation, the division into the two subsets is made in such a manner that, upon pairing a spectral band from the first subset with a spectral band from the second subset, a minimum predetermined band separation is guaranteed. For instance, in one embodiment the first subset comprises 520 nm, 540 nm, 560 nm, and 640 nm whereas the second subset comprises 580 nm, 590 nm, 510 nm and 620 nm wavelengths. Moreover, four pairs of wavelengths are formed, each pair comprising one band from the first subset and one band from the second subset, where the minimum separation between the paired bands is at least 50 nm. For example, in one embodiment the following pairs are formed: pair (i) 520 nm/590 nm, pair (ii) 540 nm/610 nm, pair (iii) 560 nm/620 nm, and pair (iv) 580 nm/640 nm. Advantageously, paired bands where the center of each band in the pair is at least 50 nm apart allows facilitates the effectiveness of the dual bandpass filters used to cover the photo-sensors in some embodiments, because the two wavelengths ranges that each such bandpass filter permits to pass through are far enough apart from each other to ensure filter effectiveness. Accordingly, in some implementations, dual pass band filters, allowing passage of one spectral band from the first group and one spectral band from the second group, are placed in front of each photo-sensor, such that one image is captured at a spectral band belonging to the first group (e.g., upon illumination of the object by light source 106), and one image is captured at a spectral band belonging to the second group (e.g., upon illumination of the object by light source 107).

In one implementation, where the hyperspectral data cube is used for determining the oxyhemoglobin and deoxyhemoglobin content of a tissue, the first filter has a pass band starting at between 430 nm and 510 nm and ending between 570 nm and 590 nm, and the second filter has a pass band starting at between 570 nm and 580 nm and ending between 645 nm and 700 nm.

In a first implementation, the imaging device 100 is configured to collect a set of images, where each image in the set of images is collected at a discrete spectral band, and the set of images comprises images collected at any 4 or more, any 5 or more, any six or more, any seven or more, or all of the set of discrete spectral bands having central wavelengths {510±5 nm, 530±5 nm, 540±5 nm, 560±5 nm, 580±5 nm, 590±5 nm, 620±5 nm, and 660±5 nm}, where each respective spectral band in the set has a full width at half maximum of less than 15 nm, less than 10 nm, or 5 nm or less. In some embodiments of this first implementation, a first bandpass filter, covering light source 106, has a first pass band that permits wavelengths 500±5-550±5 nm and a second pass band that permits wavelengths 650±5-670±5 nm while all other wavelengths emitted by the light sources are blocked, and a second bandpass filter, covering light source 107, has a single pass band that permits wavelengths 550±5 nm-630±5 nm while all other wavelengths emitted by the light sources are blocked. In other such embodiments of this first implementation, a first bandpass filter, covering light source 106, has a first pass band that permits wavelengths 505±5-545±5 nm and a second pass band that permits wavelengths 655±5-665±5 nm while all other wavelengths emitted by the light sources are blocked, and a second bandpass filter, covering light source 107, has a single pass band that permits wavelengths 555±5 nm-625±5 nm while all other wavelengths emitted by the light sources are blocked.

In a second implementation, the imaging device 100 is configured to collect a set of images, where each image in the set of images is collected at a discrete spectral band, and the set of images comprises images collected at any four or more, any five or more, any six or more, any seven or more, or all of the set of discrete spectral bands having central wavelengths {520±5 nm, 540±5 nm, 560±5 nm, 580±5 nm, 590±5 nm, 610±5 nm, 620±5 nm, and 640±5 nm} where each respective spectral band in the set has a full width at half maximum of less than 15 nm, less than 10 nm, or 5 nm or less. In some embodiments of this second implementation, a first bandpass filter, covering each first light source 106-N-A of each light source set, has a first pass band that permits wavelengths 510±5-570±5 nm and a second pass band that permits wavelengths 630±5-650±5 nm while all other wavelengths emitted by the light sources are blocked, and a second bandpass filter, covering each second light source 106-N-B of each light source set, has a single pass band that permits wavelengths 570±5 nm-630±5 nm, while all other wavelengths emitted by the light sources are blocked. In other such embodiments of this second implementation, a first bandpass filter, covering each first light source 106-N-A of each light set, has a first pass band that permits wavelengths 515±5-565±5 nm and a second pass band that permits wavelengths 635±5-645±5 nm while all other wavelengths emitted by the light sources are blocked, and a second bandpass filter, covering each second light source 106-N-B of each light source set, has a single pass band that permits wavelengths 575±5 nm-625±5 nm while all other wavelengths emitted by the light sources are blocked.

In a third implementation, the imaging device 100 is configured to collect a set of images, where each image in the set of images is collected at a discrete spectral band, and the set of images comprises images collected at any four or more, any five or more, any six or more, any seven or more, or all of the set of discrete spectral bands having central wavelengths {500±5 nm, 530±5 nm, 545±5 nm, 570±5 nm, 585±5 nm, 600±5 nm, 615±5 nm, and 640±5 nm}. In such embodiments, each respective spectral band in the set has a full width at half maximum of less than 15 nm, less than 10 nm, or 5 nm or less. In some embodiments of this third implementation, a separate first bandpass filter covers each first light source 106-N-A of the plurality of light source sets, each such first bandpass filter having a first pass band that permits wavelengths 490±5-555±5 nm and a second pass band that permits wavelengths 630±5-650±5 nm while all other wavelengths emitted by the light sources are blocked. Further, a second bandpass filter covers each second light source 106-N-B of each light source set. Each such second bandpass filter has a single pass band that permits wavelengths 560±5 nm-625±5 nm, while all other wavelengths emitted by the light sources are blocked. In other such embodiments of this third implementation, a separate first bandpass filter covers each first light source 106-N-A of each light source set. Each such first bandpass filter has a first pass band that permits wavelengths 495±5-550±5 nm and a second pass band that permits wavelengths 635±5-645±5 nm while all other wavelengths emitted by the light sources are blocked. Further, a separate second bandpass filter covers each second light source 106-N-B of each light source set, has a single pass band that permits wavelengths 565±5 nm-620±5 nm while all other wavelengths emitted by the light sources are blocked.

In some implementations, light sources 106 and 107 are broadband light sources (e.g., white LEDs). First light source 106 is covered by a short pass filter (e.g., a filter allowing light having wavelengths below a cut-off wavelength to pass through while blocking light having wavelengths above the cut-off wavelength) and second light source 107 is covered by a long pass filter (e.g., a filter allowing light having wavelengths above a cut-on wavelength to pass through while blocking light having wavelengths below the cut-on wavelength). The cut-off and cut-on wavelengths of the short and long pass filters are determined based on the set of spectral bands to be captured by the imaging system. Generally, respective cut-off and cut-on wavelengths are selected such that they are longer than the longest wavelength to be captured in a first set of images and shorter than the shortest wavelength to be captured in a second set of images (e.g., where the first and second set of images are combined to form a hyperspectral data set).

Figure 3:
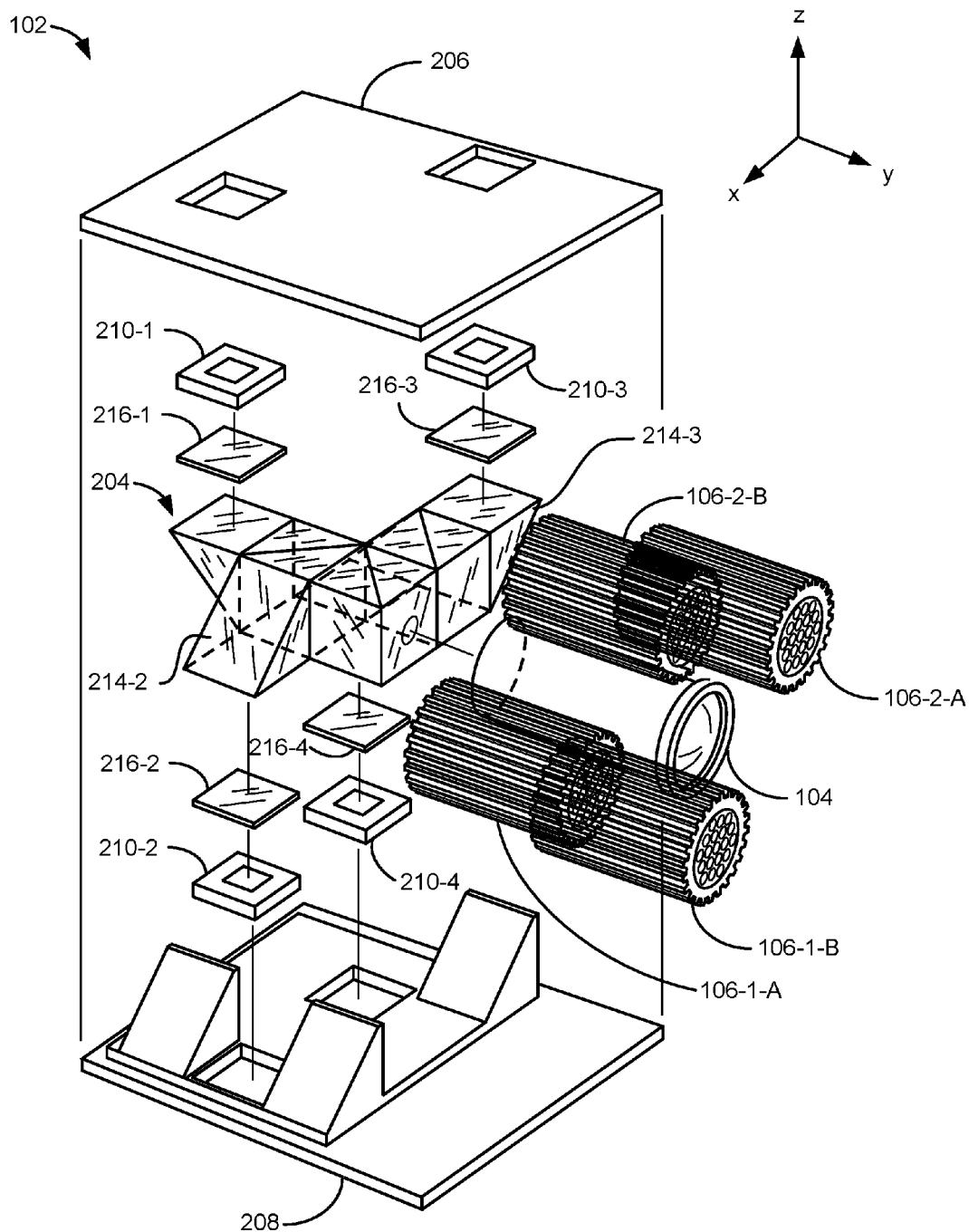
FIG. 3 is an exploded schematic view of an implementation of an optical assembly 102 of a hyperspectral imaging device 100.

For example, referring to FIG. 2B and FIG. 3, in one implementation, photo-sensors 210 are each covered by a dual pass band filter 216. Each dual pass band filter 216 allows light of first and second spectral bands to pass through to the respective photo-sensor 210. Cut-off and cut-on wavelengths for filters covering light sources 106 and 107 are selected such that exactly one pass band from each filter 216 is below the cut-off wavelength of the filter covering light source 106 and the other pass band from each filter 216 is above the cut-on wavelength of the filter covering light source 107.

In one implementation, where the hyperspectral data cube is used for determining the oxyhemoglobin and deoxyhemoglobin content of a tissue, the cut-off wavelength of the short-pass filter covering light source 106 and the cut-on wavelength of the long-pass filter covering light source 107 are between 565 nm and 585 nm.

In a first implementation, the hyperspectral imaging device is configured to collect images at spectral bands having central wavelengths of 510±5 nm, 530±5 nm, 540±5 nm, 560±5 nm, 580±5 nm, 590±5 nm, 620±5 nm, and 660±5 nm, where each respective spectral band has a full width at half maximum of less than 15 nm, and the cut-off wavelength of a short-pass filter covering light source 106 and cut-on wavelength of a long-pass filter covering light source 107 are each independently 570±5 nm.

In a second implementation, the hyperspectral imaging device is configured to collect images at spectral bands having central wavelengths of 520±5 nm, 540±5 nm, 560±5 nm, 580±5 nm, 590±5 nm, 610±5 nm, 620±5 nm, and 640±5 nm, where each respective spectral band has a full width at half maximum of less than 15 nm, and the cut-off wavelength of a short-pass filter covering light source 106 and cut-on wavelength of a long-pass filter covering light source 107 are each independently 585±5 nm.

In a third implementation, the hyperspectral imaging device is configured to collect images at spectral bands having central wavelengths of 500±5 nm, 530±5 nm, 545±5 nm, 570±5 nm, 585±5 nm, 600±5 nm, 615±5 nm, and 640±5, where each respective spectral band has a full width at half maximum of less than 15 nm, and the cut-off wavelength of a short-pass filter covering light source 106 and cut-on wavelength of a long-pass filter covering light source 107 are each independently 577.5±5 nm.

In various implementations, the imaging device 100 includes three or more light source types (e.g., 3, 4, 5, 6, or more). In such cases, any appropriate assignments of spectral ranges (or any other desired characteristic) among the three or more light sources may be used. For example, each light source can be configured to emit light according to each mode of operation desired. Thus, for example, if four substantially non-overlapping spectral ranges are required from four light sources, each respective light source may be configured to emit light within each of the four spectral ranges. In other cases, each respective light source may be configured to emit light within a different respective one of the four spectral ranges. In such instances, it is preferable that there be at least two light sources for each such spectral range, with each such light source being on a different side of the objective lens 104 and concurrently fired to prevent shadowing on the tissue of interest. In yet other cases, two of the light sources may be configured to emit light within each of two of the four spectral ranges, and the other two light sources may be configured to emit light within each of the remaining two spectral ranges. Other assignments of spectral ranges among the light sources are also contemplated.

Figure 4:
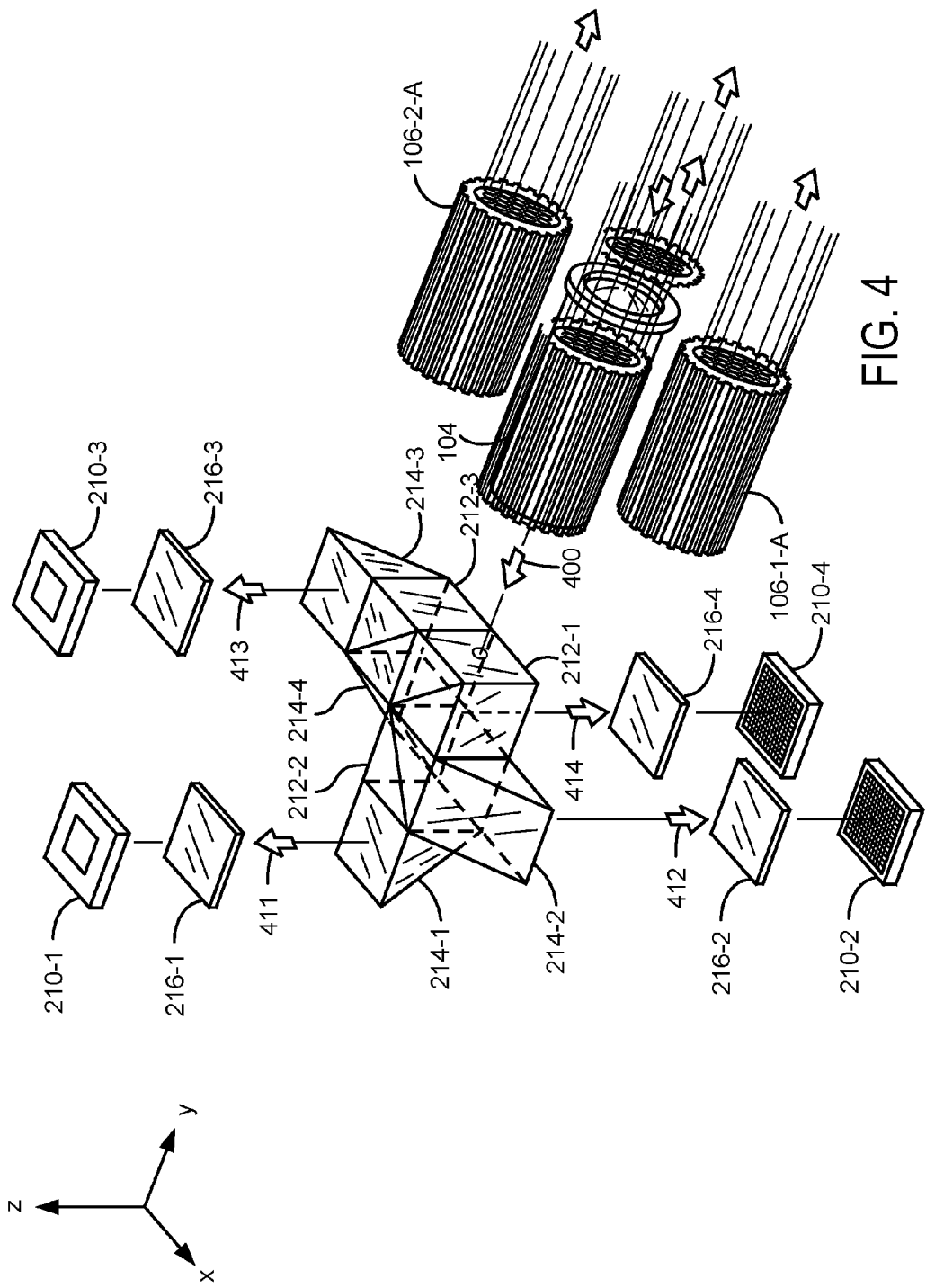
FIG. 4 is an exploded schematic view of the optical paths 400-404 of an implementation of an optical assembly 102 of a hyperspectral imaging device 100.

With reference to FIG. 4, the optical assembly 102 also includes an optical path assembly 204 that directs light received by the lens assembly 104 to a plurality of photo-sensors 210 (e.g., 210-1, . . . 210-4) coupled to the first and the second circuit boards 206, 208. In particular, as described herein, the optical path assembly 204 includes a plurality of beam splitters 212 (e.g., 212-1 . . . 212-3) and a plurality of beam steering elements 214 (e.g., 214-2, 214-4). The beam splitters 212 and the beam steering elements 214 are configured to split the light received by the lens assembly 104 into a plurality of optical paths, and direct those optical paths onto the plurality of photo-sensors 210 of the optical assembly 102.

Beam splitters of several different types may be used in the optical assembly 102 in various implementations. One type of beam splitter that is used in various implementations is configured to divide a beam of light into two separate paths that each have substantially the same spectral content. For example, approximately 50% of the light incident on the beam splitter is transmitted in a first direction, while the remaining approximately 50% is transmitted in a second direction (e.g., perpendicular to the first direction). Other ratios of the light transmitted in the two directions may also be used in various implementations. For ease of reference, this type of beam splitter is referred to herein as a 50:50 beam splitter, and is distinguished from a dichroic beam splitter that divides a beam of light into to two separate paths that each have a different spectral content. For example, a dichroic beam splitter that receives light having a spectral range of 450-650 nm (or more) may transmit light having a spectral range of 450-550 nm in a first direction, and transmit light having a spectral range of 550-650 nm in a second direction (e.g., perpendicular to the first direction).

In addition, other ranges may be utilized, including but not limited to discontinuous spectral sub-ranges. For example, a first spectral range includes a first spectral sub-range of about 450-550 nm and a second spectral sub-range of about 615-650 nm, and second, third and fourth spectral ranges may be about 550-615 nm, 585-650 nm and 450-585 nm, respectively. Alternatively, various beam splitters may be utilized to split light into a first spectral range having a first spectral sub-range of about 450-530 nm and a second spectral sub-range of about 600-650 nm, a second spectral range of about 530-600 nm, a third spectral range having at least two discontinuous spectral sub-ranges including a third spectral sub-range of about 570-600 nm and a fourth spectral sub-range of about 615-650 nm, a fourth spectral range having at least two discontinuous spectral sub-ranges including a fifth spectral sub-range of about 450-570 nm and a sixth spectral sub-range of about 600-615 nm, at least two discontinuous spectral sub-ranges of a fifth spectral range including a seventh spectral sub-range of about 585-595 nm and an eighth spectral sub-range of about 615-625 nm, and at least two discontinuous spectral sub-ranges of a sixth spectral range including a ninth spectral sub-range of about 515-525 nm and a tenth spectral sub-range of about 555-565 nm.

In various implementations, the beam splitters 212 are 50:50 beam splitters. In various implementations, the beam splitters 212 are dichroic beam splitters (e.g., beam splitters that divide a beam of light into separate paths that each have a different spectral content). In various implementations, the beam splitters 212 include a combination of 50:50 beam splitters and dichroic beam splitters. Several specific examples of optical assemblies 102 employing beam splitters of various types are discussed herein.

The optical path assembly 204 is configured such that the image that is provided to each of the photo-sensors (or, more particularly, the filters that cover the photo-sensors) is substantially identical (e.g., the same image is provided to each photo-sensor). Because the photo-sensors 210 can all be operated simultaneously, the optical assembly 102 is able to capture a plurality of images of the same object at substantially the same time (thus capturing multiple images that correspond to the same lighting conditions of the object). Moreover, because each photo-sensor 210-$n$ is covered by a bandpass filter 216-$n$ having a different passband, each photo-sensor 210-$n$ captures a different spectral component of the image. These multiple images, each representing a different spectral component, are then assembled into a hyperspectral data cube for analysis.

In some embodiments, each photo-sensor 210-$n$ is a pixel array. In some embodiments each photo-sensor 210-$n$ comprises 500,000 pixels, 1,000,000 pixels, 1,100,000 pixels, 1,200,000 pixels or more than 1,300,000 pixels. In an exemplary embodiment a photo-sensor in the plurality of photo-sensors is ½-inch megapixel CMOS digital image sensor such as the MT9M001C12STM monochrome sensor (Aptina Imaging Corporation, San Jose, Calif.).

FIG. 3 is an exploded schematic view that includes the optical assembly 102, in accordance with various implementations. FIG. 3 further illustrates the arrangement of the various components of the optical assembly. In particular, the optical assembly 102 includes a first circuit board 206 and a second circuit board 208, where the first and second circuit boards 206, 208 are substantially parallel to one another and are positioned on opposing sides of the optical path assembly 204. In various implementations, the circuit boards 206, 208 are rigid circuit boards.

Coupled to the first circuit board 206 are a first photo-sensor 210-1 and a third photo-sensor 210-3. Coupled to the second circuit board 208 are a second photo-sensor 210-2 and a fourth photo-sensor 210-4. In various implementations, the photo-sensors 210 are coupled directly to their respective circuit boards (e.g., they are rigidly mounted to the circuit board). In various implementations, in order to facilitate precise alignment of the photo-sensors 210 with respect to the optical path assembly 204, the photo-sensors 210 are flexibly coupled to their respective circuit board. For example, in some cases, the photo-sensors 210 are mounted on a flexible circuit (e.g., including a flexible substrate composed of polyamide, PEEK, polyester, or any other appropriate material). The flexible circuit is then electronically coupled to the circuit board 206, 208. In various implementations, the photo-sensors 210 are mounted to rigid substrates that are, in turn, coupled to one of the circuit boards 206, 208 via a flexible interconnect (e.g., a flexible board, flexible wire array, flexible PCB, flexible flat cable, ribbon cable, etc.).

As noted above, the optical assembly 102 includes a plurality of bandpass filters 216 (e.g., 216-1 . . . 216-4). The bandpass filters 216 are positioned between the photo-sensors 210 and their respective optical outlets of the optical path assembly 204. Thus, the bandpass filters 216 are configured to filter the light that is ultimately incident on the photo-sensors 210. In some embodiments, each bandpass filter 216 is a dual bandpass filter.

In various implementations, each bandpass filter 216 is configured to have a different pass band. Accordingly, even though the optical path assembly 204 provides the same image to each photo-sensor (or, more particularly, to the filters that cover the photo-sensors), each photo-sensor actually captures a different spectral component of the image. For example, as discussed in greater detail herein, a first bandpass filter 216-1 may have a passband centered around 520 nm, and a second bandpass filter 216-2 may have a passband centered around 540 nm. Thus, when the imaging device 100 captures an exposure, the first photo-sensor 210-1 (which is filtered by the first bandpass filter 216-1) will capture an image representing the portion of the incoming light having a wavelength centered around 520 nm, and the second photo-sensor 210-2 (which is filtered by the second bandpass filter 216-2) will capture an image representing the portion of the incoming light having a wavelength around 540 nm. (As used herein, the term exposure refers to a single imaging operation that results in the simultaneous or substantially simultaneous capture of multiple images on multiple photo-sensors.) These images, along with the other images captured by the third and fourth photo sensors 210-3, 210-4 (each capturing a different spectral band), are then assembled into a hyperspectral data cube for further analysis.

In various implementations, at least a subset of the bandpass filters 216 are configured to allow light corresponding to two (or more) discrete spectral bands to pass through the filter. While such filters may be referred to herein as dual bandpass filters, this term is meant to encompass bandpass filters that have two discrete passbands as well as those that have more than two discrete passbands (e.g., triple-band bandpass filters, quadruple-band bandpass filters, etc.). By using bandpass filters that have multiple passbands, each photo-sensor can be used to capture images representing several different spectral bands. For example, the hyperspectral imaging device 100 will first illuminate an object with light within a spectral range that corresponds to only one of the passbands of each of the bandpass filters, and capture an exposure under the first lighting conditions. Subsequently, the hyperspectral imaging device 100 will illuminate an object with light within a spectral range that corresponds to a different one of the passbands on each of the bandpass filters, and then capture an exposure under the second lighting conditions. Thus, because the first illumination conditions do not include any spectral content that would be transmitted by the second passband, the first exposure results in each photo-sensor capturing only a single spectral component of the image. Conversely, because the second illumination conditions do not include any spectral content that would be transmitted by the first passband, the second exposure results in each photo-sensor capturing only a single spectral component of the image.

As a more specific example, in various implementations, the bandpass filters 216-1 through 216-4 each include one passband falling within the range of 500-585 nm, and a second passband falling within the range of 585-650 nm, as shown below in table (1):

TABLE 1

Exemplary Central Wavelengths of Passbands for Filters 216-1-216-4

| | Filter 216-1 | Filter 216-2 | Filter 216-3 | Filter 216-4 |
|---|---|---|---|---|
| Passband 1 | 520 nm | 540 nm | 560 nm | 580 nm |
| Passband 2 | 590 nm | 610 nm | 620 nm | 640 nm |

In one implementation, the plurality of light source sets 106 have two modes of operation: in a first mode of operation, a first light source in each light source set 106 emits light having wavelengths according to a first set of spectral bands (e.g., below 585 nm, such as between 500 nm and 585 nm); in a second mode of operation, a second light source in each light source set emits light having wavelengths according to a second set of spectral bands (e.g., above 585 nm, such as between 585 nm and 650 nm). Thus, when the first exposure is captured using the first illumination mode, four images are captured, where each image corresponds to a single spectral component of the incoming light. Specifically, the image captured by the first sensor 210-1 will include substantially only that portion of the incoming light falling within a first passband (e.g., centered around 520 nm), the image captured by the second sensor 210-2 will include substantially only that portion of the incoming light falling within a second passband (e.g., centered around 540 nm), and so on. When the second exposure is captured using the second illumination mode, four additional images are captured, where each image corresponds to a single spectral component of the incoming light. Specifically, the image captured by the first sensor 210-1 will include substantially only that portion of the incoming light falling within the other pass band allowed by the dual band filter 216-1 (e.g., centered around 590 nm), the image captured by the second sensor 210-2 will include substantially only that portion of the incoming light falling within the other pass band allowed by dual band filter 216-2 (e.g., centered around 610 nm), and so on. The eight images resulting from the two exposures described above are then assembled into a hyperspectral data cube for further analysis.

In another implementation, as illustrated in FIG. 2B, the hyperspectral imaging device has two light source sets, and each light source in each light source set is configured to illuminate an object with a different set of spectral bands. The hyperspectral imaging device has two modes of operation: in a first mode of operation, light sources 106-1-A and 102-2-A emit light having wavelengths according to a first set of spectral bands. In a second mode of operation, light sources 106-1-B and 106-2-B emit light having wavelengths according to a second set of spectral bands. Thus, when the first exposure is captured using the first illumination mode, four images are captured, where each image corresponds to a single spectral component of the incoming light. Specifically, the image captured by the first sensor 210-1 during the first mode of operation will include substantially only that portion of the incoming light falling within a first passband (e.g., centered around 520 nm), the image captured by the second sensor 210-2 during the first mode of operation will include substantially only that portion of the incoming light falling within a second passband (e.g., centered around 540 nm), and so on. When the second exposure is captured using the second illumination mode, four additional images are captured, where each image corresponds to a single spectral component of the incoming light. Specifically, the image captured by the first sensor 210-1 will include substantially only that portion of the incoming light falling within the other pass band allowed by the dual band filter 216-1 (e.g., centered around 590 nm), the image captured by the second sensor 210-2 will include substantially only that portion of the incoming light falling within the other pass band allowed by dual band filter 216-2 (e.g., centered around 610 nm), and so on. The eight images resulting from the two exposures described above are then assembled into a hyperspectral data cube for further analysis. In typical embodiments, each such image is a multi-pixel image. In some embodiments, this assembly involves combining each image in the plurality of images, on a pixel by pixel basis, to form a composite image.

In the above examples, each filter 216-*n* has two passbands. However, in various implementations, the filters do not all have the same number of passbands. For example, if fewer spectral bands need to be captured, one or more of the filters 216-*n* may have only one passband. Similarly, one or more of the filters 216-*n* may have additional passbands. In the latter case, the light source 104 will have additional modes of operation, where each mode of operation illuminates an object with light that falls within only 1 (or none) of the passbands of each sensor.

FIG. 4 is an exploded schematic view of a portion of the optical assembly 102, in accordance with various implementations, in which the optical paths formed by the optical path assembly 204 are shown. The optical path assembly 204 channels light received by the lens assembly 104 to the various photo-sensors 210 of the optical assembly 102.

Turning to FIG. 4, the optical assembly 102 includes a first beam splitter 212-1, a second beam splitter 212-2, and a third beam splitter 212-3. Each beam splitter is configured to split the light received by the beam splitter into at least two optical paths. For example, beam splitters for use in the optical path assembly 204 may split an incoming beam into one output beam that is collinear to the input beam, and another output beam that is perpendicular to the input beam.

Specifically, the first beam splitter 212-1 is in direct optical communication with the lens assembly 104, and as shown in FIG. 10, splits the incoming light (represented by arrow 400) into a first optical path 401 and a second optical path 402. The first optical path 401 is substantially collinear with the light entering the first beam splitter 212-1, and passes to the second beam splitter 212-2. The second optical path 402 is substantially perpendicular to the light entering the first beam splitter 212-1, and passes to the third beam splitter 212-3. In various implementations, the first beam splitter 212-1 is a 50:50 beam splitter. In other implementations, the first beam splitter 212-1 is a dichroic beam splitter.

With continued reference to FIG. 10, the second beam splitter 212-2 is adjacent to the first beam splitter 212-1 (and is in direct optical communication with the first beam splitter 212-1), and splits the incoming light from the first beam splitter 212-1 into a third optical path 403 and a fourth optical path 404. The third optical path 403 is substantially collinear with the light entering the second beam splitter 212-2, and passes through to the first beam steering element 214-1 (see FIG. 4). The fourth optical path is substantially perpendicular to the light entering the second beam splitter 212-2, and passes through to the second beam steering element 214-2. In various implementations, the second beam splitter 212-2 is a 50:50 beam splitter. In other implementations, the second beam splitter 212-2 is a dichroic beam splitter.

The beam steering elements 214 (e.g., 214-1 . . . 214-4 shown in FIG. 4) are configured to change the direction of the light that enters one face of the beam steering element. Beam steering elements 214 are any appropriate optical device that changes the direction of light. For example, in various implementations, the beam steering elements 214 are prisms (e.g., folding prisms, bending prisms, etc.). In various implementations, the beam steering elements 214 are mirrors. In various implementations, the beam steering elements 214 are other appropriate optical devices or combinations of devices.

Returning to FIG. 4, the first beam steering element 214-1 is adjacent to and in direct optical communication with the second beam splitter 212-2, and receives light from the third optical path (e.g., the output of the second beam splitter 212-2 that is collinear with the input to the second beam splitter 212-2). The first beam steering element 214-1 deflects the light in a direction that is substantially perpendicular to the fourth optical path (and, in various implementations, perpendicular to a plane defined by the optical paths of the beam splitters 212, e.g., the x-y plane) and onto the first photo-sensor 210-1 coupled to the first circuit board 206 (FIG. 3). The output of the first beam steering element 214-1 is represented by arrow 411 (see FIG. 4).

The second beam steering element 214-2 is adjacent to and in direct optical communication with the second beam splitter 212-2, and receives light from the fourth optical path (e.g., the perpendicular output of the second beam splitter 212-2). The second beam steering element 214-2 deflects the light in a direction that is substantially perpendicular to the third optical path (and, in various implementations, perpendicular to a plane defined by the optical paths of the beam splitters 212, e.g., the x-y plane) and onto the second photo-sensor 210-2 coupled to the second circuit board 208 (FIG. 3). The output of the second beam steering element 214-2 is represented by arrow 412 (see FIG. 4).

As noted above, the first beam splitter 212-1 passes light to the second beam splitter 212-2 along a first optical path (as discussed above), and to the third beam splitter 212-3 along a second optical path.

With reference to FIG. 10, the third beam splitter 212-3 is adjacent to the first beam splitter 212-1 (and is in direct optical communication with the first beam splitter 212-1), and splits the incoming light from the first beam splitter 212-1 into a fifth optical path 405 and a sixth optical path 406. The fifth optical path 405 is substantially collinear with the light entering the third beam splitter 212-3, and passes through to the third beam steering element 214-3 (see FIG. 4). The sixth optical path is substantially perpendicular to the light entering the third beam splitter 212-3, and passes through to the fourth beam steering element 214-4. In various implementations, the third beam splitter 212-3 is a 50:50 beam splitter. In other implementations, the third beam splitter 212-3 is a dichroic beam splitter.

The third beam steering element 214-3 (see FIG. 4) is adjacent to and in direct optical communication with the third beam splitter 212-3, and receives light from the fifth optical path (e.g., the output of the third beam splitter 212-3 that is collinear with the input to the third beam splitter 212-3). The third beam steering element 214-3 deflects the light in a direction that is substantially perpendicular to the third optical path (and, in various implementations, perpendicular to a plane defined by the optical paths of the beam splitters 212, e.g., the x-y plane) and onto the third photo-sensor 210-3 coupled to the first circuit board 206 (FIG. 3). The output of the third beam steering element 214-3 is represented by arrow 413 (see FIG. 4).

The fourth beam steering element 214-4 is adjacent to and in direct optical communication with the third beam splitter 212-3, and receives light from the sixth optical path (e.g., the perpendicular output of the third beam splitter 212-3). The fourth beam steering element 214-4 deflects the light in a direction that is substantially perpendicular to the sixth optical path (and, in various implementations, perpendicular to a plane defined by the optical paths of the beam splitters 212, e.g., the x-y plane) and onto the fourth photo-sensor 210-4 coupled to the second circuit board 208 (FIG. 3). The output of the fourth beam steering element 214-4 is represented by arrow 414 (see FIG. 4).

As shown in FIG. 4, the output paths of the first and third beam steering elements 214-1, 214-3 are in opposite directions than the output paths of the second and fourth beam steering elements 214-2, 214-4. Thus, the image captured by the lens assembly 104 is projected onto the photo-sensors mounted on the opposite sides of the image assembly 102. However, the beam steering elements 212 need not face these particular directions. Rather, any of the beam steering elements 212 can be positioned to direct the output path of each beam steering element 212 in any appropriate direction. For example, in various implementations, all of the beam steering elements 212 direct light in the same direction. In such cases, all of the photo-sensors may be mounted on a single circuit board (e.g., the first circuit board 206 or the second circuit board 208, FIG. 3). Alternatively, in various implementations, one or more of the beam steering elements 212 directs light substantially perpendicular to the incoming light, but in substantially the same plane defined by the optical paths of the beam splitters 212 (e.g., within the x-y plane). In yet other implementations, one or more beam steering elements 214 are excluded from the imaging device, and the corresponding photo-sensors 210 are positioned orthogonal to the plane defined by optical paths 400-1 to 400-6.

Figure 5A:
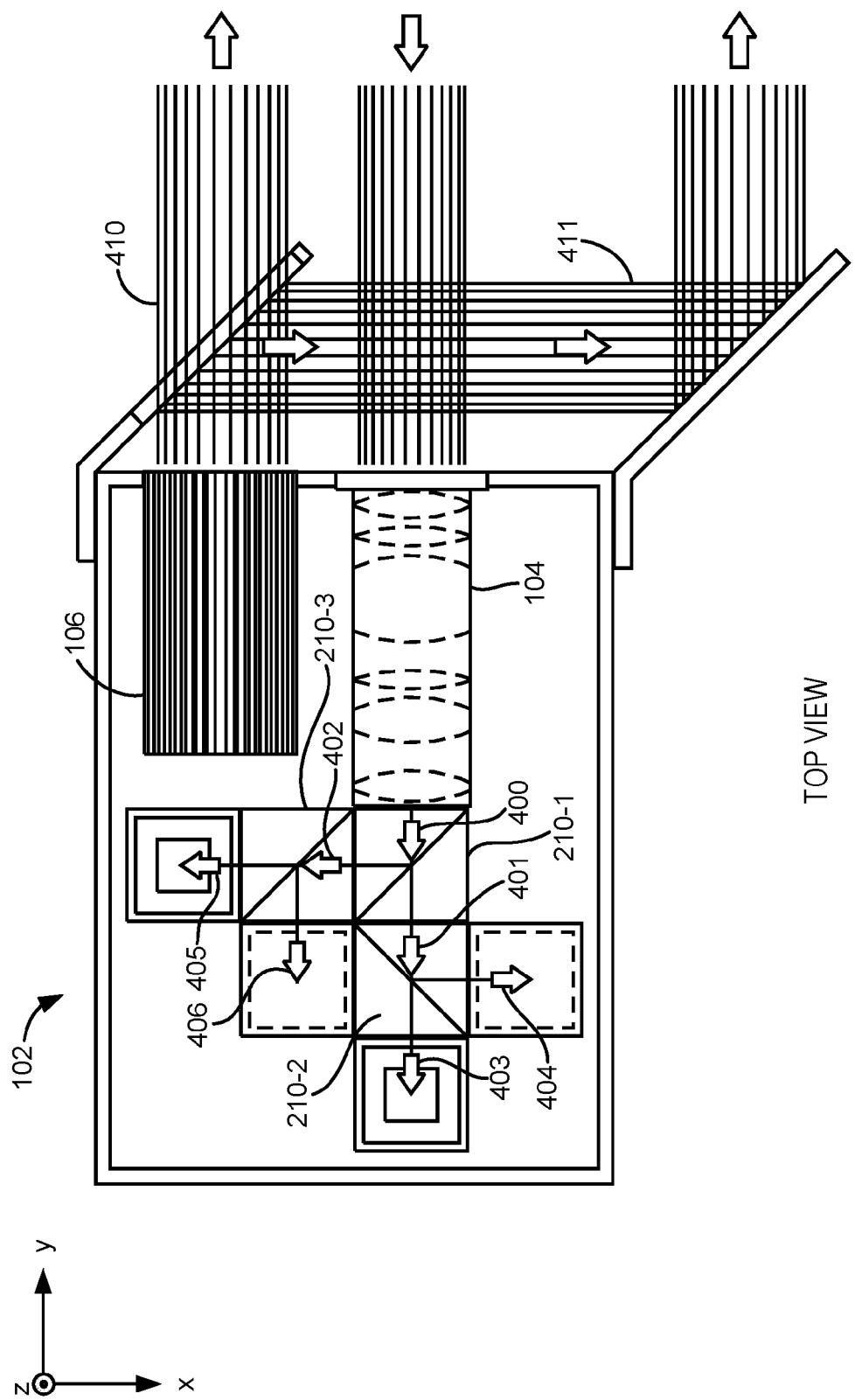

FIG. 5A is a cross-sectional view of the optical assembly 102 and the optical path assembly 204 in accordance with various implementations, and FIG. 10 is a two-dimensional schematic illustration of the optical paths within the optical path assembly 204. Although illustrated with a single light source 106, this optical path assembly is typically implemented using a plurality of light source sets, one of which is illustrated in FIG. 5C and two of which are illustrated in FIGS. 3 and 4. Light from the lens assembly 104 enters the first beam splitter 210-1, as indicated by arrow 400. The first beam splitter 210-1 splits the incoming light (arrow 400) into a first optical path (arrow 401) that is collinear to the incoming light (arrow 400). Light along the first optical path (arrow 401) is passed through to the second beam splitter 210-2. The first beam splitter 210-1 also splits the incoming light (arrow 400) into a second optical path (arrow 402) that is perpendicular to the incoming light (arrow 400). Light along the second optical path (arrow 402) is passed through to the third beam splitter 210-3.

Light entering the second beam splitter 210-2 (arrow 402) is further split into a third optical path (arrow 403) that is collinear with the incoming light (arrow 400 and/or arrow 402). Light along the third optical path (arrow 403) is passed to the first beam steering element 214-1 (see, e.g., FIG. 4), which steers the light onto the first photo-sensor 210-1. As discussed above, in various implementations, the first beam steering element 214-1 deflects the light in a direction that is perpendicular to the light entering the second beam splitter and out of the plane defined by the beam splitters (e.g., in a positive z-direction, or out of the page, as shown in FIG. 5).

Light entering the second beam splitter 210-2 (arrow 402) is further split into a fourth optical path (arrow 404) that is perpendicular to the incoming light (arrow 400 and/or arrow 402). Light along the fourth optical path (arrow 404) is passed to the second beam steering element 214-2, which steers the light onto the second photo-sensor 210-2. As discussed above, in various implementations, the second beam steering element 214-2 deflects the light in a direction that is perpendicular to the light entering the second beam splitter and out of the plane defined by the beam splitters (e.g., in a negative z-direction, or into the page, as shown in FIG. 5).

Light entering the third beam splitter 210-3 (arrow 402) is further split into a fifth optical path (arrow 405) that is collinear with the light incoming into the third beam splitter 210-3 (arrow 402). Light along the fifth optical path (arrow 405) is passed to the third beam steering element 214-3 (see, e.g., FIG. 4), which steers the light onto the third photo-sensor 210-3. As discussed above, in various implementations, the third beam steering element 214-3 deflects the light in a direction that is perpendicular to the light entering the third beam splitter and out of the plane defined by the beam splitters (e.g., in a positive z-direction, or out of the page, as shown in FIG. 5).

Light entering the third beam splitter 210-3 (arrow 402) is further split into a sixth optical path (arrow 406) that is perpendicular to the light incoming into the third beam splitter 210-3 (arrow 402). Light along the sixth optical path (arrow 406) is passed to the fourth beam steering element 214-4, which steers the light onto the fourth photo-sensor 210-4. As discussed above, in various implementations, the fourth beam steering element 214-4 deflects the light in a direction that is perpendicular to the light entering the third beam splitter and out of the plane defined by the beam splitters (e.g., in a negative z-direction, or into the page, as shown in FIG. 5).

Figure 5B:
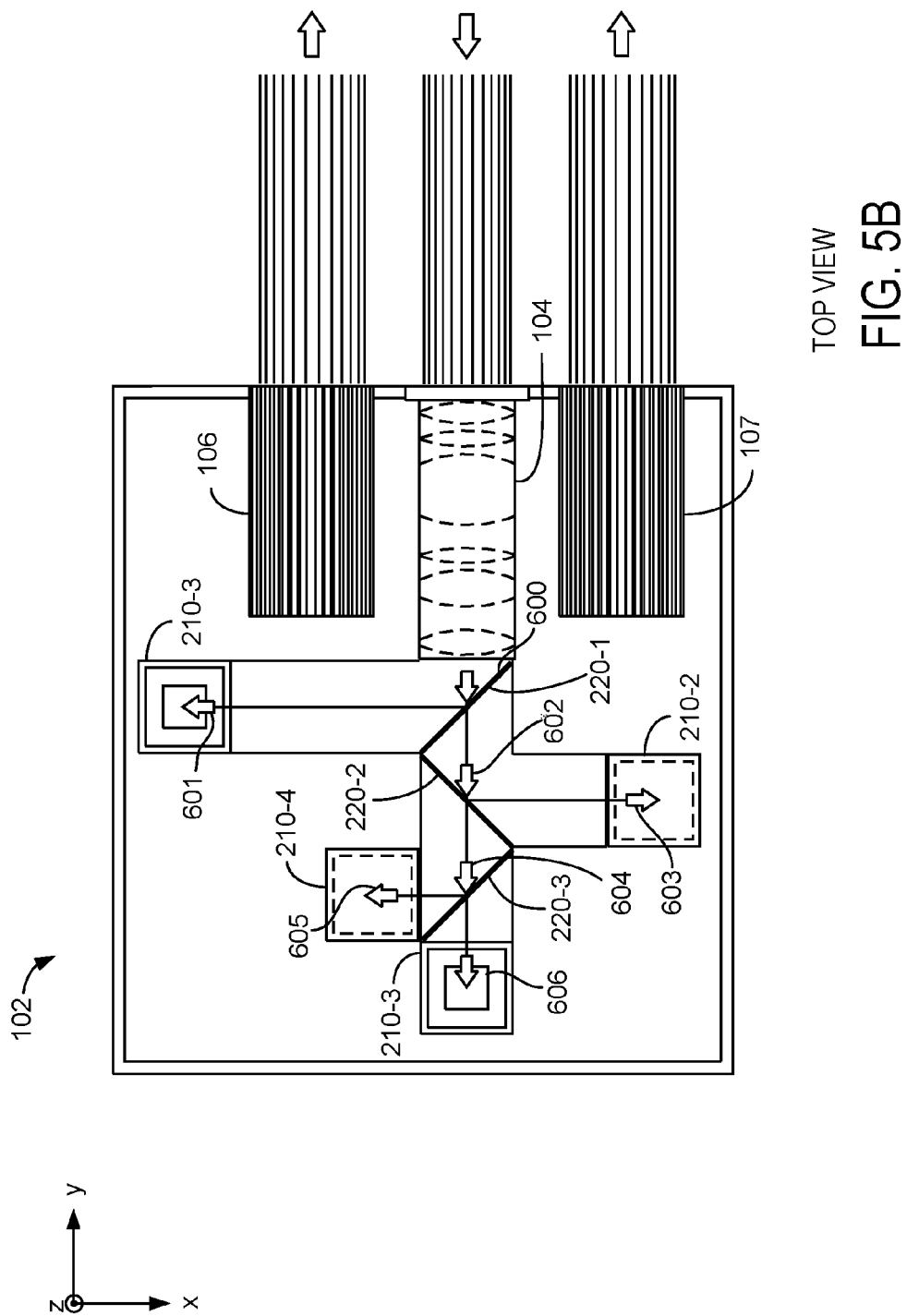
Figure 12:
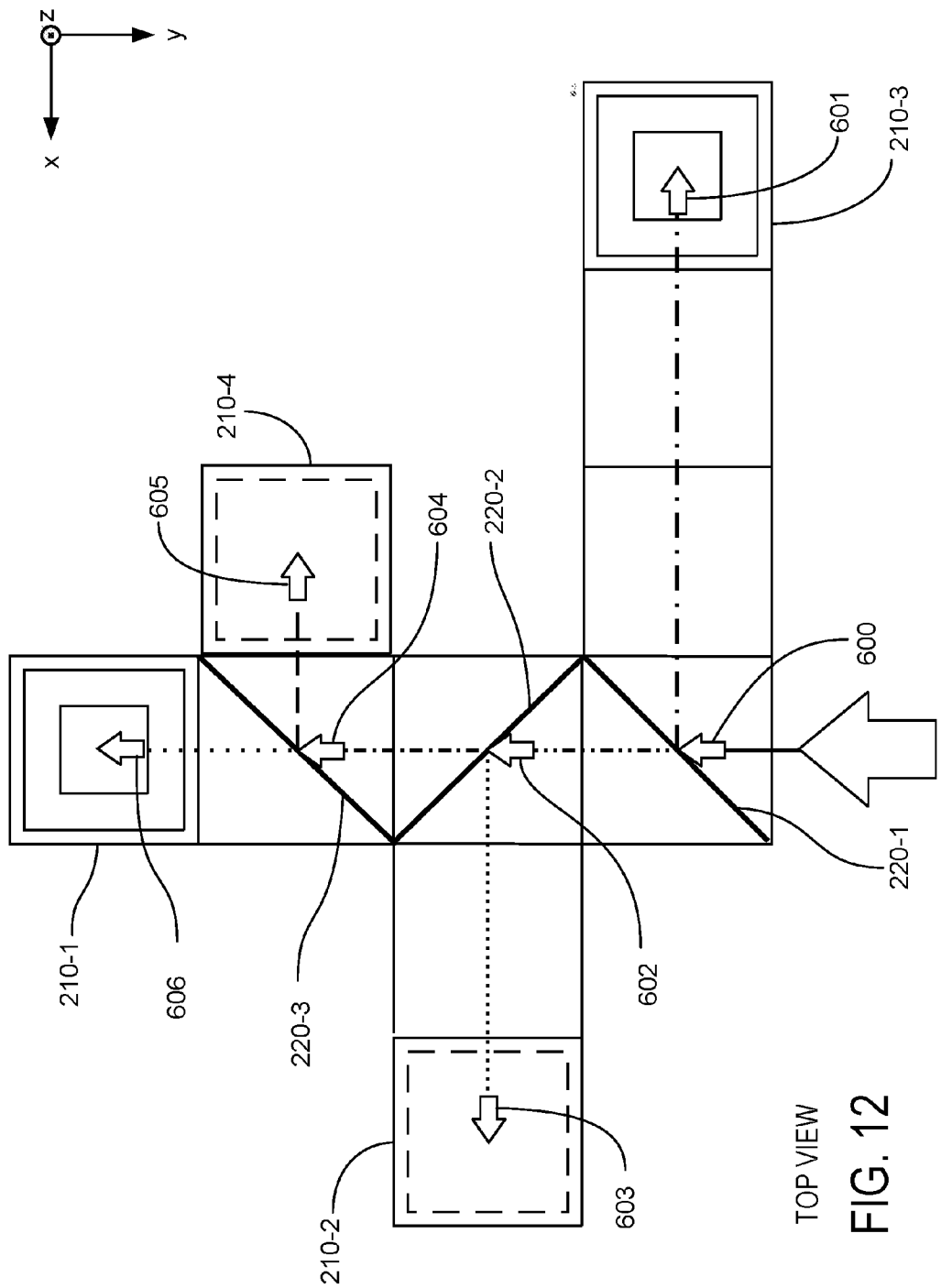
FIG. 12 is a two-dimensional schematic illustration of the optical paths of an implementation of an optical assembly 102 of a hyperspectral imaging device 100.

FIG. 5B is a top schematic view of the optical assembly 102 and the optical path assembly 204 in accordance with various implementations, and FIG. 12 is a two-dimensional schematic illustration of the optical paths within the optical path assembly 204. Although illustrated with a single light source set, the optical path is more typically illuminated by a plurality of sets of light sources as illustrated in FIGS. 3 and 4, where each light source in the light source set is configured to operate in one or more operating modes (e.g., two operating modes as described herein).

Light from the lens assembly 104 enters the first beam splitter 220-1, as indicated by arrow 600. The first beam splitter 220-1 splits the incoming light (arrow 600) into a first optical path (arrow 601) that is perpendicular to the incoming light (arrow 600) and a second optical path (arrow 602) that is collinear to the incoming light (arrow 600). Light along the first optical path (arrow 601) is passed to a beam steering element in similar manner described above, which steers the light onto the third photo-sensor 210-3. As discussed above, in various implementations, the steering element deflects the light in a direction that is perpendicular to the first optical path (arrow 601) and out of the plane (e.g., in a positive z-direction, or out of the page) toward the third photo-sensor 210-3. Light along the second optical path (arrow 602) is passed through to a second beam splitter 220-2.

The second beam splitter 220-2 splits the incoming light (arrow 602) into a third optical path (arrow 603) that is perpendicular to the incoming light (arrow 602) and a fourth optical path (arrow 604) that is collinear to the incoming light (arrow 602). Light along the third optical path (arrow 603) is passed to another beam steering element in similar manner described above, which steers the light onto the second photo-sensor 210-2. As discussed above, in various implementations, the steering element deflects the light in a direction that is perpendicular to the third optical path (arrow 603) and out of the plane (e.g., in a negative z-direction, or into the page) toward the second photo-sensor 210-2. Light along the fourth optical path (arrow 604) is passed through to a third beam splitter 220-3.

The third beam splitter 220-3 splits the incoming light (arrow 604) into a fifth optical path (arrow 605) that is perpendicular to the incoming light (arrow 604) and a sixth optical path (arrow 606) that is collinear to the incoming light (arrow 604). Light along the fifth optical path (arrow 605) is passed to another beam steering element, which steers the light onto the fourth photo-sensor 210-4. As discussed above, in various implementations, the steering element deflects the light in a direction that is perpendicular to the firth optical path (arrow 605) and out of the plane (e.g., in a negative z-direction, or into the page) toward the fourth photo-sensor 210-4. Light along the sixth optical path (arrow 606) is passed to another beam steering element, which steers the light onto the first photo-sensor 210-1. As discussed above, in various implementations, the steering element deflects the light in a direction that is perpendicular to the sixth optical path (arrow 606) and out of the plane (e.g., in a positive z-direction, or out of the page) toward the first photo-sensor 210-1.

Figure 6:
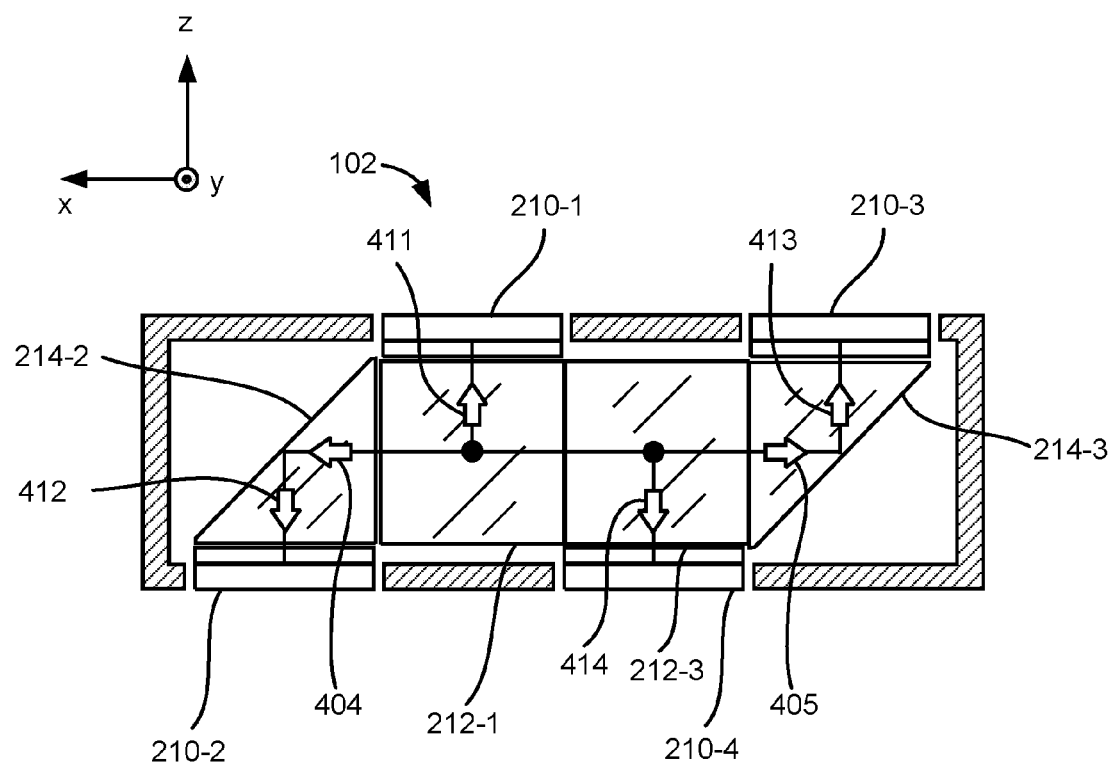
FIG. 6 is an illustration of a front view of implementations of an optical assembly 102 of a hyperspectral imaging device 100.

FIG. 6 is a front schematic view of the optical assembly 102, in accordance with various implementations. For clarity, the lens assembly 104 and the light source sets 106 are not shown. The lines within the beam splitters 212 and the beam steering elements 214 further depict the light paths described herein. For example, the line designated by arrow 404 illustrates how the beam steering element 214-2 deflects the light received from the beam splitter 212-2 onto the photo-sensor 210-2. Further, the line designated by arrow 402 illustrates how the beam steering element 214-3 deflects the light received from the beam splitter 212-3 onto the photo-sensor 210-3. Arrows 411-414 (corresponding to the optical paths indicated in FIG. 4) further illustrate how the beam steering elements 214 direct light to their respective photo-sensors 210.

In the instant application, the geometric terms such as parallel, perpendicular, orthogonal, coplanar, collinear, etc., are understood to encompass orientations and/or arrangements that substantially satisfy these geometric relationships. For example, when a beam steering element deflects light perpendicularly, it is understood that the beam steering element may deflect the light substantially perpendicularly. As a more specific example, in some cases, light may be determined to be perpendicular (or substantially perpendicular) when the light is deflected 90+/−1 degrees from its input path. Other deviations from exact geometric relationships are also contemplated.

As noted above, the optical assembly 102 can use various combinations of 50:50 beam splitters and dichroic beam splitters. In a first example, the first beam splitter 212-1, the second beam splitter 212-2, and the third beam splitter 212-3 are all 50:50 beam splitters. An example optical assembly 102 with this selection of beam splitters is illustrated in FIG. 10.

In a second example, the first beam splitter 212-1 is a dichroic beam splitter, and the second beam splitter 212-2 and the third beam splitter 212-3 are both 50:50 beam splitters. An example optical assembly 102 with this selection of beam splitters is illustrated in FIG. 11.

In a third example, the first beam splitter 212-1, the second beam splitter 212-2, and the third beam splitter 212-3 are all dichroic beam splitters. An example optical assembly 102 with this selection of beam splitters is illustrated in FIG. 12.

Figure 7:
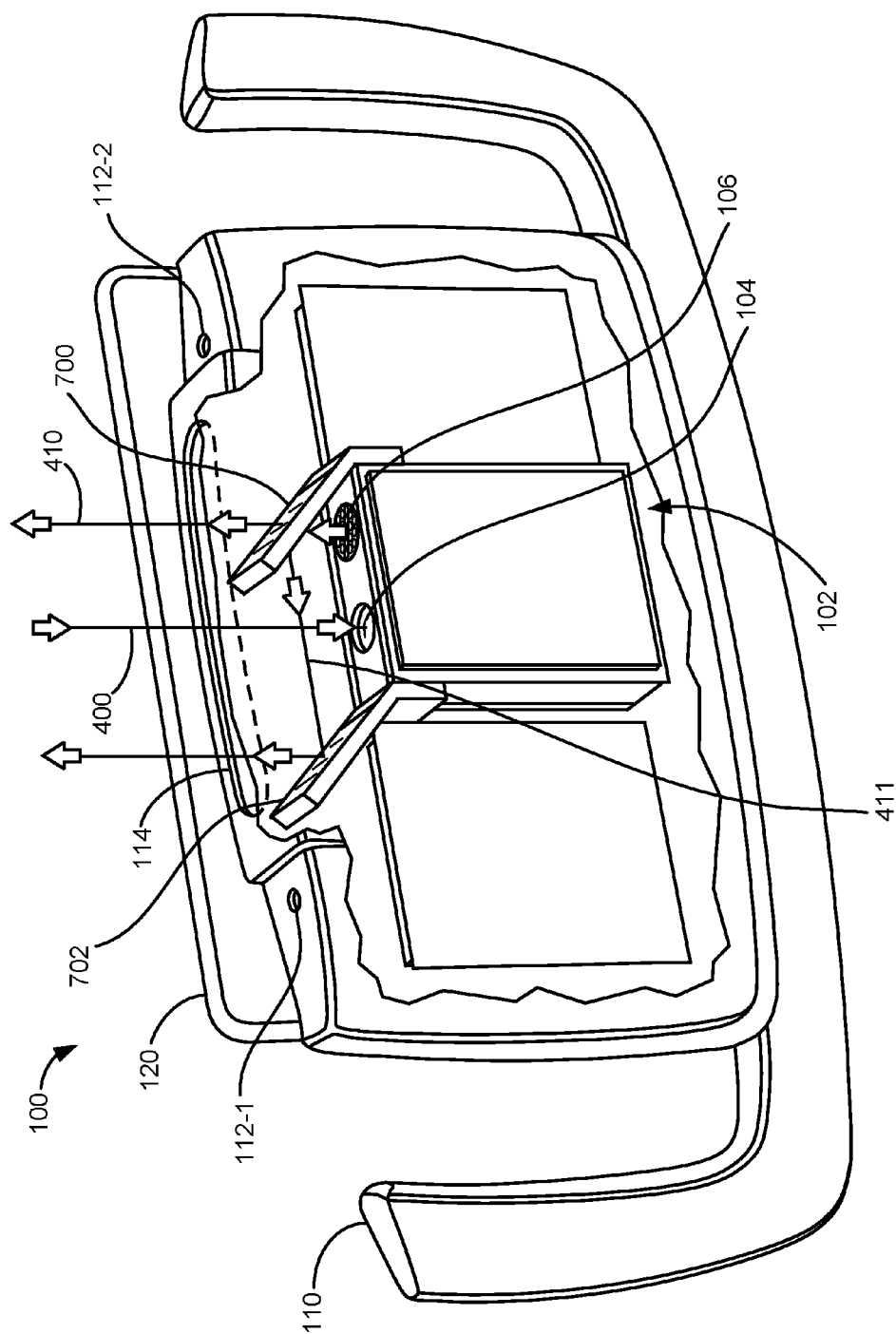
FIG. 7 is a partially cut-out illustration of a bottom view of a hyperspectral imaging device 100, in accordance with an implementation.

FIG. 7 is a cutaway view of an implementation of imaging device 100, illustrating light paths 410 and 411, corresponding to light emitted from light source 106 and illuminating the object being imaged, as well as light path 400, corresponding to light backscattered from the object.

The use of polarized illumination is advantageous because it eliminates surface reflection from the skin and helps to eliminate stray light reflection from off axis imaging directions. Accordingly, in various implementations, polarized light is used to illuminate the object being imaged. In various implementations, the light is polarized with respect to a coordinate system relating to the plane of incidence formed by the propagation direction of the light (e.g., the light emitted by light source 106) and a vector perpendicular to the plane of the reflecting surface (e.g., the object being imaged). The component of the electric field parallel to the plane of incidence is referred to as the p-component and the component perpendicular to the plane is referred to as the s-component. Accordingly, polarized light having an electric field along the plane of incidence is "p-polarized," while polarized light having an electric field normal to the plane is "s-polarized."

Light can be polarized by placing a polarization filter in the path of the light. The polarizer allows light having the same polarization (e.g., p-polarized or s-polarized) to pass through, while reflecting light having the opposite polarization. Because the polarizer is passively filtering the incident beam, 50% of non-polarized light is lost due to reflection off the polarizing filter. In practice, therefore, a non-polarized light source must produce twice the desired amount of polarized illuminating light, at twice the power consumption, to account for this loss. Advantageously, in various implementations, the imaging device recaptures and reverses the polarity light reflected off the polarization filter, using a polarization rotator (e.g., a polarization rotation mirror). In various implementations, at least 95% of all of the light received by the polarizer from the at least one light source may be illuminated onto the object.

Returning to FIG. 7, in one implementation, light emitted from light source 106 along optical path 410 is received by polarizer 700. The portion of the light having the same polarization as polarizer 700 (e.g., s- or p-polarization) passes through polarizer 700 and is directed, through optical window 114, onto the surface of the object. The portion of the light having the opposite polarization as polarizer 700 is reflected orthogonally along optical path 411, directed to polarization rotator 702. Polarization rotator 700 reverses the polarization of the light (e.g., reverses the polarization to match the polarization transmitted through polarizer 700) and reflects the light, through optical window 114, onto the surface of the object. Polarized light backscattered from the object, returning along optical path 400, is captured by lens assembly 104 and is directed internal to optical assembly 102 as described above.

In this fashion, accounting for incidental loss of light along the optical path, substantially all the light emitted from a light source 106 is projected onto the surface of the object being imaged in a polarized manner. This eliminates the need for light source 106 to produce twice the desired amount illuminating light, effectively reducing the power consumption from illumination by 50%.

FIGS. 9A-9C are illustrations of framing guides projected onto the surface of an object for focusing an image collected by an implementation of an imaging device 100.

As noted above, in various implementations, the lens assembly 104 has a fixed focal distance. Thus, images captured by the imaging device 100 will only be in focus if the imaging device 110 is maintained at an appropriate distance from the object to be imaged. In various implementations, the lens assembly 104 has a depth of field of a certain range, such that objects falling within that range will be suitably focused. For example, in various implementations, the focus distance of the lens assembly 104 is 24 inches, and the depth of field is 3 inches. Thus, objects falling anywhere from 21 to 27 inches away from the lens assembly 104 will be suitably focused. These values are merely exemplary, and other focus distances and depths of field are also contemplated.

Referring to FIG. 8A-8B, to facilitate accurate positioning of the imaging device 100 with respect to the object to be imaged, the docking station 110 includes first and second projectors 112 (e.g., 112-1, 112-2) configured to project light (e.g., light 901, 903 in FIGS. 8A and 8B, respectively) onto the object indicating when the imaging device 100 is positioned at an appropriate distance from the object to acquire a focused image. In various implementations, with reference to FIGS. 9A-9C, the first projector 112-1 and the second projector 112-2 are configured to project a first portion 902-1 and a second portion 902-2 of a shape 902 onto the object (FIGS. 9A-9C), respectively. The first portion of the shape 902-1 and the second portion of the shape 902-1 are configured to converge to form the shape 902 when the lens 104 is positioned at a predetermined distance from the object, the predetermined distance corresponding to a focus distance of the lens.

In one implementation, the framing guides converge to form a closed rectangle on the surface of the object when the lens of the imaging device 100 is positioned at predetermined distance from the object corresponding to the focus distance of the lens (FIG. 9C). When the lens of the imaging device 100 is positioned at distance from the object that is less than the predetermined distance, the framing guides remain separated (FIG. 9A). When the lens of the imaging device 100 is positioned at distance from the object that is greater than the predetermined distance, the framing guides cross each other (FIG. 9B).

In various implementations, the framing guides represent all or substantially all the area of the object that will be captured by the imaging device 100. In various implementations, at least all of the object that falls inside the framing guides will be captured by the imaging device 100.

In various implementations, as illustrated in FIG. 8B, first projector 112-1 and second projector 112-2 are each configured to project a spot onto the object (e.g., spots 904-1 and 904-2, illustrated in FIG. 9D), such that the spots converge (e.g., at spot 904 in FIG. 9E) when the lens 104 is positioned at a predetermined distance from the object, the predetermined distance corresponding to a focus distance of the lens. When the lens of the imaging device 100 is positioned at distance from the object that is less than or greater than the predetermined distance, the projected spots diverge from each other (FIG. 9D).

FIG. 1B illustrates another imaging device 100, in accordance with various implementations, similar to that shown in FIG. 1A but including an integrated body 101 that resembles a digital single-lens reflex (DSLR) camera in that the body has a forward-facing lens assembly 104, and a rearward facing display 122. The DSLR-type housing allows a user to easily hold imaging device 100, aim it toward a patient and the region of interest (e.g., the skin of the patient), and position the device at an appropriate distance from the patient. One will appreciate that the implementation of FIG. 1B, may incorporate the various features described above and below in connection with the device of FIG. 1A.

In various implementations, and similar to the device described above, the imaging device 100 illustrated in FIG. 1B includes an optical assembly having a plurality of light source sets 106 for illuminating the surface of an object (e.g., the skin of a subject) and a lens assembly 104 for collecting light reflected and/or back scattered from the object.

In various implementations, and also similar to the device described above, the imaging device of FIG. 1B includes first and second projectors 112-1 and 112-2 configured to project light onto the object indicating when the imaging device 100 is positioned at an appropriate distance from the object to acquire a focused image. As noted above, this may be particularly useful where the lens assembly 104 has a fixed focal distance, such that the image cannot be brought into focus by manipulation of the lens assembly. As shown in FIG. 1B, the projectors are mounted on a forward side of body 101.

In various implementations, the body 101 substantially encases and supports the light source sets 106 and the lens assembly 104 of the optical assembly, along with the first and second projectors 112-1 and 112-2 and the display 122.

Figure 13:
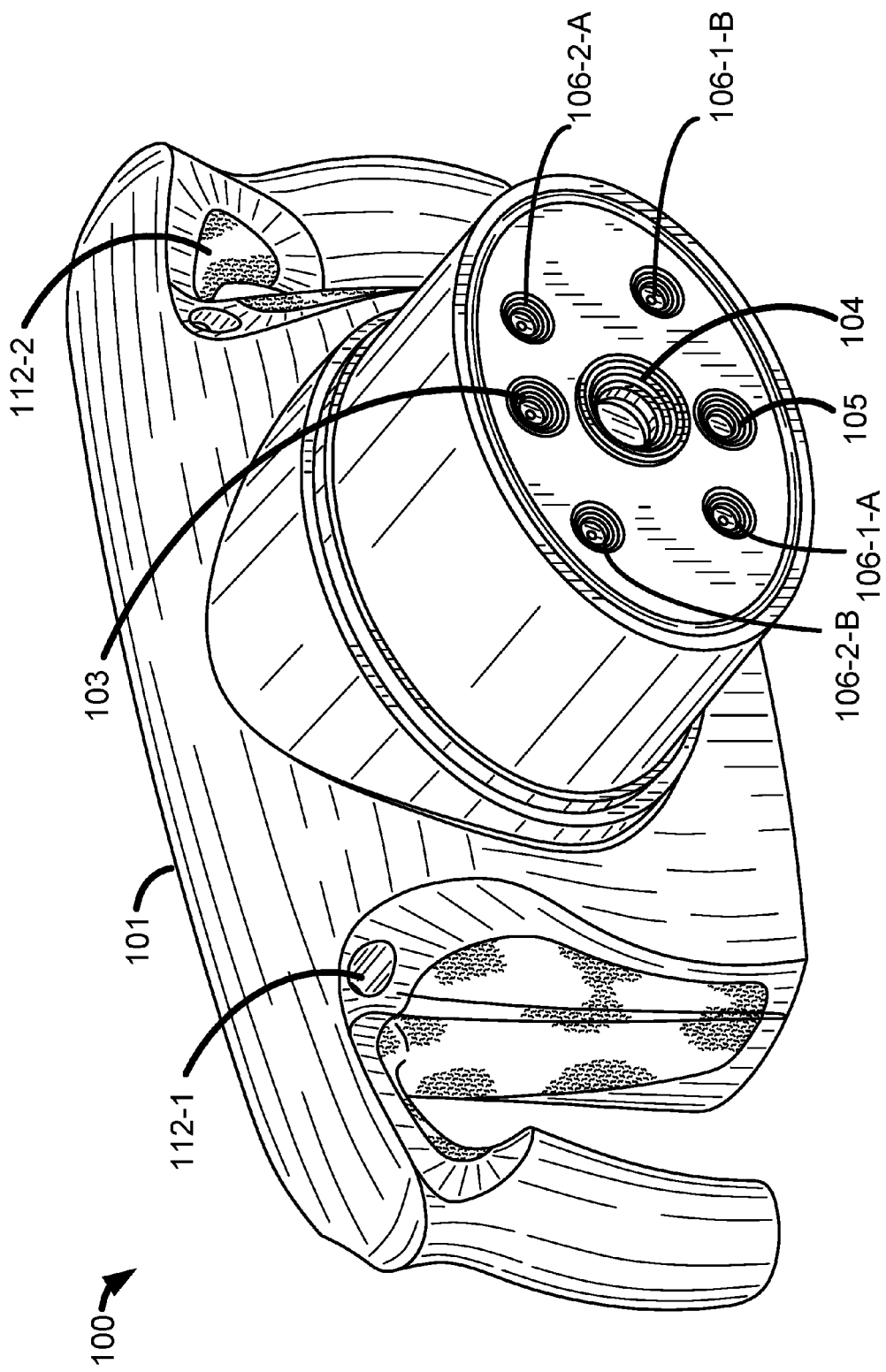
FIG. 13 is an illustration of a first view of another hyperspectral imaging device 100, in accordance with an implementation.
Figure 14:
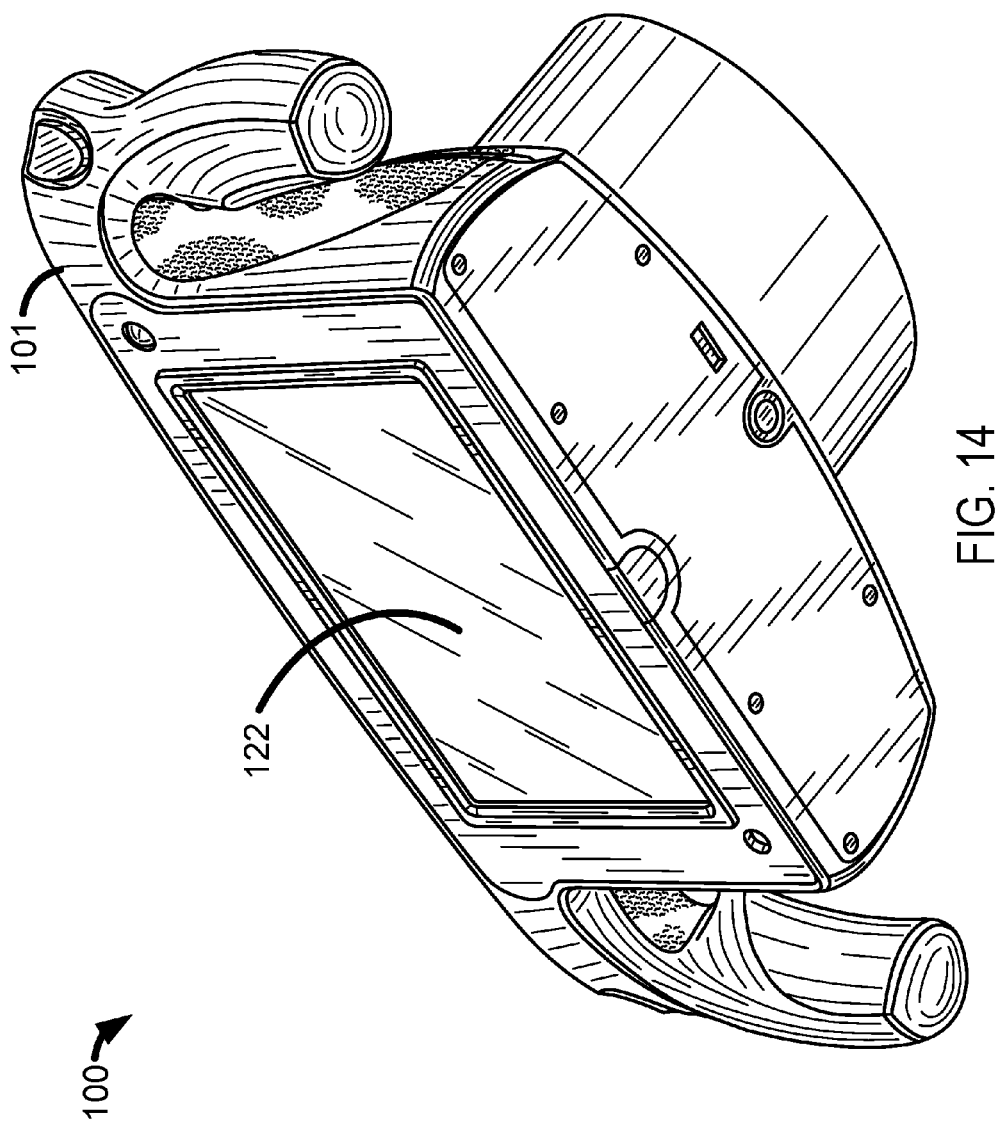
FIG. 14 is an illustration of a second view of the hyperspectral imaging device 100 of FIG. 13, in accordance with an implementation.

FIGS. 13 and 14 collectively illustrate another configuration for imaging device 100, in accordance with various implementations, similar to that shown in FIG. 1B but including more detail regarding an embodiment of integrated body 101 and forward-facing lens assembly 104, and a rearward facing display 122. The housing 101 allows a user to easily hold imaging device 100, aim it toward a patient and the region of interest (e.g., the skin of the patient), and position the device at an appropriate distance from the patient. One will appreciate that the implementation of FIGS. 13 and 14 may incorporate the various features described herein in connection with the device of FIGS. 1A and 1B.

In various implementations, and similar to the device described above, the imaging device 100 illustrated in FIGS. 13 and 14 includes an optical assembly and a plurality of light source sets 106 for illuminating the surface of an object (e.g., the skin of a subject) and a lens assembly 104 for collecting light reflected and/or back scattered from the object.

In various implementations, and also similar to the device described in FIGS. 1A and 1B, the imaging device of FIG. 13 includes first and second projectors 112-1 and 112-2 configured to project light onto the object indicating when the imaging device 100 is positioned at an appropriate distance from the object to acquire a focused image. As noted above, this may be particularly useful where the lens assembly 104 has a fixed focus distance, such that the image cannot be brought into focus by manipulation of the lens assembly. As shown in FIG. 13, the projectors are mounted on a forward side of body 101.

In various implementations, the body 101 substantially encases and supports the light sets 106 and the lens assembly 104 of the optical assembly, along with the first and second projectors 112-1 and 112-2. In various implementations, the imaging device 101 of FIG. 13 includes a live-view camera 103 and a remote thermometer 105.

FIG. 13 illustrates an embodiment in which the imaging device consist of two light source sets and the first light source set 106-1 in the two light source sets is arranged with respect to the at least one objective lens 104 so that the first light source 106-1-A of the first light source set opposes the first light source 106-2-A of the second light source set in the two light source sets, and the second light source 106-1-B of the first light source set opposes the second light source 106-2-B of the second light source set (across the objective lens).

Figure 15:
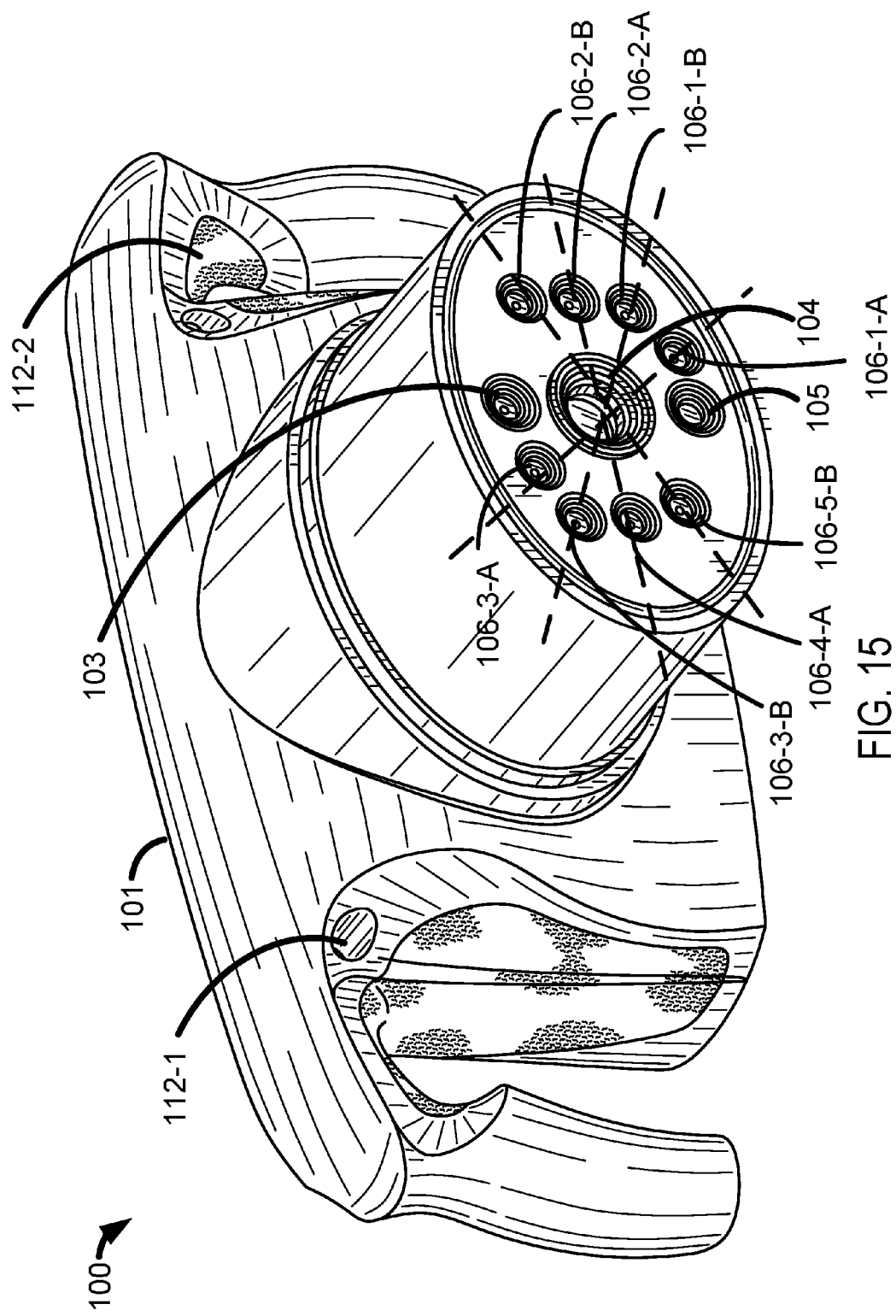
FIG. 15 is an illustration of a view of another hyperspectral imaging device 100, in accordance with an implementation.

FIG. 15 illustrates an embodiment in which the imaging device consist of four light source sets (106-1, 106-2, 106-3, and 104-5), and a first light source set 106-1 in the four light source sets is arranged with respect to the at least one objective lens 104 so that the first light source 106-1-A of the first light source set opposes the first light source 106-3-A of a second light source set 106-3 in the four light source sets, and the second light source 106-1-B of the first light source set opposes the second light source 106-3-B of the second light source set 103.

Figure 16:
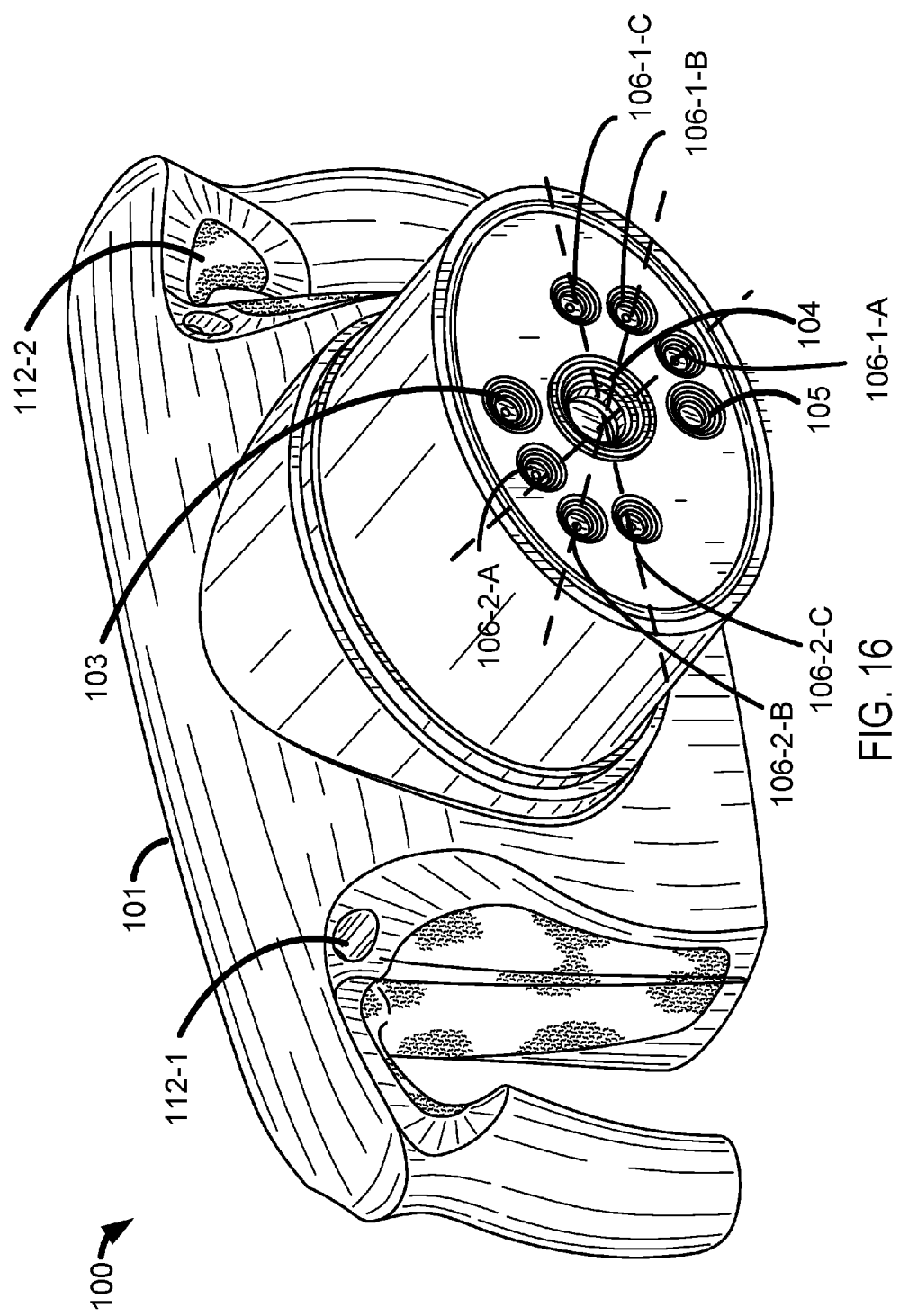
FIG. 16 is an illustration of a view of another hyperspectral imaging device 100, in accordance with an implementation.

FIG. 16 illustrates an embodiment in which the imaging device comprises two light source sets 106-1 and 106-2 and a first light source set 106-1 in the two light source sets is arranged with respect to the at least one objective lens 104 so that a first light source 106-1-A of the first light source set 106-1 opposes a first light source 106-2-A of the second light source set 106-2, a second light source 106-1-B of the first light source 106-1 set opposes a second light source 106-2-B of the second light source set 106-B, and a third light source 106-1-C of the first light source set 106-2 opposes a third light source 106-2-C of the second light source set 106-2-C with respect to the at least one objective lens 104. A first light (lights 106-1-A, 106-2-A) in each light source set in the plurality of light source sets is fired for a first period of time while not firing the other light source in each light source set. A first set of images is collected during the first period of time using at least a first subset of the plurality of pixel array photo-sensors. A second light (light 106-1-B, 106-2-B) in each light source set in the plurality of light source sets is fired for a second period of time while not firing the other light sources in each light source set. A second set of images is collected during the second period of time using at least a second subset of the plurality of pixel array photo-sensors. A third light (light 106-1-C, 106-2-C) in each light source set 106 in the plurality of light source sets is fired for a third period of time while not firing the other light sources in each light source set. A third set of images is collected during the third period of time using at least a third subset of the plurality of pixel array photo-sensors. It will be appreciated that each set of light sources may have any number of light sources (e.g., 2, 3, 4, 5, 6, 7, 8, or more).

Exemplary Optical Configurations

In one implementation, the imaging device 100 is configured to detect a set of spectral bands suitable for determining the oxyhemoglobin and deoxyhemoglobin distribution in a tissue. In a specific implementation, this is achieved by capturing images of the tissue of interest at eight different spectral bands. The images are captured in two exposures of four photo-sensors 210, each photo-sensor covered by a unique dual band pass filter 216. In one implementation, the imaging device 100 has a plurality of light source sets and a first light source in each respective light source set is configured to concurrently illuminate the tissue of interest with light including exactly four of the eight spectral bands, where each dual band pass filter 216 has exactly one pass band matching a spectral band in the four spectral bands emitted from the first light source in each light source set. Each second light in each respective light source set 106 is configured to concurrently illuminate the tissue of interest with light including the other four spectral bands of the set of eight spectral bands (e.g., but not the first four spectral bands), where each dual band pass filter 216 has exactly one pass band matching a spectral band in the four spectral bands emitted from second light source in each respective light source set.

In one implementation, the set of eight spectral bands includes spectral bands having central wavelengths of: 510±5 nm, 530±5 nm, 540±5 nm, 560±5 nm, 580±5 nm, 590±5 nm, 620±5 nm, and 660±5 nm, and each spectral band has a full width at half maximum of less than 15 nm. In a related implementation, the set of eight spectral bands includes spectral bands having central wavelengths of: 510±4 nm, 530±4 nm, 540±4 nm, 560±4 nm, 580±4 nm, 590±4 nm, 620±4 nm, and 660±4 nm, and each spectral band has a full width at half maximum of less than 15 nm. In a related implementation, the set of eight spectral bands includes spectral bands having central wavelengths of: 510±3 nm, 530±3 nm, 540±3 nm, 560±3 nm, 580±3 nm, 590±3 nm, 620±3 nm, and 660±3 nm, and each spectral band has a full width at half maximum of less than 15 nm. In a related implementation, the set of eight spectral bands includes spectral bands having central wavelengths of: 510±2 nm, 530±2 nm, 540±2 nm, 560±2 nm, 580±2 nm, 590±2 nm, 620±2 nm, and 660±2 nm, and each spectral band has a full width at half maximum of less than 15 nm. In a related implementation, the set of eight spectral bands includes spectral bands having central wavelengths of: 510±1 nm, 530±1 nm, 540±1 nm, 560±1 nm, 580±1 nm, 590±1 nm, 620±1 nm, and 660±1 nm, and each spectral band has a full width at half maximum of less than 15 nm. In a related implementation, the set of eight spectral bands includes spectral bands having central wavelengths of: 510 nm, 530 nm, 540 nm, 560 nm, 580 nm, 590 nm, 620 nm, and 660 nm, and each spectral band has a full width at half maximum of about 10 nm.

In one implementation, dual band filters having spectral pass bands centered at: (i) 520±5 and 590±5, (ii) 540±5 and 610±5, (iii) 560±5 and 620±5, and (iv) 580±5 and 640±5 are placed in front of photo-sensors configured to detect this particular set of wavelengths.

In one implementation, the imaging device has a plurality of light source sets and a first light source in each such light source set is configured to illuminate a tissue of interest with light having wavelengths from 450-585 nm in a first operation mode and a second light source in each respective light source set emits wavelengths from 585-650 nm in a second operation mode. In one implementation, the imaging device has a plurality of light source sets and a first light source in each respective light source set is configured to illuminate a tissue of interest with light having wavelengths from 450-585 nm, and a second light source in each respective light source set is configured to illuminate the tissue of interest with light having wavelengths from 585-650 nm.

In still another implementation, the imaging device has a plurality of light source sets and a first light source in each respective light source set is configured to illuminate a tissue of interest with light having wavelengths 520, 540, 560 and 640 but not wavelengths 580, 590, 610 and 620 and a second light source in each respective light source set is configured to illuminate the tissue of interest with light having wavelengths 580, 590, 610, and 620 but not wavelengths 520, 540, 560 and 640.

In one implementation, dual band filters having spectral pass bands centered at: (i) 520±5 and 560±5, (ii) 540±5 and 580±5, (iii) 590±5 and 620±5, and (iv) 610 and 640±5 are placed in front of photo-sensors configured to detect this particular set of wavelengths. In one implementation, the imaging device has a plurality of light source sets and a first light source in each such respective light source set is configured to illuminate a tissue of interest with light having wavelengths from 450-550 nm and from 615-650 nm in a first operation mode and a second light source in each respective light source set emits wavelengths from 550-615 nm in a second operation mode.

In one implementation, the imaging device has a plurality of light source sets and a first light source in each respective light source is configured to illuminate a tissue of interest with light having wavelengths from 450-550 nm and from 615-650 nm, and a second light source in each respective light source set is configured to illuminate the tissue of interest with light having wavelengths from 585-650 nm.

In one implementation, dual band filters having spectral pass bands centered at: (i) 520±5 and 560±5, (ii) 540±5 and 610±5, (iii) 590±5 and 620±5, and (iv) 580 and 640±5 are placed in front of photo-sensors configured to detect this particular set of wavelengths. In one implementation, the imaging device has a plurality of light source sets and a first light source in each light source set is configured to illuminate a tissue of interest with light having wavelengths from 450-530 nm and from 600-650 nm in a first operation mode and second light source in each respective light source set is configured to emits wavelengths from 530-600 nm in a second operation mode. In one implementation, the imaging device has a plurality of light source sets and a first light source in each respective light source set is configured to illuminate a tissue of interest with light having wavelengths from 450-530 nm and from 600-650 nm, and a second light source in each respective light source set is configured to illuminate the tissue of interest with light having wavelengths from 530-600.

In one implementation, the set of eight spectral bands includes spectral bands having central wavelengths of: 520±5 nm, 540±5 nm, 560±5 nm, 580±5 nm, 590±5 nm, 610±5 nm, 620±5 nm, and 640±5 nm, and each spectral band has a full width at half maximum of less than 15 nm. In a related implementation, the set of eight spectral bands includes spectral bands having central wavelengths of: 520±4 nm, 540±4 nm, 560±4 nm, 580±4 nm, 590±4 nm, 610±4 nm, 620±4 nm, and 640±4 nm, and each spectral band has a full width at half maximum of less than 15 nm. In a related implementation, the set of eight spectral bands includes spectral bands having central wavelengths of: 520±3 nm, 540±3 nm, 560±3 nm, 580±3 nm, 590±3 nm, 610±3 nm, 620±3 nm, and 640±3 nm, and each spectral band has a full width at half maximum of less than 15 nm. In a related implementation, the set of eight spectral bands includes spectral bands having central wavelengths of: 520±2 nm, 540±2 nm, 560±2 nm, 580±2 nm, 590±2 nm, 610±2 nm, 620±2 nm, and 640±2 nm, and each spectral band has a full width at half maximum of less than 15 nm. In a related implementation, the set of eight spectral bands includes spectral bands having central wavelengths of: 520±1 nm, 540±1 nm, 560±1 nm, 580±1 nm, 590±1 nm, 610±1 nm, 620±1 nm, and 640±1 nm, and each spectral band has a full width at half maximum of less than 15 nm. In a related implementation, the set of eight spectral bands includes spectral bands having central wavelengths of: 520 nm, 540 nm, 560 nm, 580 nm, 590 nm, 610 nm, 620 nm, and 640 nm, and each spectral band has a full width at half maximum of about 10 nm.

In one implementation, the set of eight spectral bands includes spectral bands having central wavelengths of: 500±5 nm, 530±5 nm, 545±5 nm, 570±5 nm, 585±5 nm, 600±5 nm, 615±5 nm, and 640±5 nm, and each spectral band has a full width at half maximum of less than 15 nm. In a related implementation, the set of eight spectral bands includes spectral bands having central wavelengths of: 500±4 nm, 530±4 nm, 545±4 nm, 570±4 nm, 585±4 nm, 600±4 nm, 615±4 nm, and 640±4 nm, and each spectral band has a full width at half maximum of less than 15 nm. In a related implementation, the set of eight spectral bands includes spectral bands having central wavelengths of: 500±3 nm, 530±3 nm, 545±3 nm, 570±3 nm, 585±3 nm, 600±3 nm, 615±3 nm, and 640±3 nm, and each spectral band has a full width at half maximum of less than 15 nm. In a related implementation, the set of eight spectral bands includes spectral bands having central wavelengths of: 500±2 nm, 530±2 nm, 545±2 nm, 570±2 nm, 585±2 nm, 600±2 nm, 615±2 nm, and 640±2 nm, and each spectral band has a full width at half maximum of less than 15 nm. In a related implementation, the set of eight spectral bands includes spectral bands having central wavelengths of: 500±1 nm, 530±1 nm, 545±1 nm, 570±1 nm, 585±1 nm, 600±1 nm, 615±1 nm, and 640±1 nm, and each spectral band has a full width at half maximum of less than 15 nm. In a related implementation, the set of eight spectral bands includes spectral bands having central wavelengths of: 500 nm, 530 nm, 545 nm, 570 nm, 585 nm, 600 nm, 615 nm, and 640 nm, and each spectral band has a full width at half maximum of about 10 nm.

In other implementations, the imaging devices described here are configured for imaging more or less than eight spectral bands. For example, in some implementations, the imaging device is configured for imaging 3, 4, 5, 6, 7, 8, 9, 10, 11, 12, 13, 14, 15, 16, 17, 18, 19, 20, 21, 22, 23, 24, or more spectral bands. For example, imaging devices including 7 beam splitters and eight photo-sensors can be configured according to the principles described herein to capture eight images concurrently, 16 images in two exposures (e.g., by placing dual band pass filters in from of each photosensor), and 24 images in three exposures (e.g., by placing triple band pass filters in front of each photosensor). In fact, the number of spectral band passes that can be imaged using the principles disclosed herein is only constrained by any desired size of the imager, desired exposure times, and light sources employed. Of course, one or more photo-sensors may not be used in any given exposure. For example, in an imaging device employing four photo sensors and three beam splitters, seven images can be captured in two exposures by not utilizing one of the photo-sensors in one of the exposures. Thus, imaging devices employing any combination of light sources (e.g., 1, 2, 3, 4, or more), beam splitters (e.g., 1, 2, 3, 4, 5, 6, 7, or more), and photo-sensors (e.g., 1, 2, 3, 4, 5, 6, 7, 8, or more) are contemplated.

Optimization of Exposure Time

Many advantages of the imaging systems and methods described herein are derived, at least in part, from the use of in-band illumination and detection across multiple spectral bands. For example, in-band illumination allows for greater signal-to-noise ratio and reduced exposure times, which in turn results in lower power consumption, reduced misalignment due to movement of the subject, and reduced computational burden when processing the resulting hyperspectral data cubes.

These advantages can be further enhanced by minimizing the exposure time (e.g., shutter speed) needed to provide a suitable signal-to-noise ratio at each wavelength imaged. The minimum exposure time needed to resolve a suitable image at each wavelength will depend upon, at least, the sensitivity of the optical detector for the particular wavelength, the characteristics and intensity of ambient light present when acquiring images, and the concentration of melanin in the skin/tissue being imaged.

In one embodiment, the imaging systems described herein advantageously reduces the total amount of time required to collect a complete image series by determining the specific exposure time needed to resolve each sub-image of the image series. Each image in the image series is collected at a different spectral band and, because of this, the amount of time needed to resolve each sub-image will vary as a function of wavelength. In some embodiments, this variance is advantageously taken into account so that an image requiring less time, because of their acquisition wavelengths or wavelength bands, are allotted shorter exposure times whereas images that require more time because of their acquisition wavelengths or wavelength bands, are allotted shorter exposure times. This novel improvement affords a faster overall exposure time because each of images in the series of images is only allocated an amount of time needed for full exposure, rather than a "one size fits all" exposure time. This also reduces the power requirement of the imaging device, because the illumination, which requires a large amount of power, is shortened. In a specific embodiment, non-transitory instructions encoded by the imager in non-transient memory determine the minimal exposure time required for image acquisition at each spectral band acquired by the imaging system.

In some embodiments, the methods and systems described herein include executable instructions for identifying a plurality of baseline exposure times, each respective baseline exposure time in the plurality of baseline exposure times representing an exposure time for resolving a respective image, in the series of images of the tissue being collected. A first baseline exposure time for a first image is different than a second baseline exposure time of a second image in the plurality of images.

In one embodiment, a method is provided for acquiring an image series of a tissue of a patient, including selecting a plurality of spectral bands for acquiring an image series of a tissue, identifying minimum exposure times for resolving an image of the tissue at each spectral band, identifying at least one factor affecting one of more minimum exposure times, adjusting the minimum exposure times based on the identified factors, and acquiring a series of images of the tissue using the adjusted minimum exposure times.

In some embodiments, the minimum exposure times are based on baseline illumination of the tissue and/or the sensitivity of an optical detector acquiring the image.

In some embodiments, the factor affecting the minimal exposure time is one or more of illumination provided by a device used to acquire the image series, ambient light, and concentration of melanin in the tissue.

Hyperspectral Imaging

Hyperspectral and multispectral imaging are related techniques in larger class of spectroscopy commonly referred to as spectral imaging or spectral analysis. Typically, hyperspectral imaging relates to the acquisition of a plurality of images, each image representing a narrow spectral band collected over a continuous spectral range, for example, 5 or more (e.g., 5, 10, 15, 20, 25, 30, 40, 50, or more) spectral bands having a FWHM bandwidth of 1 nm or more each (e.g., 1 nm, 2 nm, 3 nm, 4 nm, 5 nm, 10 nm, 20 nm or more), covering a contiguous spectral range (e.g., from 400 nm to 800 nm). In contrast, multispectral imaging relates to the acquisition of a plurality of images, each image representing a narrow spectral band collected over a discontinuous spectral range.

For the purposes of the present disclosure, the terms "hyperspectral" and "multispectral" are used interchangeably and refer to a plurality of images, each image representing a narrow spectral band (having a FWHM bandwidth of between 10 nm and 30 nm, between 5 nm and 15 nm, between 5 nm and 50 nm, less than 100 nm, between 1 and 100 nm, etc.), whether collected over a continuous or discontinuous spectral range. For example, in various implementations, wavelengths 1-N of a hyperspectral data cube 1336-1 are contiguous wavelengths or spectral bands covering a contiguous spectral range (e.g., from 400 nm to 800 nm). In other implementations, wavelengths 1-N of a hyperspectral data cube 1336-1 are non-contiguous wavelengths or spectral bands covering a non-contiguous spectral ranges (e.g., from 400 nm to 440 nm, from 500 nm to 540 nm, from 600 nm to 680 nm, and from 900 to 950 nm).

As used herein, "narrow spectral range" refers to a continuous span of wavelengths, typically consisting of a FWHM spectral band of no more than about 100 nm. In certain embodiments, narrowband radiation consists of a FWHM spectral band of no more than about 75 nm, 50 nm, 40 nm, 30 nm, 25 nm, 20 nm, 15 nm, 10 nm, 5 nm, 4 nm, 3 nm, 2 nm, 1 nm, or less. In various implementations, wavelengths imaged by the methods and devices disclosed herein are selected from one or more of the visible, near-infrared, short-wavelength infrared, mid-wavelength infrared, long-wavelength infrared, and ultraviolet (UV) spectrums.

By "broadband" it is meant light that includes component wavelengths over a substantial portion of at least one band, for example, over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. In certain embodiments, broadband light includes component wavelengths across at least 100 nm of the electromagnetic spectrum. In other embodiments, broadband light includes component wavelengths across at least 150 nm, 200 nm, 250 nm, 300 nm, 400 nm, 500 nm, 600 nm, 700 nm, 800 nm, or more of the electromagnetic spectrum.

By "narrowband" it is meant light that includes components over only a narrow spectral region, for example, less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, for example, may together constitute a broadband light source. In certain embodiments, broadband light includes component wavelengths across no more than 100 nm of the electromagnetic spectrum (e.g., has a spectral bandwidth of no more than 100 nm). In other embodiments, narrowband light has a spectral bandwidth of no more than 90 nm, 80 nm, 75 nm, 70 nm, 60 nm, 50 nm, 40 nm, 30 nm, 25 nm, 20 nm, 15 nm, 10 nm, 5 nm, or less of the electromagnetic spectrum.

As used herein, the "spectral bandwidth" of a light source refers to the span of component wavelengths having an intensity that is at least half of the maximum intensity, otherwise known as "full width at half maximum" (FWHM) spectral bandwidth. Many light emitting diodes (LEDs) emit radiation at more than a single discreet wavelength, and are thus narrowband emitters. Accordingly, a narrowband light source can be described as having a "characteristic wavelength" or "center wavelength," for example, the wavelength emitted with the greatest intensity, as well as a characteristic spectral bandwidth, for example, the span of wavelengths emitted with an intensity of at least half that of the characteristic wavelength.

By "coherent light source" it is meant a light source that emits electromagnetic radiation of a single wavelength in phase. Thus, a coherent light source is a type of narrowband light source with a spectral bandwidth of less than 1 nm. Non-limiting examples of coherent light sources include lasers and laser-type LEDs. Similarly, an incoherent light source emits electromagnetic radiation having a spectral bandwidth of more than 1 nm and/or is not in phase. In this regard, incoherent light can be either narrowband or broadband light, depending on the spectral bandwidth of the light.

Examples of suitable broadband light sources 106 include, without limitation, incandescent lights such as a halogen lamp, xenon lamp, a hydrargyrum medium-arc iodide lamp, and a broadband light emitting diode (LED). In some embodiments, a standard or custom filter is used to balance the light intensities at different wavelengths to raise the signal level of certain wavelength or to select for a narrowband of wavelengths. Broadband illumination of a subject is particularly useful when capturing a color image of the subject or when focusing the hyperspectral/multispectral imaging system.

Examples of suitable narrowband, incoherent light sources 106 include, without limitation, a narrow band light emitting diode (LED), a superluminescent diode (SLD) (see, Redding, B. et al, "Speckle-free laser imaging", arVix: 1110.6860 (2011), the content of which is hereby incorporated herein by reference in its entirety for all purposes), a random laser, and a broadband light source covered by a narrow band-pass filter. Examples of suitable narrowband, coherent light sources 104 include, without limitation, lasers and laser-type light emitting diodes. While both coherent and incoherent narrowband light sources 104 can be used in the imaging systems described herein, coherent illumination is less well suited for full-field imaging due to speckle artifacts that corrupt image formation (see, Oliver, B. M., "Sparkling spots and random diffraction", Proc IEEE 51, 220-221 (1963)).

Hyperspectral Medical Imaging

Various implementations of the present disclosure provide for systems and methods useful for hyperspectral/multispectral medical imaging (HSMI). HSMI relies upon distinguishing the interactions that occur between light at different wavelengths and components of the human body, especially components located in or just under the skin. For example, it is well known that deoxyhemoglobin absorbs a greater amount of light at 700 nm than does water, while water absorbs a much greater amount of light at 1200 nm, as compared to deoxyhemoglobin. By measuring the absorbance of a two-component system consisting of deoxyhemoglobin and water at 700 nm and 1200 nm, the individual contribution of deoxyhemoglobin and water to the absorption of the system, and thus the concentrations of both components, can readily be determined. By extension, the individual components of more complex systems (e.g., human skin) can be determined by measuring the absorption of a plurality of wavelengths of light reflected or backscattered off of the system.

The particular interactions between the various wavelengths of light measured by hyperspectral/multispectral imaging and each individual component of the system (e.g., skin) produces hyperspectral/multispectral signature, when the data is constructed into a hyperspectral/multispectral data cube. Specifically, different regions (e.g., different regions of interest or ROI on a single subject or different ROIs from different subjects) interact differently with light depending on the presence of, e.g., a medical condition in the region, the physiological structure of the region, and/or the presence of a chemical in the region. For example, fat, skin, blood, and flesh all interact with various wavelengths of light differently from one another. A given type of cancerous lesion interacts with various wavelengths of light differently from normal skin, from non-cancerous lesions, and from other types of cancerous lesions. Likewise, a given chemical that is present (e.g., in the blood, or on the skin) interacts with various wavelengths of light differently from other types of chemicals. Thus, the light obtained from each illuminated region of a subject has a spectral signature based on the characteristics of the region, which signature contains medical information about that region.

The structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the content of which is incorporated herein by reference in its entirety for all purposes.

The dermis has a dense collection of collagen fibers and blood vessels, and its optical properties are very different from that of the epidermis. Absorption of light of a bloodless dermis is negligible. However, blood-born pigments like oxy- and deoxyhemoglobin and water are major absorbers of light in the dermis. Scattering by the collagen fibers and absorption due to chromophores in the dermis determine the depth of penetration of light through skin.

Light used to illuminate the surface of a subject will penetrate into the skin. The extent to which the light penetrates will depend upon the wavelength of the particular radiation. For example, with respect to visible light, the longer the wavelength, the farther the light will penetrate into the skin. For example, only about 32% of 400 nm violet light penetrates into the dermis of human skin, while greater than 85% of 700 nm red light penetrates into the dermis or beyond (see, Capinera J. L., "Photodynamic Action in Pest Control and Medicine", Encyclopedia of Entomology, 2nd Edition, Springer Science, 2008, pp. 2850-2862, the content of which is hereby incorporated herein by reference in its entirety for all purposes). For purposes of the present disclosure, when referring to "illuminating a tissue," "reflecting light off of the surface," and the like, it is meant that radiation of a suitable wavelength for detection is backscattered from a tissue of a subject, regardless of the distance into the subject the light travels. For example, certain wavelengths of infra-red radiation penetrate below the surface of the skin, thus illuminating the tissue below the surface of the subject.

Briefly, light from the illuminator(s) on the systems described herein penetrates the subject's superficial tissue and photons scatter in the tissue, bouncing inside the tissue many times. Some photons are absorbed by oxygenated hemoglobin molecules at a known profile across the spectrum of light. Likewise for photons absorbed by de-oxygenated hemoglobin molecules. The images resolved by the optical detectors consist of the photons of light that scatter back through the skin to the lens subsystem. In this fashion, the images represent the light that is not absorbed by the various chromophores in the tissue or lost to scattering within the tissue. In some embodiments, light from the illuminators that does not penetrate the surface of the tissue is eliminated by use of polarizers. Likewise, some photons bounce off the surface of the skin into air, like sunlight reflecting off a lake.

Accordingly, different wavelengths of light may be used to examine different depths of a subject's skin tissue. Generally, high frequency, short-wavelength visible light is useful for investigating elements present in the epidermis, while lower frequency, long-wavelength visible light is useful for investigating both the epidermis and dermis. Furthermore, certain infra-red wavelengths are useful for investigating the epidermis, dermis, and subcutaneous tissues.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see Anderson, R. R. et al., "The Optics of Human Skin", Journal of Investigative Dermatology, 77, pp. 13-19, 1981, the content of which is hereby incorporated by reference in its entirety for all purposes. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Accordingly, the systems and methods described herein can be used to diagnose and characterize a wide variety of medical conditions. In one embodiment, the concentration of one or more skin or blood component is determined in order to evaluate a medical condition in a patient. Non-limiting examples of components useful for medical evaluation include: deoxyhemoglobin levels, oxyhemoglobin levels, total hemoglobin levels, oxygen saturation, oxygen perfusion, hydration levels, total hematocrit levels, melanin levels, collagen levels, and bilirubin levels. Likewise, the pattern, gradient, or change over time of a skin or blood component can be used to provide information on the medical condition of the patient.

Non-limiting examples of conditions that can be evaluated by hyperspectral/multispectral imaging include: tissue ischemia, ulcer formation, ulcer progression, pressure ulcer formation, pressure ulcer progression, diabetic foot ulcer formation, diabetic foot ulcer progression, venous stasis, venous ulcer disease, peripheral artery disease, atherosclerosis, infection, shock, cardiac decompensation, respiratory insufficiency, hypovolemia, the progression of diabetes, congestive heart failure, sepsis, dehydration, hemorrhage, hemorrhagic shock, hypertension, cancer (e.g., detection, diagnosis, or typing of tumors or skin lesions), retinal abnormalities (e.g., diabetic retinopathy, macular degeneration, or corneal dystrophy), skin wounds, burn wounds, exposure to a chemical or biological agent, and an inflammatory response.

In various embodiments, the systems and methods described herein are used to evaluate tissue oximetery and correspondingly, medical conditions relating to patient health derived from oxygen measurements in the superficial vasculature. In certain embodiments, the systems and methods described herein allow for the measurement of oxygenated hemoglobin, deoxygenated hemoglobin, oxygen saturation, and oxygen perfusion. Processing of these data provide information to assist a physician with, for example, diagnosis, prognosis, assignment of treatment, assignment of surgery, and the execution of surgery for conditions such as critical limb ischemia, diabetic foot ulcers, pressure ulcers, peripheral vascular disease, surgical tissue health, etc.

In various embodiments, the systems and methods described herein are used to evaluate diabetic and pressure ulcers. Development of a diabetic foot ulcer is commonly a result of a break in the barrier between the dermis of the skin and the subcutaneous fat that cushions the foot during ambulation. This rupture can lead to increased pressure on the dermis, resulting in tissue ischemia and eventual death, and ultimately manifesting in the form of an ulcer (Frykberg R. G. et al., "Role of neuropathy and high foot pressures in diabetic foot ulceration", Diabetes Care, 21(10), 1998:1714-1719). Measurement of oxyhemoglobin, deoxyhemoglobin, and/or oxygen saturation levels by hyperspectral/multispectral imaging can provide medical information regarding, for example: a likelihood of ulcer formation at an ROI, diagnosis of an ulcer, identification of boundaries for an ulcer, progression or regression of ulcer formation, a prognosis for healing of an ulcer, the likelihood of amputation resulting from an ulcer. Further information on hyperspectral/multispectral methods for the detection and characterization of ulcers, e.g., diabetic foot ulcers, are found in U.S. Patent Application Publication No. 2007/0038042, and Nouvong, A. et al., "Evaluation of diabetic foot ulcer healing with hyperspectral imaging of oxyhemoglobin and deoxyhemoglobin", Diabetes Care. 2009 November; 32(11):2056-2061, the contents of which are hereby incorporated herein by reference in their entireties for all purposes.

Other examples of medical conditions include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Various embodiments may include differentiating different types of tissue from each other, for example, differentiating bone from flesh, skin, and/or vasculature. Various embodiments may exclude the characterization of vasculature.

In various embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., "Assessment of renal oxygenation during partial nephrectomy using hyperspectral imaging", J Urol. 2011 August; 186(2):400-4; Gibbs-Strauss S. L. et al., "Nerve-highlighting fluorescent contrast agents for image-guided surgery", Mol Imaging. 2011 April; 10(2):91-101; and Panasyuk S. V. et al., "Medical hyperspectral imaging to facilitate residual tumor identification during surgery", Cancer Biol Ther. 2007 March; 6(3):439-46, the contents of which are hereby incorporated herein by reference in their entirety for all purposes.

For more information on the use of hyperspectral/multispectral imaging in medical assessments, see, for example: Chin J. A. et al., J Vasc Surg. 2011 December; 54(6):1679-88; Khaodhiar L. et al., Diabetes Care 2007; 30:903-910; Zuzak K. J. et al., Anal Chem. 2002 May 1; 74(9):2021-8; Uhr J. W. et al., Transl Res. 2012 May; 159(5):366-75; Chin M. S. et al., J Biomed Opt. 2012 February; 17(2):026010; Liu Z. et al., Sensors (Basel). 2012; 12(1):162-74; Zuzak K. J. et al., Anal Chem. 2011 Oct. 1; 83(19):7424-30; Palmer G. M. et al., J Biomed Opt. 2010 November-December; 15(6):

066021; Jafari-Saraf and Gordon, Ann Vasc Surg. 2010 August; 24(6):741-6; Akbari H. et al., IEEE Trans Biomed Eng. 2010 August; 57(8):2011-7; Akbari H. et al., Conf Proc IEEE Eng Med Biol Soc. 2009:1461-4; Akbari H. et al., Conf Proc IEEE Eng Med Biol Soc. 2008:1238-41; Chang S. K. et al., Clin Cancer Res. 2008 Jul. 1; 14(13):4146-53; Siddiqi A. M. et al., Cancer. 2008 Feb. 25; 114(1):13-21; Liu Z. et al., Appl Opt. 2007 Dec. 1; 46(34):8328-34; Zhi L. et al., Comput Med Imaging Graph. 2007 December; 31(8): 672-8; Khaodhiar L. et al., Diabetes Care. 2007 April; 30(4):903-10; Ferris D. G. et al., J Low Genit Tract Dis. 2001 April; 5(2):65-72; Greenman R. L. et al., Lancet. 2005 November 12; 366(9498):1711-7; Sorg B. S. et al., J Biomed Opt. 2005 July-August; 10(4):44004; Gillies R. et al., and Diabetes Technol Ther. 2003; 5(5):847-55, the contents of which are hereby incorporated herein by reference in their entirety for all purposes.

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An imaging device, comprising:
    A) a housing having an exterior and an interior;
    B) at least one objective lens attached to or within the housing,
    C) a plurality of light source sets radially disposed on the exterior of the housing about the at least one objective lens, wherein
        each light source set in the plurality of light source sets comprises a first light source that emits light that is substantially limited to a first spectral range and a second light source that emits light that is substantially limited to a second spectral range,
        each light source in each light source set in the plurality of light source sets is offset from the at least one objective lens and positioned so that light from each respective light source is backscattered by a tissue of a subject and then passed through the at least one objective lens, and
        each light in each light source set has a different radial position with respect to the at least one objective lens;
    D) a plurality of pixel array photo-sensors within the housing;
    E) an optical assembly within the interior of the housing, the optical assembly in optical communication with the at least one objective lens, the optical assembly characterized by further directing light received by at least one objective lens from the tissue of the subject to at least one pixel array photo-sensor in the plurality of pixel array photo-sensors;
    F) a plurality of multi-bandpass filters, wherein each respective multi-bandpass filter in the plurality of multi-bandpass filters covers a corresponding pixel array photo-sensor in the plurality of pixel array photo-sensors thereby selectively allowing a different corresponding spectral band of light, from the light received by the at least one object lens and redirected by the optical assembly, to pass through to the corresponding pixel array photo-sensor; and
    G) a controller, wherein at least one program is non-transiently stored in the controller and executable by the controller, the at least one program causing the controller to perform the method of:
        i) firing a first light in each light source set in the plurality of light source sets for a first period of time while not firing the second light source in each light source set,
        ii) collecting a first set of images during the first period of time using at least a first subset of the plurality of pixel array photo-sensors,
        iii) firing a second light in each light source set in the plurality of light source sets for a second period of time while not firing the first light source in each light source set, and
        iv) collecting a second set of images during the second period of time using at least a second subset of the plurality of pixel array photo-sensors.

2. The imaging device of claim 1, wherein the optical assembly element comprises a plurality of beam splitters in optical communication with the at least one objective lens and the plurality of pixel array photo-sensors,
    each respective beam splitter in the plurality of beam splitters is configured to split the light received by the at least one objective lens into at least two optical paths,
    a first beam splitter in the plurality of beam splitters is in direct optical communication with the at least one objective lens and a second beam splitter in the plurality of beam splitters is in indirect optical communication with the at least one objective lens through the first beam splitter, and the plurality of beam splitters collectively split light received by the at least one objective lens into a plurality of optical paths, wherein each respective optical path in the plurality of optical paths is configured to direct light to a corresponding pixel array photo-sensor in the plurality of pixel array photo-sensors through the respective multi-bandpass filter covering the corresponding pixel array photo-sensor.

3. The imaging device of claim 1, wherein the optical assembly comprises a beam steering element characterized by a plurality of operating modes, each respective operating mode in the plurality of operating modes causing the beam steering element to be in optical communication with a different pixel array photo-sensor in the plurality of pixel array photo-sensors, a first subset of the plurality of operating modes are associated with firing a first light in each light source set in the plurality of light source sets in the first period of time, and a second subset of the plurality of operating modes are associated with firing a second light in each light source set in the plurality of light source sets in the second period of time.

4. The imaging device of claim 1, wherein the plurality of multi-bandpass filters are dual bandpass filters.

5. The imaging device of claim 1, wherein the plurality of light source sets consist of two light source sets, and a first light source set in the two light source sets is arranged with respect to the at least one objective lens so that the first light source of the first light source set opposes the first light source of the second light source set in the two light source sets, and the second light source of the first light source set opposes the second light source of the second light source set.

6. The imaging device of claim 1, wherein the plurality of light source sets consist of four light source sets, and a first light source set in the four light source sets is arranged with respect to the at least one objective lens so that the first light source of the first light source set opposes the first light source of a second light source set in the four light source sets, and the second light source of the first light source set opposes the second light source of the second light source set.

7. The imaging device of claim 1, wherein the plurality of light source sets consist of 2N light source sets, wherein N is a positive integer, and a first light source set in the 2N light source sets is arranged with respect to the at least one objective lens so that the first light source of the first light source set opposes the first light source of the second light source set in the 2N light source sets, and the second light source of the first light source set opposes the second light source of the second light source set.

8. The imaging device of claim 1, wherein the plurality of light source sets collectively comprises a plurality of first light sources and a plurality of second light sources, the first plurality of first light sources are uniformly radially distributed about the at least one objective lens, and the plurality of second light sources are uniformly radially distributed about the at least one objective lens.

9. The imaging device of claim 8, wherein the plurality of first light sources are radially offset from the plurality of second light sources.

10. The imaging device of claim 8, wherein the plurality of light source sets consists of three light source sets.

11. The imaging device of claim 8, wherein the plurality of light source sets comprises four or more light source sets.

12. The imaging device of claim 1, wherein the first light source of each light source set in the plurality of light source sets is a first multi-spectral light source covered by a first bandpass filter, wherein the first bandpass filter substantially blocks all light emitted by the first light source other than the first spectral range, and the second light source of each light source set in the plurality of light source sets is a second multi-spectral light source covered by a second bandpass filter, wherein the second bandpass filter substantially blocks all light emitted by the second light source other than the second spectral range.

13. The imaging device of claim 12, wherein the first multi-spectral light source is a first white light emitting diode and the second multi-spectral light source is a second white light emitting diode.

14. The imaging device of claim 1, wherein each respective multi-bandpass filter in the plurality of multi-bandpass filters is configured to selectively allow light corresponding to either of two discrete spectral bands to pass through to the corresponding pixel array photo-sensor.

15. The imaging device of claim 14, wherein:

a first of the two discrete spectral bands corresponds to a first spectral band that is represented in the first spectral range and not in the second spectral range; and a second of the two discrete spectral bands corresponds to a second spectral band that is represented in the second spectral range and not in the first spectral range.

16. The imaging device of claim 1, wherein the first spectral range is substantially non-overlapping with the second spectral range.

17. The imaging device of claim 1, wherein the first spectral range is substantially contiguous with the second spectral range.

18. The imaging device of claim 1, wherein the first spectral range comprises 520 nm, 540 nm, 560 nm and 640 nm wavelength light and does not include 580 nm, 590 nm, 610 nm and 620 nm wavelength light, and the second spectral range comprises 580 nm, 590 nm, 610 nm and 620 nm wavelength light and does not include 520 nm, 540 nm, 560 nm and 640 nm wavelength light.

19. The imaging device of claim 3, the optical assembly further comprising a plurality of beam steering elements, each respective beam steering element configured to direct light in a respective optical path to a respective pixel array photo-sensor, of the plurality of pixel array photo-sensors, corresponding to the respective optical path.

20. The imaging device of claim 19, wherein each one of a first subset of the plurality of beam steering elements is configured to direct light in a first direction that is perpendicular to the direction of the light received by the plurality of beam steering elements from the at least one objective lens, and each one of a second subset of the plurality of beam steering elements is configured to direct light in a second direction that is perpendicular to the light received by the plurality of beam steering elements and opposite to the first direction.

21. The imaging device of claim 1, wherein
the first set of images includes, for each respective pixel array photo-sensor in the plurality of pixel array photo-sensors, an image corresponding to a first spectral band transmitted by the corresponding multi-bandpass filter, wherein the light falling within the first spectral range includes light falling within the first spectral band of each multi-bandpass filter in the plurality of multi-bandpass filters, and
wherein the second set of images includes, for each respective pixel array photo-sensor in the plurality of pixel array photo-sensors, an image corresponding to a second spectral band transmitted by the corresponding multi-bandpass filter, wherein the light falling within the second spectral range includes light falling within the second spectral band of each multi-bandpass filter in the plurality of multi-bandpass filters.

22. The imaging device of claim 21, wherein
each respective pixel array photo-sensor in the plurality of pixel array photo-sensors is a pixel array that is controlled by a corresponding shutter mechanism that determines an image integration time for the respective pixel array photo-sensor, and
a first pixel array photo-sensor in the plurality of pixel array photo-sensors is independently associated with a first integration time for use during the collecting ii) and a second integration time for use during the collecting iv), wherein the first integration time is independent of the second integration time.

23. The imaging device of claim 2, wherein each beam splitter in the plurality of beam splitters exhibits a ratio of light transmission to light reflection of about 50:50.

24. The imaging device of claim 23, wherein each respective beam splitter in the plurality of beam splitters is a wavelength-independent beam splitters.

25. The imaging device of claim 1, wherein each image in the plurality of images is a multi-pixel image of the tissue of the subject, the method further comprising:
v) combining each image in the plurality of images, on a pixel by pixel basis, to form a composite image.

26. The imaging device of claim 1, wherein,
the imaging device is portable and powered independent of a power grid during first period of time and the second period of time,
the plurality of light source sets collectively comprises a plurality of first light sources and a plurality of second light sources,
the plurality of first light sources collectively provide at least 80 watts of illuminating power during the firing i),
the plurality of second light sources collectively provide at least 80 watts of illuminating power during the firing iii), and
the imaging device further comprises a capacitor bank in electrical communication with each first light source and each second light source, wherein a capacitor in the capacitor bank has a voltage rating of at least 2 volts and a capacitance rating of at least 80 farads.

27. The imaging device of claim 1, wherein the two discrete bands of a multi-bandpass filter in the plurality of multi-bandpass filters are separated by at least 60 nm.

28. The imaging device of claim 1, wherein the imaging device is portable and electrically independent of a power grid during the firing i) and the firing iii), and wherein the firing i) occurs for less than 300 milliseconds and the firing iii) occurs for less than 300 milliseconds.

29. The imaging device of claim 2, further comprising:
a first circuit board positioned on a first side of the optical assembly, wherein a first pixel array photo-sensor and a third pixel array photo-sensor in the plurality of pixel array photo-sensors are coupled to the first circuit board; and
a second circuit board positioned on a second side of the optical assembly opposite to the first side, wherein the second circuit board is substantially parallel with the first circuit board, wherein a second pixel array photo-sensor and a fourth pixel array photo-sensor in the plurality of pixel array photo-sensors are coupled to the second circuit board, and
wherein:
the first beam splitter is configured to split light received from the at least one objective lens into a first optical path and a second optical path, wherein the first optical path is substantially collinear with an optical axis defined by the light incoming from at least one objective lens to the optical assembly, and the second optical path is substantially perpendicular to the optical axis,
the second beam splitter is configured split light from the first optical path into a third optical path and a fourth optical path, wherein the third optical path is substantially collinear with the first optical path, and the fourth optical path is substantially perpendicular to the optical axis,
a third beam splitter in the plurality of beam splitters is configured to split light from the second optical path into a fifth optical path and a sixth optical path, wherein the fifth optical path is substantially collinear with the second optical path, and the sixth optical path is substantially perpendicular to the second optical path, and wherein the optical path assembly further comprises:
a first beam steering element configured to deflect light from the third optical path perpendicular to the third optical path and onto the first pixel array photo-sensor coupled to the first circuit board,
a second beam steering element configured to deflect light from the fourth optical path perpendicular to the fourth optical path and onto the second pixel array photo-sensor coupled to the second circuit board,
a third beam steering element configured to deflect light from the fifth optical path perpendicular to the fifth optical path and onto the third pixel array photo-sensor coupled to the first circuit board, and
a fourth beam steering element configured to deflect light from the sixth optical path perpendicular to the sixth optical path and onto the fourth pixel array photo-sensor coupled to the second circuit board.

30. The imaging device of claim 29, wherein
a first multi-bandpass filter in the plurality of multi-bandpass filters is positioned in the third optical path between the first beam splitter and the first pixel array photo-sensor,
a second multi-bandpass filter in the plurality of multi-bandpass filters is positioned in the fourth optical path between the second beam splitter and the second pixel array photo-sensor,
a third multi-bandpass filter in the plurality of multi-bandpass filters is positioned in the fifth optical path between the third beam splitter and the third pixel array photo-sensor, and a fourth multi-bandpass filter in the plurality of multi-bandpass filters is positioned in the sixth optical path between the fourth beam splitter and the fourth pixel array photo-sensor.

31. The imaging device of claim 29, further comprising a polarizing filter disposed along the optical axis.

32. The imaging device of claim 29, wherein the polarizing filter is adjacent to the at least one objective lens and before the first beam splitter along the optical axis.

33. The imaging device of claim 29, wherein the first beam steering element is a folding prism.

34. The imaging device of claim 29, wherein each respective beam splitter and each respective beam steering element is oriented along substantially the same plane.

35. The imaging device of claim 29, wherein the first beam splitter, the second beam splitter, and the third beam splitter each exhibits a ratio of light transmission to light reflection of about 50:50.

36. The imaging device of claim 1, wherein
the plurality of light source sets collectively comprises a plurality of first light sources and a plurality of second light sources,
each light source in the plurality of first light sources is a white light-emitting diode covered by a respective first light source filter that blocks light emitted by the white light-emitting diode other than the first spectral range, and
each light source in the plurality of second light sources is a white light-emitting diode covered by a respective second light source filter that blocks light emitted by the white light-emitting diode other than the second spectral range.

37. The imaging device of claim 1, wherein
each light source in each light source set is covered by a first polarizer, and
the at least one objective lens is covered by a second polarizer.

38. The imaging device of claim 3, wherein the beam steering element comprises a mirror mounted on an actuator, the actuator having the plurality of operating modes.

39. The imaging device of claim 38, wherein the mirror is a single-surface mirror.

40. The imaging device of claim 38, wherein the mirror is a two-axis micro electro-mechanical (MEMS) mirror.

41. The imaging device of claim 3, wherein the beam steering element comprises an array of micromirrors.

42. The hyperspectral/multispectral imaging device of claim 41, wherein the array of micromirrors comprises a digital micromirror device.

43. The imaging device of claim 3, wherein the plurality of pixel array photo-sensors comprises at least four pixel array photo-sensors.

44. The imaging device of claim 1, wherein each respective pixel array photo-sensor in the plurality of pixel array photo-sensors is used for detecting a different frequency of radiation.

45. The imaging device of claim 3, wherein the collecting ii) comprises placing the beam steering element in an operating mode in the plurality of operating modes that causes the beam steering element to be in optical communication with a corresponding pixel array photo-sensor in the plurality of pixel array photo-sensors.

46. The imaging device of claim 1, further comprising a housing display disposed on the exterior of the housing, the housing display in electronic communication with the controller, wherein the method further comprises displaying an image captured by a respective pixel array photo-sensor in the plurality of pixel array photo-sensors on the housing display.

47. The imaging device of claim 1, wherein
the plurality of light source sets comprises two light source sets, and
a first light source set in the two light source sets is arranged with respect to the at least one objective lens so that a first light source of the first light source set opposes a first light source of the second light source set, a second light source of the first light source set opposes a second light source of the second light source set, and a third light source of the first light source set opposes a third light source of the second light source set with respect to the at least one objective lens, and
the method further comprises:
iii) firing a third light in each light source set in the plurality of light source sets for a third period of time while not firing the first light source or the second light source in each light source set, and
iv) collecting a third set of images during the third period of time using at least a third subset of the plurality of pixel array photo-sensors.

48. The imaging device of claim 47, wherein
a fourth light source in the first light source set opposes a fourth light source of the second light source set in the two light source sets with respect to the at least one objective lens, and the method further comprises:
v) firing a fourth light in each light source set in the plurality of light source sets for a fourth period of time while not firing the first light source, the second light source, or the third light source in each light source set, and
vi) collecting a fourth set of images during the fourth period of time using at least a fourth subset of the plurality of pixel array photo-sensors.

49. The imaging device of claim 1 wherein each light source set in the plurality of light source sets consists of two light sources.

50. The imaging device of claim 1, wherein each light source set in the plurality of light source sets comprises 2+N light sources, wherein N is a positive integer.

* * * * *